(12) United States Patent
Lin et al.

(10) Patent No.: US 12,246,076 B2
(45) Date of Patent: Mar. 11, 2025

(54) RADIOLABELED COMPOUNDS FOR IN VIVO IMAGING OF GASTRIN-RELEASING PEPTIDE RECEPTOR (GRPR) AND TREATMENT OF GRPR-RELATED DISORDERS

(71) Applicants: PROVINCIAL HEALTH SERVICES AUTHORITY, Vancouver (CA); THE UNIVERSITY OF BRITISH COLUMBIA, Vancouver (CA)

(72) Inventors: Kuo-Shyan Lin, Richmond (CA); François Bénard, Vancouver (CA); Lei Wang, Vancouver (CA); Zhengxing Zhang, Langley (CA); Ivica Bratanovic, Port Moody (CA); Chengcheng Zhang, Richmond (CA)

(73) Assignees: PROVINCIAL HEALTH SERVICES AUTHORITY, Vancouver (CA); THE UNIVERSITY OF BRITISH COLUMBIA, Vancouver (CA)

( * ) Notice: Subject to any disclaimer, the term of this patent is extended or adjusted under 35 U.S.C. 154(b) by 0 days.

(21) Appl. No.: 18/512,708

(22) Filed: Nov. 17, 2023

(65) Prior Publication Data
US 2024/0123099 A1 Apr. 18, 2024

Related U.S. Application Data

(63) Continuation of application No. PCT/CA2023/050401, filed on Mar. 24, 2023.

(60) Provisional application No. 63/323,831, filed on Mar. 25, 2022.

(51) Int. Cl.
*A61K 51/00* (2006.01)
*A61K 51/08* (2006.01)
*A61M 36/14* (2006.01)

(52) U.S. Cl.
CPC ........ *A61K 51/088* (2013.01); *A61K 2121/00* (2013.01); *A61K 2123/00* (2013.01)

(58) Field of Classification Search
CPC .............. A61K 51/088; A61K 2121/00; A61K 2123/00; A61P 35/00; C07K 1/13; C07K 14/595
See application file for complete search history.

(56) References Cited

U.S. PATENT DOCUMENTS

| | | | |
|---|---|---|---|
| 9,035,023 B2 | 5/2015 | Maecke et al. | |
| 9,839,703 B2 | 12/2017 | Maina-Nock et al. | |
| 2021/0402016 A1 | 12/2021 | Benard et al. | |

FOREIGN PATENT DOCUMENTS

| | | | | |
|---|---|---|---|---|
| EP | 2198878 A1 | 6/2010 | | |
| EP | 2900279 A1 | 8/2015 | | |
| EP | 2900279 B1 | 8/2019 | | |
| JP | 2000502055 A | 2/2000 | | |
| JP | 2010150253 A | 7/2010 | | |
| JP | 2011515338 A | 5/2011 | | |
| JP | 2015533119 A | 11/2015 | | |
| WO | WO-9719954 A1 | 6/1997 | | |
| WO | WO-2009109332 A1 | 9/2009 | | |
| WO | WO-2014052471 A1 | 4/2014 | | |
| WO | WO-2021053040 A1 | * | 3/2021 | ............. A61K 47/12 |
| WO | WO-2021068051 A1 | 4/2021 | | |

OTHER PUBLICATIONS

Hofstetter et al. (EJNMMI Radiopharm. Chem. 2020, 5, 1-19).*
Mansi et al. (J. Med. Chem. 2015, 58, 682-691).*
Popp et al. (Nucl. Med. Biol. 2017, 45, 22-29).*
Accardo et al. (EJNMMI Res. 2016, 6, p. 1-10).*
Bratanovic et al. (J. Nucl. Med. 2022, 63, 424-430).*
Bratanovic (2020) Optimized Bombesin Analogues as Nuclear Imaging and Therapy Agents for Gastrin-Releasing Peptide Receptor Positive. [Masters of Science, The University of British Columbia] http://hdl.handle.net/2429/75181.*
Abd-Elgaliel, W.R. et al., Design, synthesis, and biological evaluation of an antagonist-bombesin analogue as targeting vector. Bioconjug Chem. Oct. 2008;19(10):2040-8. doi: 10.1021/bc800290c. Epub Sep. 23, 2008.
Amouroux, G. et al, Imaging Bradykinin B1 Receptor with 68Ga-Labeled [des-Arg10]Kallidin Derivatives: Effect of the Linker on Biodistribution and Tumor Uptake. Mol Pharm. Aug. 3, 2015;12(8):2879-88. doi: 10.1021/acs.molpharmaceut.5b00070. Epub Jul. 2, 2015.
Bajo, A.M. et al., Bombesin antagonists inhibit growth of MDA-MB-435 estrogen-independent breast cancers and decrease the expression of the ErbB-2/HER-2 oncoprotein and c-jun and c-fos oncogenes. Proc Natl Acad Sci USA. Mar. 19, 2002;99(6):3836-3841.
Bakker, I.L. et al. In Vivo Stabilized SB3, an Attractive GRPR Antagonist, for Pre- and Intra-Operative Imaging for Prostate Cancer. Mol Imaging Biol. Dec. 2018;20(6):973-983. doi: 10.1007/s11307-018-1185-z.

(Continued)

*Primary Examiner* — Michael G. Hartley
*Assistant Examiner* — Melissa J Perreira
(74) *Attorney, Agent, or Firm* — COOLEY LLP

(57) ABSTRACT

There is provided peptidic compounds of Formula I, A or B($R^{rad}_{n6}$-[linker]-$R^L$-$Xaa^1$-$Xaa^2$-$Xaa^3$-$Xaa^4$-$Xaa^5$-$Xaa^6$-$Xaa^7$-$Xaa^8$-ψ-$Xaa^9$-$NH_2$). $Xaa^1$ is D-Phe, Cpa, D-Cpa, Nal, D-Nal, 2-Nal, or D-2-Nal; $Xaa^2$ is Asn, Gln, Hse, Cit or His. $Xaa^3$ is Trp, Bta, Trp(Me), Trp(7-Me), Trp(6-Me), Trp(5-Me), Trp(4-Me), Trp(2-Me), Trp(7-F), Trp(6-F), Trp(5-F), Trp(4-F), Trp(5-OH), or αMe-Trp. $Xaa^4$ is Ala or Ser. $Xaa^5$ is Val, Cpg, or Tle. $Xaa^6$ is Gly, NMe-Gly, or D-Ala. $Xaa^7$ is His or NMe-His. $Xaa^8$ is Leu or Phe. $Xaa^9$-$NH_2$ is a C-terminally amidated amino acid residue selected from Pro, 4-oxa-L-Pro, $Me_2$ Thz, or Thz. ψ represents a peptide bond or reduced peptide bond joining $Xaa^8$ to $Xaa^9$. $R^{rad}_{n6}$ is 1-5 radiolabeling groups. There is also provided the use of such compounds as imaging agents or therapeutic agents.

14 Claims, 19 Drawing Sheets

Specification includes a Sequence Listing.

(56) References Cited

OTHER PUBLICATIONS

Baratto, L. et al., Prostate Cancer Theranostics Targeting Gastrin-Releasing Peptide Receptors. Molecular Imaging & Biology, Dec. 18, 2017;20(4):501-509.
Baum, R. et al. Molecular imaging of bombesin receptors in various tumors by Ga-68 AMBA PET/CT: First results. Journal of Nuclear Medicine. May 2007;48(supplement 2):79P, Abstract 265 [online]. Retrieved from: https://jnm.snmjournals.org/content/48/supplement_2/79P.2, 2 pages.
Berge, S. M., et al., "Pharmaceutical salts", Journal of Pharmaceutical Sciences (1977); 66(1): 1-19.
Bitar, K.N. et al., "Expression of bombesin-receptor subtypes and their differential regulation of colonic smooth muscle contraction," Gastroenterology, 105:1672-1680 (1993).
Bodei, Lisa et al. (2007). Lu-177-AMBA Bombesin Analogue in Hormone Refractory Prostate Cancer Patients: A Phase I Escalation Study with Single-Cycle Administrations. In: Joint Eanm-Eortc Symposium, Annual Congress of the European Association of Nuclear Medicine, Oct. 12-16, 2019, Barcelona, Spain. Eur. J. Nucl. Med. Mol. Imaging. 34. p. S221, #463.
Bratanovic, I.J. et al. The Effect of a Cationic Linker on the Pharmacokinetics of ProBOMB2, a Novel Bombesin Derivative. Annual Congress of the European Association of Nuclear Medicine, Oct. 12-16, 2019, Barcelona, Spain. Eur J Nucl Med Mol Imaging, Sep. 18, 2019;46(Suppl 1):271, Abstract OP-709, 1 page.
Cai, P. et al., "Potent bombesin antagonists with C-terminal Leu-psi(CH2-N)-Tac-NH2 or its derivatives," Proc. Natl. Acad. Sci. USA, 91:12664-12668 (Dec. 1994).
Cai, R-Z. et al., New pseudononapeptide bombesin antagonists with C-terminal Leu-psi(CH2N)Tac-NH2 show high binding affinity to bombesin/GRP receptors on CFP AC-1 human pancreatic cancer cells. Int J Oncol., 6:1165-1172 (1995).
Chansaenpak, K. et al., [18 F]-NHC-BF3 adducts as water stable radio-prosthetic groups for PET imaging. Chemical Communications, Jun. 2015;51(62):12439-12442.
Cornelio, D.B. et al., Gastrin-releasing peptide receptor as a molecular target in experimental anticancer therapy. Ann Oncol.;18:1457-1466 (2007).
Coy, D.H. et al., Probing peptide backbone function in bombesin. A reduced peptide bond analogue with potent and specific receptor antagonist activity. J Biol Chem. Apr. 15, 1988;263(11):5056-5060.
Dalm S.U. et al. 68Ga/177Lu-NeoBOMB1, a Novel Radiolabeled GRPR Antagonist for Theranostic Use in Oncology. J Nucl Med. Feb. 2017;58(2):293-299. doi: 10.2967/jmuned.116.176636. Epub Sep. 8, 2016.
Dalm, S.U. et al., Prospects of Targeting the Gastrin Releasing Peptide Receptor and Somatostatin Receptor 2 for Nuclear Imaging and Therapy in Metastatic Breast Cancer. PLoS One. Jan. 20, 2017;12(1):e0170536, 12 pages.
De Visser, M. et al., Novel 111In-labelled bombesin analogues for molecular imaging of prostate tumours. Eur J Nucl Med Mol Imaging;34:1228-1238 (2007).
Eder, M. et al., Preclinical Evaluation of a Bispecific Low-Molecular Heterodimer Targeting Both PSMA and GRPR for Improved PET Imaging and Therapy of Prostate Cancer. The Prostate, 2014; 74:659-668.
European Application No. 19948391.8: Extended European Search Report, dated Aug. 22, 2022, 10 pages.
Fani, M. et al., Radiolabeled peptides: Valuable tools for the detection and treatment of cancer. Theranostics. 2012; 2(5):481-501 (2012).
Gonzalez, N. et al., "Molecular basis for the selectivity of the mammalian bombesin peptide, neuromedin B, for its receptor," J Pharmacol Exp Ther.;331(1):265-276 (2009).
Gunther, T. et al. Optimization of the pharmacokinetic profile of 99mTc-N4- Bombesin derivatives by modification of the pharmacophoric Gln-Trp sequence. Journal of Nuclear Medicine. May 2021;62(supplement 1), Abstract 1474 [online]. Retrieved from: https://jnm.snmjournals.org/content/62/supplement_1/1474, 2 pages.
Gunther, T. et al. Substitution of L-Tryptophan by a-Methyl-L-Tryptophan in 177Lu-RM2 Results in 177Lu-AMTG, a High-Affinity Gastrin-Releasing Peptide Receptor Ligand with Improved In Vivo Stability. J Nucl Med. 2022;63(9):1364-1370, DOI: https://doi.org/10.2967/jnumed.121.263323.
Guo, M. et al., Bombesin-like peptides and their receptors: recent findings in pharmacology and physiology. Curr Opin Endocrinol Diabetes Obes. 2015;22(1): 3-8.
Heimbrook, D.C. et al., "Gastrin releasing peptide antagonists with improved potency and stability," J. Med. Chem. 34:2102-2107 (1991).
Horwell, D.C. et al., "Alanine scan and N-methyl amide derivatives of Ac-bombesin[7-14]. Development of a proposed binding conformation at the neuromedin B (NMB) and gastrin releasing peptide (GRP) receptors," Int. J. Peptide Protein Res., 48:522-531 (1996).
Inkster, J. et al., 2-Fluoropyridine prosthetic compounds for the 18F labeling of bombesin analogues. Bioorganic Med Chem Lett.;23:3920-3926 (2013).
International Search Report & Written Opinion dated Jan. 22, 2020, for International Application No. PCT/CA2019/051620, 11 pages.
International Search Report and Written Opinion for International Application No. PCT/CA2023/050401 dated Jun. 7, 2023, 10 pages.
Ischia, J. et al., Expression and function of gastrin-releasing peptide (GRP) in normal and cancerous urological tissues. BJU Int. 2014;113 Suppl 2:40-47.
Jensen, R.T. et al., "International Union of Pharmacology. LXVIII. Mammalian Bombesin Receptors: Nomenclature, Distribution, Pharmacology, Signaling, and Functions in Normal and Disease States," Pharmacol Rev. Mar. 2008;60(1):1-42. doi: 10.1124/pr.107.07108. Epub Nov. 30, 2007. NIH Public Access Author Manuscript [online]. Retrieved from: https://www.ncbi.nlm.nih.gov/pmc/articles/PMC2517428/pdf/nihms-45053.pdf, 74 printed pages.
Jungwirth, A. et al, "Inhibition of growth of androgen-independent DU-145 prostate cancer in vivo by luteinising hormone-releasing hormone antagonist cetrorelix and bombesin antagonists RC-3940-II and RC-3950-11," Eur J Cancer Part A., 33(7):1141-1148 (1997).
Keenan, M.A. et al., "RADAR Realistic Animal Model Series for Dose Assessment," J Nucl Med, 2010, vol. 51, No. 3, pp. 471-476.
Kähkönen, E. et al., In vivo imaging of prostate cancer using [68Ga]-labeled bombesin analog BAY86-7548. Clin Cancer Res. Oct. 1, 2013;19(19):5434-43. doi: 10.1158/1078-0432.CCR-12-3490. Epub Aug. 9, 2013.
Koppan, M. et al., "Bombesin/gastrin-releasing peptide antagonists RC-3095 and RC-3940-II inhibit tumor growth and decrease the levels and mRNA expression of epidermal growth factor receptors in H-69 small cell lung carcinoma," Cancer; 83:1335-1343 (1998).
Kuo, H-T. et al., "One-Step 18F-Labeling and Preclinical Evaluation of Prostate-Specific Membrane Antigen Trifluoroborate Probes for Cancer Imaging," J Nucl Med, 2019; 60:1160-1166, DOI: 10.2967/jnumed.118.216598.
Kurth, J. et al. First-in-human dosimetry of gastrin-releasing peptide receptor antagonist [177Lu]Lu-RM2: a radiopharmaceutical for the treatment of metastatic castration-resistant prostate cancer. Eur J Nucl Med Mol Imaging. Jan. 2020;47(1):123-135. doi: 10.1007/s00259-019-04504-3. Epub Sep. 3, 2019.
Lau, J. et al., Positron Emission Tomography Imaging of the Gastrin-Releasing Peptide Receptor with a Novel Bombesin Analogue. ACS Omega. Jan. 31, 2019;4(1):1470-1478. doi: 10.1021/acsomega.8b03293. Epub Jan. 16, 2019.
Leban, J.J. et al., Development of potent gastrin-releasing peptide antagonists having a D-Pro-psi(CH2NH)-Phe-NH2 C terminus. Proc Natl Acad Sci U S A. Mar. 1, 1993;90(5):1922-6. doi: 10.1073/pnas.90.5.1922.
Leban, J.J. et al. Potent gastrin-releasing peptide (GRP) antagonists derived from GRP(19-27) with a C-terminal DPro psi[CH2NH]Phe-NH2 and N-terminal aromatic residues. J Med Chem. Feb. 18, 1994;37(4):439-445. doi: 10.1021/jm00030a002.
Li, L. et al. Functionally Versatile and Highly Stable Chelator for 111In and 177Lu: Proof-of-Principle Prostate-Specific Membrane

(56) References Cited

OTHER PUBLICATIONS

Antigen Targeting. Bioconjug Chem. May 15, 2019;30(5):1539-1553. doi: 10.1021/acs.bioconjchem.9b00225. Epub May 5, 2019.
Li, Y. et al., "Evaluation of 227Th chelation of hydroxypyridinone- and picolinic acid containing ligands to simulate 226Th chelation", Poster #102, University of Washington, 2018. Nuclear Medicine and Biology, 2019;72-73(Supplement 1):S38, 1 page.
Lin, J.T. et al., Comparison of the peptide structural requirements for high affinity interaction with bombesin receptors. Eur J Pharmacol. Dec. 27, 1995;294(1):55-69. doi: 10.1016/0014-2999(95)00510-2.
Lin, K-S. et al. A new high affinity technetium analogue of bombesin containing DTPA as a pharmacokinetic modifier. Bioconjug Chem. Nov.-Dec. 2004;15(6):1416-23. doi: 10.1021/bc0498267.
Lin, K-S. et al., "In vivo radioimaging of bradykinin receptor b1, a widely overexpressed molecule in human cancer," Cancer Res. Jan. 2015;75(2):387-393. doi:10.1158/0008-5472.CAN-14-1603.
Linder, K.E. et al. In vitro and in vivo metabolism of Lu-AMBA, a GRP-receptor binding compound, and the synthesis and characterization of its metabolites. Bioconjug Chem. Jun. 2009;20(6):1171-8. doi: 10.1021/bc9000189.
Liu, Z. et al., "An Organotrifluoroborate for Broadly Applicable One-Step18F-Labeling," Angewandte Chemie International Edition, Sep. 2014, vol. 53, No. 44, pp. 11876-11880.
Liu, Z. et al., "One-step 18F labeling of biomolecules using organotrifluoroborates," Nat Protoc, Sep. 2015, vol. 10, No. 9, pp. 1423-1432.
Liu, Z. et al., Preclinical Evaluation of a High-Affinity $^{18}$F-Trifluoroborate Octreotate Derivative for Somatostatin Receptor Imaging. Journal of Nuclear Medicine, Sep. 2014, vol. 55(9), pp. 1499-1505.
Maina, T. et al., Preclinical and first clinical experience with the gastrin-releasing peptide receptor antagonist [68Ga]SB3 and PET/CT. Eur J Nucl Med Mol Imaging; 43:964-973 (2016).
Maina, T. et al., Theranostic Prospects of Gastrin-Releasing Peptide Receptor-Radioantagonists in Oncology. PET Clin.;12:297-309 (2017).
Mansi, R. et al., "Bombesin-Targeted PET of Prostate Cancer," J Nucl Med.; 57:67S-72S (2016).
Minamimoto, R. et al., "Pilot Comparison of 68Ga-RM2 PET and 68Ga-PSMA-11 PET in Patients with Biochemically Recurrent Prostate Cancer," J Nucl Med. 2016;57:557-562.
Morgat, C. et al., "Expression of Gastrin-Releasing Peptide Receptor in Breast Cancer and Its Association with Pathologic, Biologic, and Clinical Parameters: A Study of 1,432 Primary Tumors," J Nucl Med.;58:1401-1407 (2017).
Nock, B.A. et al., "To Serve and Protect": Enzyme Inhibitors as Radiopeptide Escorts Promote Tumor Targeting, J Nucl Med.; 55:121-127 (2014).
Nock, B.A. et al., Theranostic Perspectives in Prostate Cancer with the Gastrin-Releasing Peptide Receptor Antagonist NeoBOMB1: Preclinical and First Clinical Results. J Nucl Med. Jan. 2017;58(1):75-80. doi: 10.2967/jnumed.116.178889. Epub Aug. 4, 2016.
Pan D. et al. A new (68)Ga-labeled BBN peptide with a hydrophilic linker for GRPR-targeted tumor imaging. Amino Acids. Jun. 2014;46(6):1481-9. doi: 10.1007/s00726-014-1718-y. Epub Mar. 17, 2014.
Pourghisian, M. et al., "$^{18}$F-AmBF$_3$-MJ9: a novel radiofluorinated bombesin derivative for prostate cancer imaging," Bioorganic & Medicinal Chemistry, 2015, vol. 23, No. 7, pp. 1500-1506.
Price, E.W. and C. Orvig, "Matching chelators to radiometals for radiopharmaceuticals," Chem Soc Rev, vol. 43, pp. 260-290 (2014).
Ramos-Alvarez, I. et al. Insights into bombesin receptors and ligands: Highlighting recent advances. Peptides. Oct. 2015;72:128-44. doi: 10.1016/j.peptides.2015.04.026. Epub May 11, 2015.
Reile, H. et al. New antagonists of bombesin gastrin-releasing peptide with C-terminal Leu-psi-(CH2N)Tac-NH2. Int J Oncol. Oct. 1995;7(4):749-54. doi: 10.3892/ijo.7.4.749.
Richter, S. et al., Metabolically Stabilized 68Ga-NOTA-Bombesin for PET Imaging of Prostate Cancer and Influence of Protease Inhibitor Phosphoramidon. Mol Pharm.;13:1347-1357 (2016).
Roesler, R. et al., Gastrin-releasing peptide receptors in the central nervous system: Role in brain function and as a drug target. Front Endocrinol;3:159, 12 pages (Dec. 2012).
Rousseau, E. et al. Comparison of biological properties of [177 Lu]Lu-ProBOMB1 and [177 Lu]Lu-NeoBOMB1 for GRPR targeting. J Labelled Comp Radiopharm. Feb. 2020;63(2):56-64. doi: 10.1002/jlcr.3815. Epub Jan. 11, 2020.
Sah, B-R. et al., Dosimetry and First Clinical Evaluation of the New 18F-Radiolabeled Bombesin Analogue BAY 864367 in Patients with Prostate Cancer. J Nucl Med.; 56:372-378 (2015).
Shirahige, Y. et al, Inhibitory effect of bombesin/Gastrin-releasing peptide (GRP) antagonists RC-3950-II and RC-3095 onMCF-7 MIII human breast cancer xenografts in nude mice. Biomed Pharmacother.;48:465-472 (1994).
Sonni, I. et al., Imaging of Prostate Cancer Using Gallium-68-Labeled Bombesin. PET Clin.; 12:159-171 (2017).
Stabin, M.G. et al., "OLINDA/EXM: the second-generation personal computer software for internal dose assessment in nuclear medicine," J Nucl Med.;46:1023-1027 (2005).
Stoykow et al., Gastrin-releasing Peptide Receptor Imaging in Breast Cancer Using the Receptor Antagonist (68)Ga-RM2 And PET. Theranostics.;6:1641-1650 (2016).
Wang, L. et al. 68Ga-Labeled [Leu13ψThz14]Bombesin(7-14) Derivatives: Promising GRPR-Targeting PET Tracers with Low Pancreas Uptake. Molecules, 2022;27(12):3777, 14 pages. https://doi.org/10.3390/molecules27123777.
Weber, H.C., Regulation and signaling of human bombesin receptors and their biological effects. Curr Opin Endocrinol Diabetes Obes, 16:66-71 (2009).
Wieser, G. et al., "Positron emission tomography (PET) imaging of prostate cancer with a gastrin releasing peptide receptor antagonist—from mice to men," Theranostics, 4(4):412-419 (2014).
Zang, J. et al., "68Ga-NOTA-RM26 PET/CT in the Evaluation of Breast Cancer: A Pilot Prospective Study," Clin Nucl Med;43:663-669 (Sep. 2018); HHS Public Access Author Manuscript [online]. Retrieved from: https://www.ncbi.nlm.nih.gov/pmc/articles/PMC6076351/pdf/nihms974578.pdf, 16 printed pages.
Kaloudi, A. et al., NeoBOMB1, a GRPR-Antagonist for Breast Cancer Theragnostics: First Results of a Preclinical Study with [67Ga]NeoBOMB1 in T-47D Cells and Tumor-Bearing Mice. Molecules, Nov. 11, 2017;22(11):1950, 13 pages.
Baratto, L et al. PSMA- and GRPR-targeted PET: Results from 50 Patients with Biochemically Recurrent Prostate Cancer. Journal of Nuclear Medicine, Mar. 2021;65(8). doi:10.2967/jnumed.120.259630; 23 pages.
Conklin, B.R and Bourne, H.R. "Structural elements of Gα subunits that interact with Gβγ, receptors, and effectors", Cell. May 1993;73(4):631-641.
Ginj, M. et al. "Radiolabeled somatostatin receptor antagonists are preferable to agonists for in vivo peptide receptor targeting of tumors", Proc. Natl. Acad. Sci. U.S.A. Oct. 2006;103(44):16436-16441.
Gugger, M. and Reubi, J.C. "Gastrin-releasing peptide receptors in non-neoplastic and neoplastic human breast", The American Journal of Pathology, Dec. 1999;155(6):2067-2076.
Hajri, A. et al. "Expression and characterization of gastrin-releasing peptide receptor in normal and cancerous pancreas", Pancreas. 1996;12:25-35.
Jensen, R.T and Coy, D.H. "Progress in the development of potent bombesin receptor antagonists", Trends Pharmacol. Sci. Jan. 1991;12:13-19.
Lui, Y. et al. "G protein-coupled receptors as promising cancer targets", Cancer Lett. 2016;376(2):226-239.
Mansi, R. et al. "Targeting GRPR in urological cancers-from basic research to clinical application", Nat. Rev. Urol. Apr. 2013;10(4):235-244.
Markwalder, R. and Reubi, J.C. "Gastrin-releasing peptide receptors in the human prostate: relation to neoplastic transformation", Cancer Research. 1999;59:1152-1159.
Moody, T. et al. "GRP receptors are present in non small cell lung cancer cells", Journal of Cellular Biochemistry Supplement. 1996;24:247-256.

(56) References Cited

OTHER PUBLICATIONS

Moreno, P. et al. "Bombesin related peptides/receptors and their promising therapeutic roles in cancer imaging, targeting and treatment", Expert Opin. Ther. Targets. Sep. 2016;20(9):1055-1073. HHS Public Access Author Manuscript, 37 pages.

Preston, S.R. et al. "Characterization of a bombesin/gastrin-releasing peptide receptor on a human gastric-cancer cell line", International Journal of Cancer. 1994;57:734-741.

Preston, S.R. et al. "High-affinity binding sites for gastrin-releasing peptide on human colorectal cancer tissue but not uninvolved mucosa," British Journal of Cancer. 1995; 71:1087-1089.

* cited by examiner

RADIOLABELED COMPOUNDS FOR IN VIVO IMAGING OF GASTRIN-RELEASING PEPTIDE RECEPTOR (GRPR) AND TREATMENT OF GRPR-RELATED DISORDERS

CROSS-REFERENCE TO RELATED APPLICATIONS

This application is a continuation of International Application No. PCT/CA2023/050401, filed Mar. 24, 2023, which claims priority to U.S. Provisional Patent Application No. 63/323,831, filed on Mar. 25, 2022, the contents of each of which is hereby incorporated by reference in its entirety for all purposes.

REFERENCE TO SEQUENCE LISTING SUBMITTED ELECTRONICALLY

The contents of the electronic sequence listing (A9TH_020_01US_SeqList_ST26.xml; Size: 203,261 bytes; and Date of Creation: Nov. 16, 2023) are herein incorporated by reference in its entirety.

FIELD OF INVENTION

The present invention relates to radiolabelled compounds for in vivo imaging or treatment of diseases or conditions characterized by expression of the gastrin-releasing peptide receptor.

BACKGROUND OF THE INVENTION

Gastrin-releasing peptide receptor (GRPR) is a G protein-coupled receptor of the bombesin (BBN) receptor family (Roesler & Schwartsmann. 2012. *Front Endocrinol (Lausanne)* 3:159; Bitar & Zhu. 1993. *Gastroenterology*. 105:1672-1680; Weber. 2009. *Curr Opin Endocrinol Diabetes Obes.* 16:66-71). Together with its endogenous ligand, gastrin-releasing peptide (GRP), GRPR is involved in synaptic plasticity, emotional and feeding behavior, hormone secretion, smooth muscle contraction, and cell proliferation (ibid.). In normal conditions, the expression of GRPR is restricted to the central nervous system, pancreas, adrenal cortex and gastrointestinal tract (Jensen, et al. 2008. *Pharmacol Rev.* 60:1-42). GRPR is also implicated in neoplastic progression, with overexpression of GRPR having been reported in many cancer subtypes including lung, head and neck, colon, kidney, ovarian, breast and prostate cancers (Cornelio, et al. 2007. *Ann Oncol.* 18:1457-1466). This ectopic expression in cancers makes it an attractive target for personalized therapies.

BBN is a 14 amino acid GRPR binding peptide (Lin, et al. 2004. Bioconjugate Chemistry. Vol 15. American Chemical Society pages 1416-1423; Inkster, et al. 2013 *Bioorganic Med Chem Lett.* 23:3920-3926; Mansi, et al. 2016 *J Nucl Med.* 57:67S-72S; Bodei, et al. 2007. $^{177}$Lu-AMBA Bombesin analogue in hormone refractory prostate cancer patients: a phase I escalation study with single-cycle administrations. In: JOINT EANM-EORTC Symposium; Sah, et al. 2015 *J Nucl Med.* 56:372-378; Zang, et al. 2018 *Clin Nucl Med.* 43:663-669; Nock, et al. 2017 *J Nucl Med.* 58:75-80; Maina, et al. 2016 *Eur J Nucl Med Mol Imaging* 43:964-973). BBN derivatives have been radiolabeled for imaging with single photon emission computed tomography (SPECT), positron emission tomography (PET), and have also been radiolabeled for therapy with beta and alpha emitters (Maina, et al. PET Clin. 2017; 12:297-309; Lin, et al. 2004. Bioconjugate Chemistry. Vol 15. American Chemical Society pages 1416-1423; Inkster, et al. 2013 *Bioorganic Med Chem Lett.* 23:3920-3926). Often, a radiolabelled group is appended directly onto the structure or via a linker at the N-terminus, while modifications at the C-terminus dictate agonist/antagonist properties. For targeting GRPR, antagonists are preferred since agonists have been shown to induce gastrointestinal adverse events (Bodei, et al. 2007. $^{177}$Lu-AMBA Bombesin analogue in hormone refractory prostate cancer patients: a phase I escalation study with single-cycle administrations. In: JOINT EANM-EORTC Symposium). Examples of GRPR antagonists evaluated in the clinic include: $^{68}$Ga-RM2, $^{68}$Ga-SB3, $^{68}$Ga-NeoBOMB1, $^{68}$Ga-RM26, $^{18}$F-BAY-864367, and $^{64}$Cu-CB-TE2A-AR06 (Mansi, et al. 2016 *J Nucl Med.* 57:67S-72S; Sah, et al. 2015 *J Nucl Med.* 56:372-378; Zang, et al. 2018 *Clin Nucl Med.* 43:663-669; Nock, et al. 2017 *J Nucl Med.* 58:75-80; Maina, et al. 2016 *Eur J Nucl Med Mol Imaging* 43:964-973; Kahkonen, et al. Clin Cancer Res. 2013; 19:5434-5443, Kahkonen, et al. Clin Cancer Res. 2013; 19:5434-5443; Baum, et al. 2007 *Journal of Nuclear Medicine* 48, 79P-79P).

High pancreas uptake is the major limitation of currently reported GRPR-targeting radioligands. In a study, the high pancreas uptake of $^{68}$Ga-labeled AMBA was up to 54.9 SUV (SUV: standard uptake value) (Baum, et al. 2007 *Journal of Nuclear Medicine* 48, 79P-79P). In addition, $^{68}$Ga-labeled RM2 was also reported to show high uptake in pancreas (Kurth, et al. 2020. *European journal of nuclear medicine and molecular imaging* 47, 123-135; Minamimoto, et al. 2016 *J Nucl Med.* 57:557-562). It has also been reported that radiolabeled NeoBOMB1 showed high pancreas uptake in both PC-3 tumor-bearing mice and prostate cancer patients (Nock, et al. 2017 *J Nucl Med.* 58:75-80).

Another limitation for most of the reported GRPR-targeting ligands is their in vivo metabolic instability (Bakker, et al. 2018 *Molecular imaging and biology* 20, 973-983; Rousseau, et al. 2020 *Journal of Labelled Compounds and Radiopharmaceuticals* 63, 56-64) due to enzymatic degradation by neutral endopeptidase (NEP) (Nock, et al. 2014 *J Nucl Med.* 55:121-127). His$^{12}$-Leu$^{13}$, Trp$^{8}$-Ala$^{9}$ and Gln$^{7}$-Trp$^{8}$ were reported to be the main cleavage sites within the AMBA's sequence, and Trp$^{8}$-Ala$^{9}$, Ala$^{9}$-Val$^{10}$ and Gln$^{7}$-Trp$^{8}$ were considered to be the cleavage sites of RM2 (Kahkonen, et al. 2013 *Clin Cancer Res.* 19:5434-5443; Linder et al. 2009 *Bioconjugate chemistry* 20, 1171-1178).

There remains an unmet need in the field for improved tracers for the non-invasive in-vivo imaging of the GRPR. Such tracers are useful for the diagnosis of disorders related to aberrant/ectopic expression of GRPR, including but not limited to cancer (e.g. prostate cancer). There also remains an unmet need for improved radiotherapeutic agents for treatment of diseases/disorders related to aberrant/ectopic expression of GRPR, including but not limited to cancer (e.g. prostate cancer). In particular, there is a need for GRPR-targeting radioligands (for imaging and/or therapy) with lower pancreas uptake, and useful stability in vivo.

No admission is necessarily intended, nor should it be construed, that any of the preceding information constitutes prior art against the present invention.

SUMMARY

In one aspect, this disclosure provides a peptidic compound of Formula I (defined below). Such compounds may have lower pancreas uptake than prior art bombesin analogs as well as useful stability in vivo for imaging and/or radiotherapy.

BRIEF DESCRIPTION OF THE DRAWINGS

The features of the invention will become apparent from the following description in which reference is made to the appended drawings wherein.

DETAILED DESCRIPTION

Figure 1:
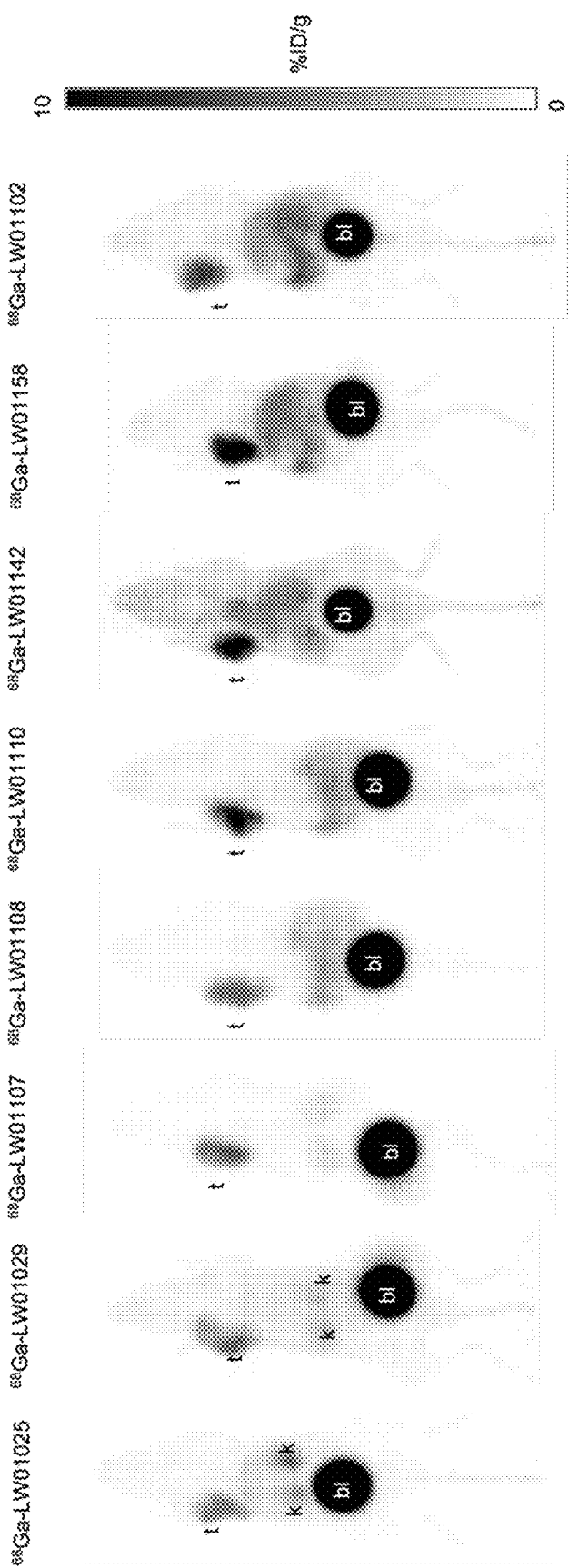
FIG. 1 shows representative maximum-intensity-projection PET images of $^{68}$Ga-LW01025, $^{68}$Ga-LW01029, $^{88}$Ga-LW01107, $^{88}$Ga-LW01108, $^{68}$Ga-LW01110, $^{68}$Ga-LW01142, $^{68}$Ga-LW01158 and $^{88}$Ga-LW01102 in mice bearing PC-3 tumor xenografts. The images were acquired at 1 h post-injection.
Figure 2:
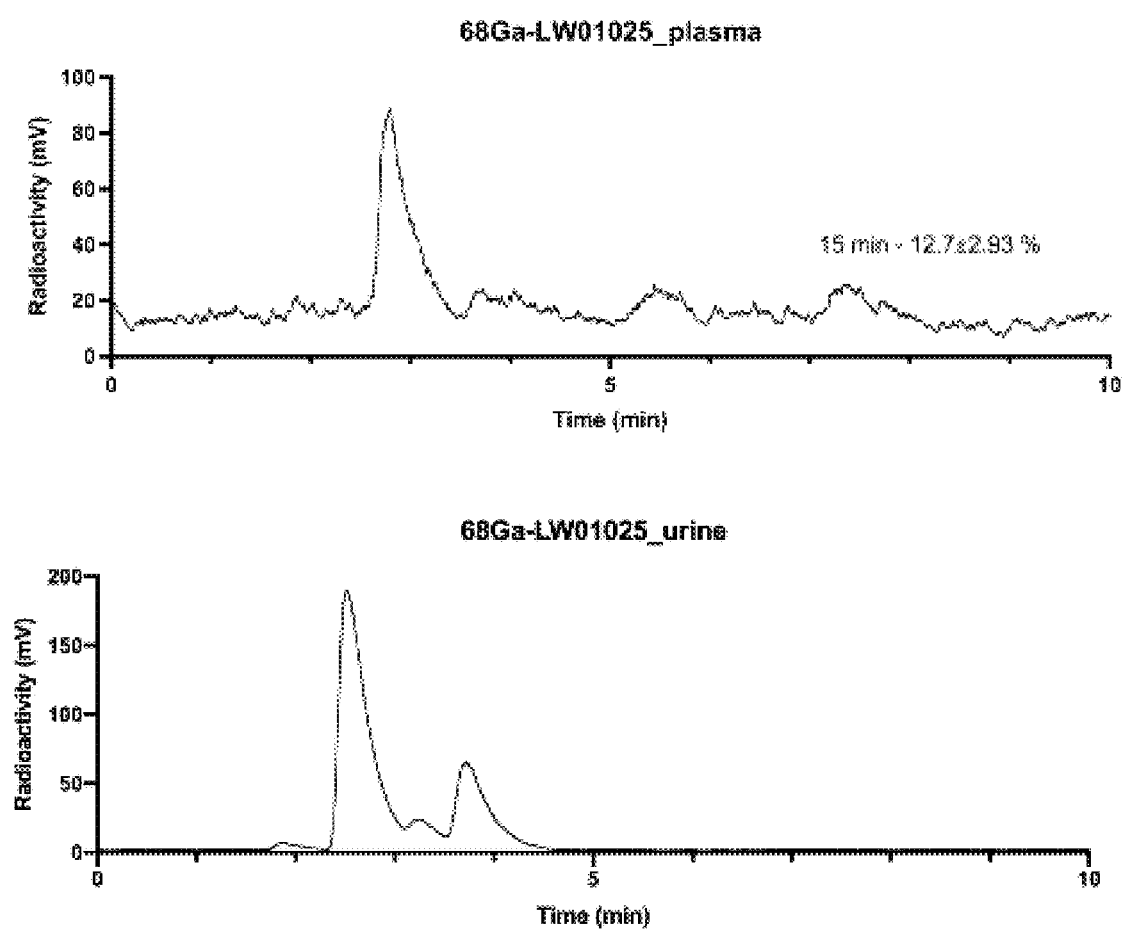
FIG. 2 shows representative radio-HPLC chromatograms of $^{68}$Ga -LW01025 extracted from mouse urine and plasma samples.
Figure 3:
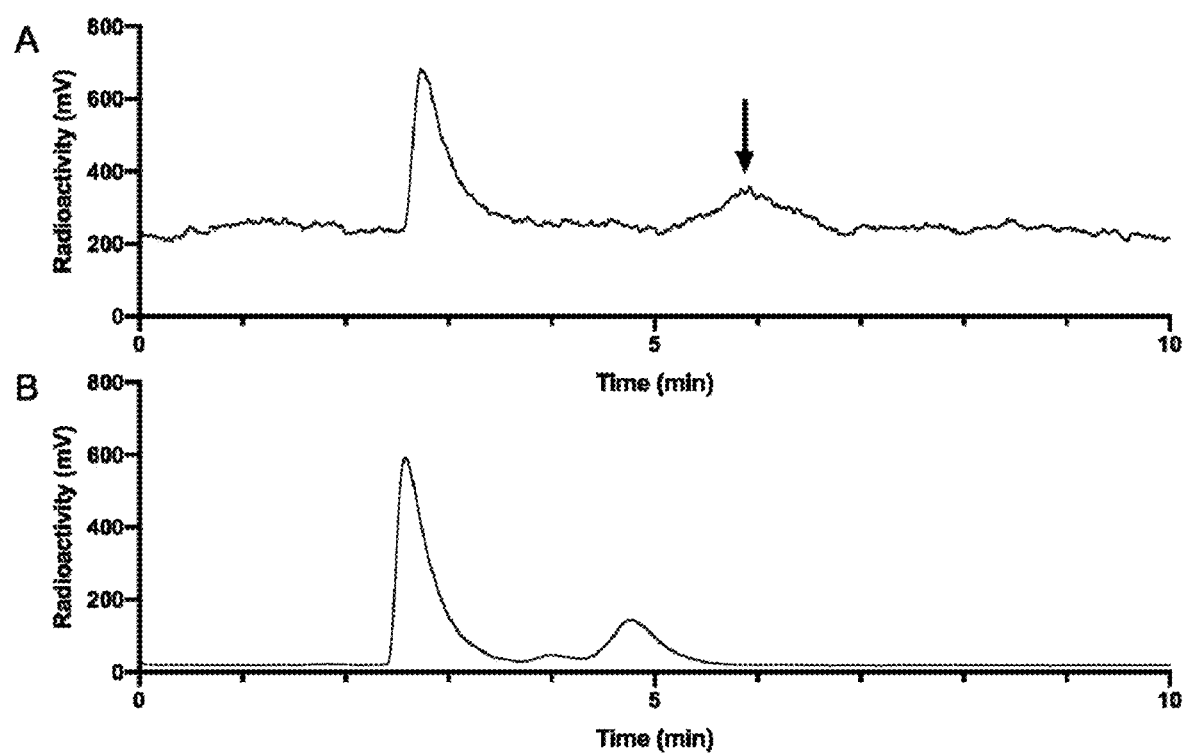
FIG. 3 shows representative radio-HPLC chromatograms from analysis of intact fraction of $^{68}$Ga-LW01029 in mouse plasma (A) and urine (B) samples collected at 15 min post-injection.
Figure 4:
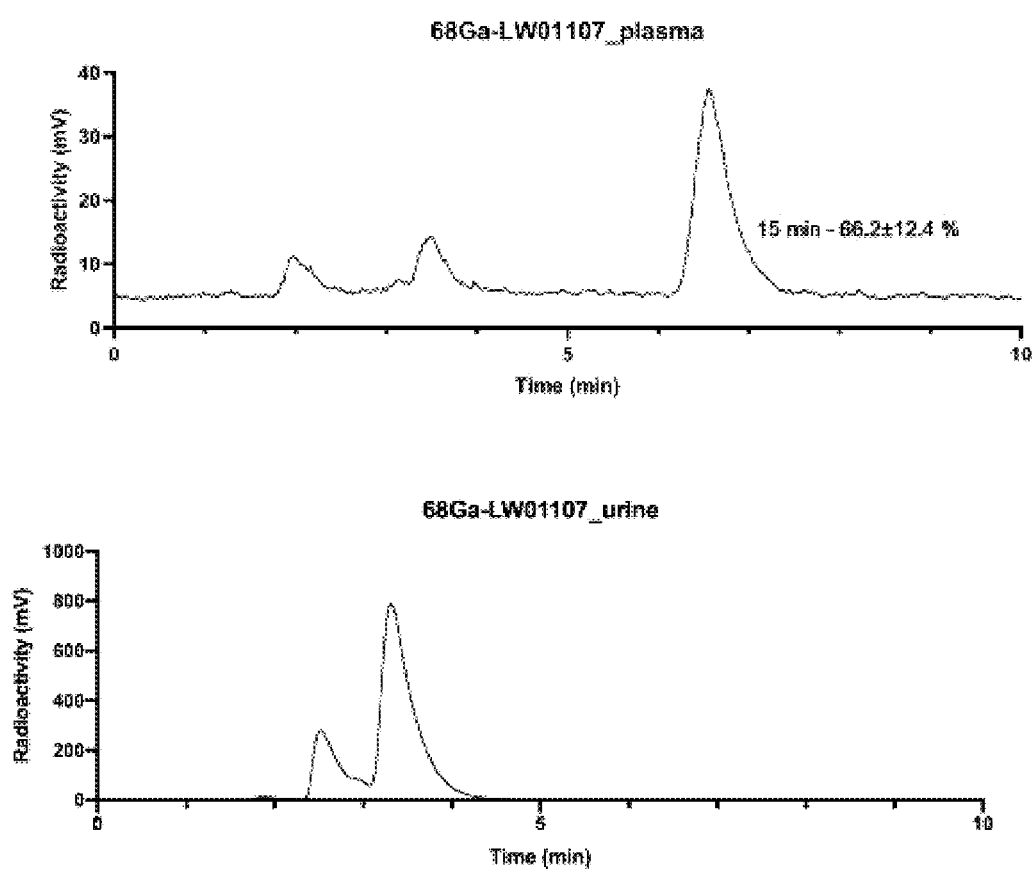
FIG. 4 shows representative radio-HPLC chromatograms of $^{88}$Ga-LW01107 extracted from mouse urine and plasma samples.
Figure 5:
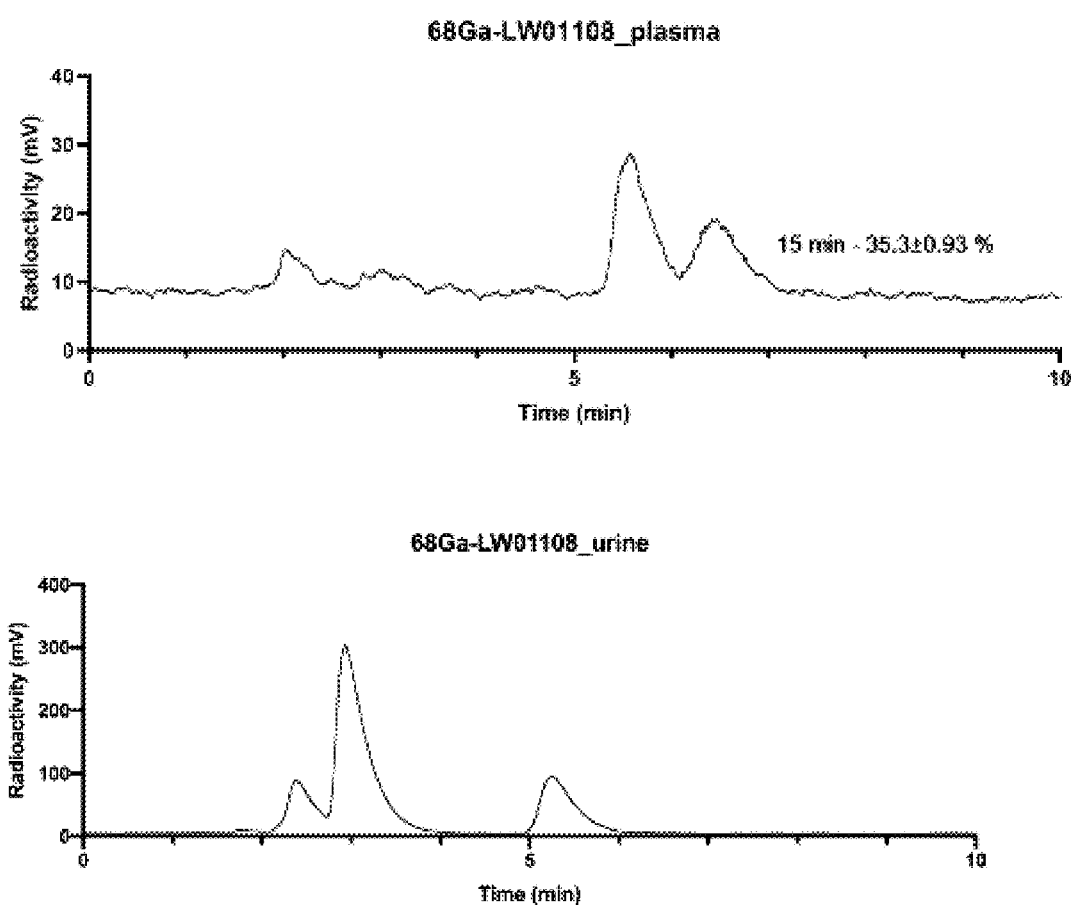
FIG. 5 shows representative radio-HPLC chromatograms of $^{68}$Ga-LW01108 extracted from mouse urine and plasma samples.
Figure 6:
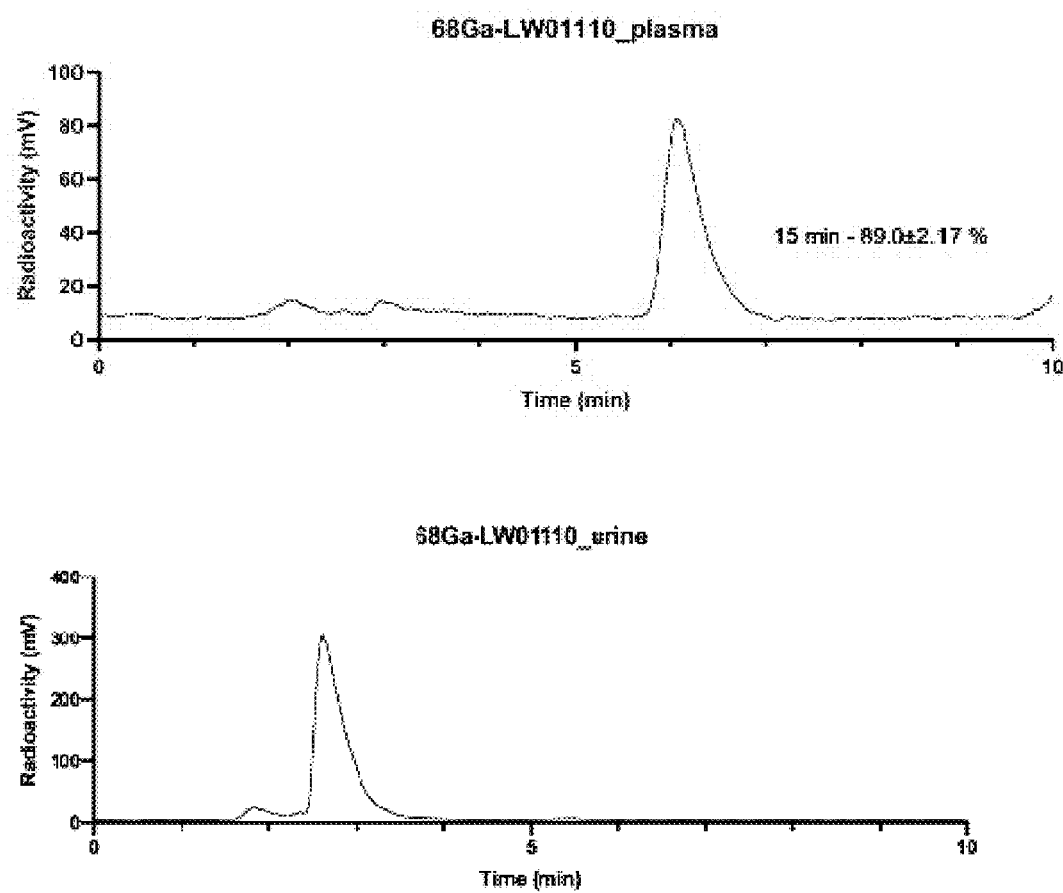
FIG. 6 shows representative radio-HPLC chromatograms of $^{68}$Ga-LW01110 extracted from mouse urine and plasma samples.
Figure 7:
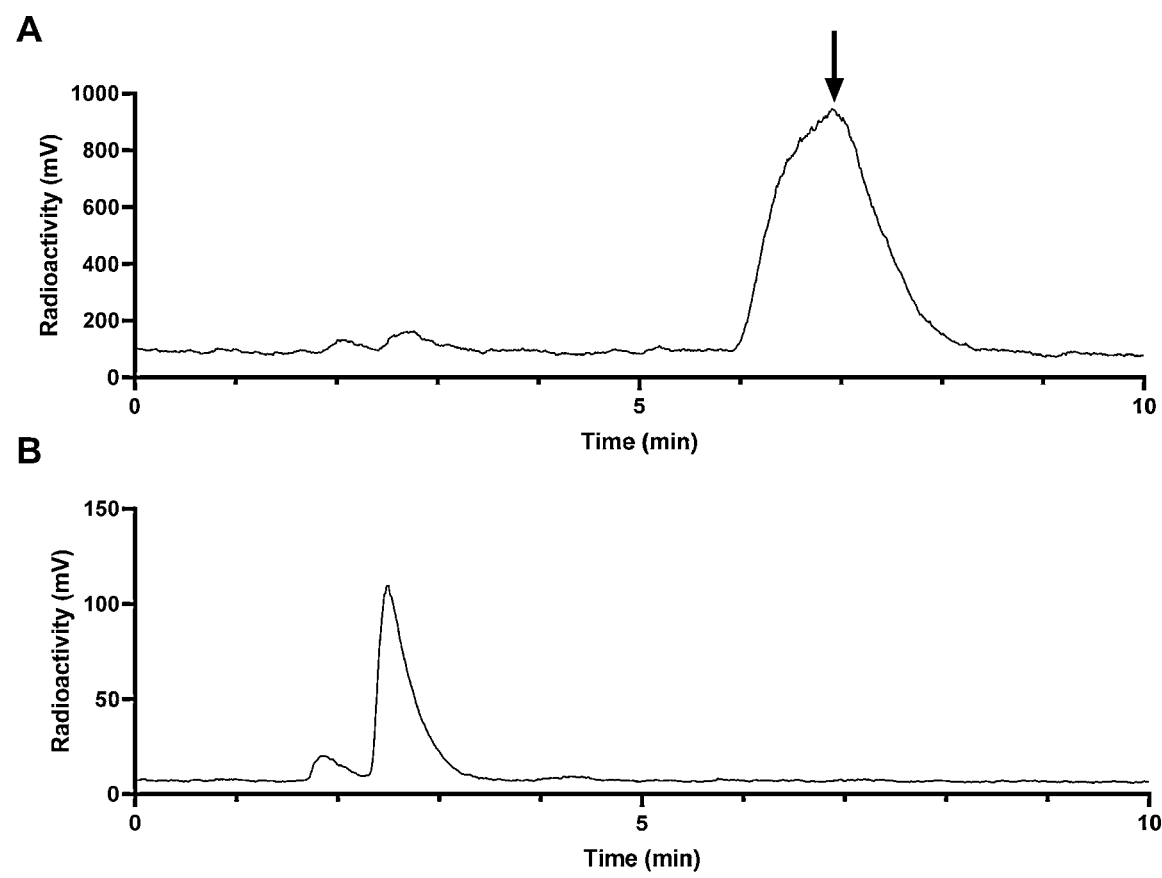
FIGS. 7A-B show representative radio-HPLC chromatograms of $^{68}$Ga-LW01142 extracted from mouse urine (FIG. 7B) and plasma samples (FIG. 7A).
Figure 8:
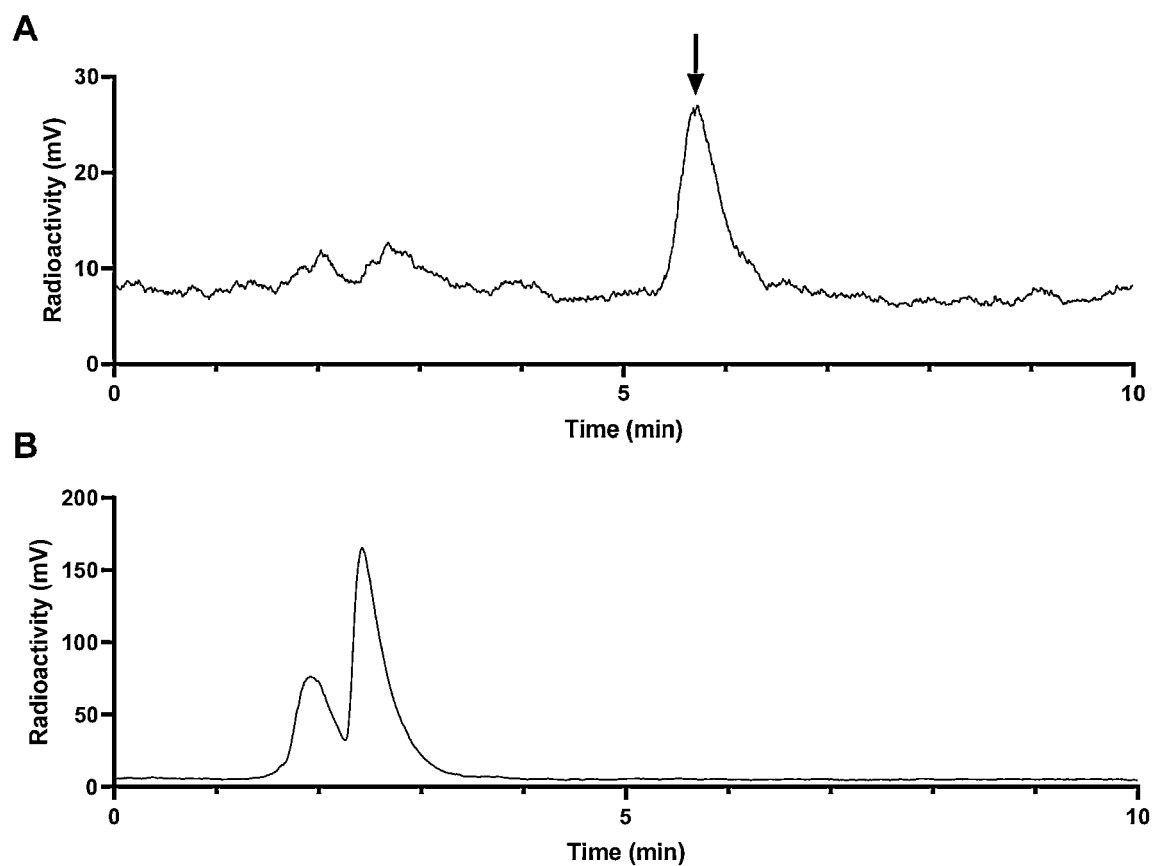
FIGS. 8A-B show representative radio-HPLC chromatograms of $^{68}$Ga-LW01102 extracted from mouse urine (FIG. 8B) and plasma samples (FIG. 8A).

As used herein, the terms "comprising," "having", "including" and "containing," and grammatical variations thereof, are inclusive or open-ended and do not exclude additional, unrecited elements and/or method steps, even if a feature/component defined as a part thereof consists or consists essentially of specified feature(s)/component(s). The term "consisting essentially of" if used herein in connection with a compound, composition, use or method, denotes that additional elements and/or method steps may be present, but that these additions do not materially affect the manner in which the recited compound, composition, method or use functions. The term "consisting of" if used herein in connection with a feature of a compound, composition, use or method, excludes the presence of additional elements and/or method steps in that feature. A compound, composition, use or method described herein as comprising certain elements and/or steps may also, in certain embodiments consist essentially of those elements and/or steps, and in other embodiments consist of those elements and/or steps, whether or not these embodiments are specifically referred to. A use or method described herein as comprising certain elements and/or steps may also, in certain embodiments consist essentially of those elements and/or steps, and in other embodiments consist of those elements and/or steps, whether or not these embodiments are specifically referred to.

A reference to an element by the indefinite article "a" does not exclude the possibility that more than one of the elements is present, unless the context clearly requires that there be one and only one of the elements. The singular forms "a", "an", and "the" include plural referents unless the context clearly dictates otherwise. The use of the word "a" or "an" when used herein in conjunction with the term "comprising" may mean "one," but it is also consistent with the meaning of "one or more," "at least one" and "one or more than one."

In this disclosure, the recitation of numerical ranges by endpoints includes all numbers subsumed within that range including all whole numbers, all integers and, where suitable, all fractional intermediates (e.g., 1 to 5 may include 1, 1.5, 2, 2.75, 3, 3.80, 4, and 5 etc.).

Unless otherwise specified, "certain embodiments", "various embodiments", "an embodiment" and similar terms includes the particular feature(s) described for that embodiment either alone or in combination with any other embodiment or embodiments described herein, whether or not the other embodiments are directly or indirectly referenced and regardless of whether the feature or embodiment is described in the context of a method, product, use, composition, compound, et cetera.

As used herein, the terms "treat", "treatment", "therapeutic" and the like includes ameliorating symptoms, reducing disease progression, improving prognosis and reducing recurrence.

As used herein, the term "diagnostic agent" includes an "imaging agent". As such, a "diagnostic radionuclide" includes radionuclides that are suitable for use in imaging agents.

The term "subject" refers to an animal (e.g. a mammal or a non-mammal animal). The subject may be a human or a non-human primate. The subject may be a laboratory mammal (e.g., mouse, rat, rabbit, hamster and the like). The subject may be an agricultural animal (e.g., equine, ovine, bovine, porcine, camelid and the like) or a domestic animal (e.g., canine, feline and the like). In some embodiments, the subject is a human.

The compounds disclosed herein may also include base-free forms, solvates, salts or pharmaceutically acceptable salts thereof. Unless otherwise specified or indicated, the compounds claimed and described herein are meant to include all racemic mixtures and all individual enantiomers or combinations thereof, whether or not they are explicitly represented herein.

The compounds disclosed herein may be shown as having one or more charged groups, may be shown with ionizable groups in an uncharged (e.g. protonated) state or may be shown without specifying formal charges. As will be appreciated by the person of skill in the art, the ionization state of certain groups within a compound (e.g. without limitation, COOH, and the like) is dependent, inter alia, on the pKa of that group and the pH at that location. For example, but without limitation, a carboxylic acid group (i.e. COOH) would be understood to usually be deprotonated (and negatively charged) at neutral pH and at most physiological pH values, unless the protonated state is stabilized.

As used herein, the terms "salt" and "solvate" have their usual meaning in chemistry. As such, when the compound is a salt or solvate, it is associated with a suitable counter-ion. It is well known in the art how to prepare salts or to exchange counter-ions. Generally, such salts can be prepared by reacting free acid forms of these compounds with a stoichiometric amount of a suitable base (e.g. without limitation, Na, Ca, Mg, or K hydroxide, carbonate, bicarbonate, or the like), or by reacting free base forms of these compounds with a stoichiometric amount of a suitable acid. Such reactions are generally carried out in water or in an organic solvent, or in a mixture of the two. Counter-ions may be changed, for example, by ion-exchange techniques such as ion-exchange chromatography. All zwitterions, salts, solvates and counter-ions are intended, unless a particular form is specifically indicated.

In certain embodiments, the salt or counter-ion may be pharmaceutically acceptable, for administration to a subject. As used herein, "pharmaceutically acceptable" means suitable for in vivo use in a subject, and is not necessarily restricted to therapeutic use, but also includes diagnostic use. More generally, with respect to any pharmaceutical composition disclosed herein, non-limiting examples of suitable excipients include any suitable buffers, stabilizing agents, salts, antioxidants, complexing agents, tonicity agents, cryoprotectants, lyoprotectants, suspending agents, emulsifying agents, antimicrobial agents, preservatives, chelating agents, binding agents, surfactants, wetting agents, non-aqueous vehicles such as fixed oils, or polymers for sustained or controlled release. See, for example, Berge et al. 1977. (J. Pharm Sci. 66:1-19), or Remington—The Science and Practice of Pharmacy, 21st edition (Gennaro et al editors. Lippincott Williams & Wilkins Philadelphia), each of which is incorporated by reference in its entirety.

As used herein, the expression "$C_n$" where n is an integer (e.g. 1, 2, 3, 4, 5, 6, 7, 8, 9, 10, 11, 12, 13, 14, 15, 16,17, 18, 19, 20, and the like) or where n is defined as a range of integers (e.g. 1-20, 1-18, 2-15, 3-20, and the like) refers to the number of carbons in a compound, R-group, L-group, or substituent, or refers to the number of carbons plus heteroatoms in a compound, R-group, L-group, or substituent. A range of integers includes all integers in the range; e.g. the range 1-20 includes the integers 1, 2, 3, 4, 5, 6, 7, 8, 9, 10, 11, 12, 13, 14, 15, 16,17, 18, 19, and 20. Unless otherwise defined, heteroatoms may include any, some or all possible heteroatoms. For example, in some embodiments, the heteroatoms may be selected from N, O, S, P and Se. In some embodiments, the heteroatoms are selected from N, S, or O. Such embodiments are non-limiting. The alternative expression "Cy-Cz", where y and z are integers (e.g. $C_3$-$C_{15}$ and the like), is equivalent to "$C_n$" where n is a range of integers from y to z.

The terms "alkyl", "alkylenyl", "alkenylenyl", and "alkynylenyl" have their usual meanings in organic chemistry. For example, an "alkyenylenyl" has at least one carbon-carbon double bond, and may have any number of carbon-carbon single bonds. Similarly, an "alkynylenyl" has at least one carbon-carbon triple bond, and may have any number of carbon-carbon single bonds. The expressions "alkylenyl, alkenylenyl and/or alkynylenyl" and "alkylenyl, alkenylenyl or alkynylenyl" are intended to be equivalent and each includes hydrocarbon chains that can have any reasonable number or combination of carbon-carbon single bonds, double bonds, and triple bonds. These hydrocarbon chains can be linear, branched, cyclic, or any combination of linear and branched, linear and cyclic, cyclic and branched, branched and cyclic, or linear, branched and cyclic. Cyclic hydrocarbons may be nonaromatic, partially aromatic, or aromatic. Unless otherwise specified, the term "cyclic" includes single rings, multiple non-fused rings, fused rings, bridged rings, and combinations thereof.

The expression "wherein any carbon . . . is optionally independently replaced by N, S, or O" and other similar expressions means that the defined hydrocarbon (e.g. "alkyl", "alkylenyl", "alkenylenyl", or "alkynylenyl") includes zero, one, more than one, or any reasonable combination of two or more heteroatoms selected from N, S, and O. The above expression therefore expands the defined hydrocarbon to additionally encompass heteroalkyls, heteroalkylenyls, heteroalkenylenyls, and heteroalkynylenyls, etc. The person of skill in the art would understand that various combinations of different heteroatoms may be used.

The expression "wherein any carbon bonded to two other carbons is optionally independently replaced by N, S, or O" and other similar expressions means that any carbon in the defined hydrocarbon bonded to two other carbons (e.g. the underlined carbon in —C—C—C—), whether those bonds are single, double, or triple bonds, may be a heteroatom, but excludes heteroatoms bonded to other heteroatoms (e.g. excludes —C—N—S—, —S—S—N—, —N—S—C—, and the like).

Various R-groups (e.g. $R^1$, $R^2$, $R^3$, etc.) and L-groups (e.g. $L^1$, $L^2$, $L^3$, etc.) are defined in this disclosure. L-groups generally refer to linkages (e.g. —S—, —NH—C(O)—, —C(O)—NH—, —N(alkyl)-C(O)—, —C(O)—N(alkyl)-, —NH—C(O)—NH—, —NH—C(S)—NH—,

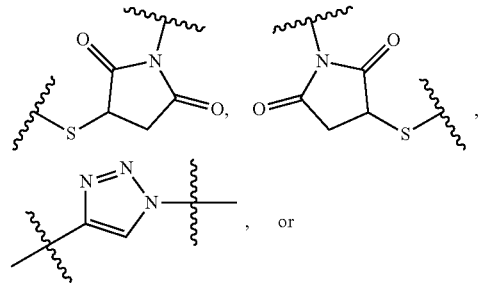

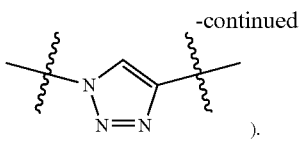
).

If unspecified, the size of an R-group or L-group is what would be considered reasonable to the person of skill in the art. For example, but without limitation, if unspecified, the size of an alkyl may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, 100 or more than 100 carbons in length, subject to the common general knowledge of the person of skill in the art. Further, but without limitation, if unspecified, the size of a heteroalkyl may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, 100 or more than 100 carbons and heteroatoms in length, subject to the common general knowledge of the person of skill in the art. In the context of the expression "alkyl, alkenyl or alkynyl" and similar expressions, the "alkyl" would be understood to be a saturated alkyl, and the "alkenyl" and the "alkynyl" would be understood to be unsaturated.

As used herein, in the context of an alkyl/heteroalkyl group of a compound, the term "linear" may be used as it is normally understood to a person of skill in the art and generally refers to a chemical entity that comprises a skeleton or main chain that does not split off into more than one contiguous chain. Non-limiting examples of linear alkyls include methyl, ethyl, n-propyl, and n-butyl.

As used herein, the term "branched" may be used as it is normally understood to a person of skill in the art and generally refers to a chemical entity that comprises a skeleton or main chain that splits off into more than one contiguous chain. The portions of the skeleton or main chain that split off in more than one direction may be linear, cyclic or any combination thereof. Non-limiting examples of a branched alkyl group include tert-butyl and isopropyl.

The term "alkylenyl" refers to a divalent analog of an alkyl group. In the context of the expression "alkylenyl, alkenylenyl and/or alkynylenyl", and similar expressions, the "alkylenyl" would be understood to be a saturated alkylenyl, and the "alkenylenyl" and the "alkynylenyl" would be understood to be unsaturated. The term "heteroalkylenyl" refers to a divalent analog of a heteroalkyl group. The term "heteroalkenylenyl" refers to a divalent analog of a heteroalkenyl group. The term "heteroalkynylenyl" refers to a divalent analog of a heteroalkynyl group.

As used herein, the term "saturated" when referring to a chemical entity may be used as it is normally understood to a person of skill in the art and generally refers to a chemical entity that comprises only single bonds, and may include linear, branched, and/or cyclic groups. Non-limiting examples of a saturated $C_1$-$C_{20}$ alkyl group may include methyl, ethyl, n-propyl, i-propyl, sec-propyl, n-butyl, i-butyl, sec-butyl, t-butyl, n-pentyl, i-pentyl, sec-pentyl, t-pentyl, n-hexyl, i-hexyl, 1,2-di methyl propyl, 2-ethylpropyl, 1-methyl-2-ethylpropyl, l-ethyl-2-methylpropyl, 1,1,2-trimethylpropyl, 1,1,2-triethylpropyl, 1,1-dimethylbutyl, 2,2-dimethylbutyl, 2-ethylbutyl, 1,3-dimethylbutyl, 2-methylpentyl, 3-methylpentyl, sec-hexyl, t-hexyl, n-heptyl, i-heptyl, sec-heptyl, t-heptyl, n-octyl, i-octyl, sec-octyl, t-octyl, n-nonyl, i-nonyl, sec-nonyl, t-nonyl, n-decyl, i-decyl, sec-decyl, t-decyl, cyclopropanyl, cyclobutanyl, cyclopentanyl, cyclohexanyl, cycloheptanyl, cyclooctanyl, cyclononanyl, cyclodecanyl, and the like. Unless otherwise specified, a $C_1$-$C_{20}$ alkylenyl therefore encompasses, without limitation, all divalent analogs of the above-listed saturated alkyl groups.

As used herein, the term "unsaturated" when referring to a chemical entity may be used as it is normally understood to a person of skill in the art and generally refers to a chemical entity that comprises at least one double or triple bond, and may include linear, branched, and/or cyclic groups. Non-limiting examples of a $C_2$-$C_{20}$ alkenyl group may include vinyl, allyl, isopropenyl, I-propene-2-yl, 1-butene-I-yl, I-butene-2-yl, I-butene-3-yl, 2-butene-1-yl, 2-butene-2-yl, octenyl, decenyl, cyclopropenyl, cyclobutenyl, cyclopentenyl, cyclohexenyl, cycloheptenyl, cyclooctenyl, cyclononanenyl, cyclodecanenyl, and the like. Unless otherwise specified, a $C_1$-$C_{20}$ alkenylenyl therefore encompasses, without limitation, all divalent analogs of the above-listed alkenyl groups. Non-limiting examples of a $C_2$-$C_{20}$ alkynyl group may include ethynyl, propynyl, butynyl, pentynyl, hexynyl, heptynyl, octynyl, nonynyl, decynyl, and the like. Unless otherwise specified, a $C_1$-$C_{20}$ alkynylenyl therefore encompasses, without limitation, all divalent analogs of the above-listed alkynyl groups.

Non-limiting examples of non-aromatic cyclic groups include cylcopropyl, cyclobutyl, cyclopentyl, cyclohexyl, and the like. Non-limiting examples of non-aromatic heterocyclic groups include aziridinyl, azetidinyl, diazetidinyl, pyrrolidinyl, pyrrolinyl, piperidinyl, piperazinyl, imidazolinyl, pyrazolidinyl, imidazolydinyl, phthalimidyl, succinimidyl, oxiranyl, tetrahydropyranyl, oxetanyl, dioxanyl, thietanyl, thiepinyl, morpholinyl, oxathiolanyl, and the like.

Unless further specified, an "aryl" group includes both single aromatic rings as well as fused rings containing at least one aromatic ring. non-limiting examples of $C_3$-$C_{20}$ aryl groups include phenyl (Ph), pentalenyl, indenyl, naphthyl and azulenyl. Non-limiting examples of aromatic heterocyclic groups of similar size include pyrrolyl, imidazolyl, pyrazolyl, pyridinyl, pyridazinyl, pyrimidinyl, pirazinyl, quinolinyl, isoquinolinyl, acridinyl, indolyl, isoindolyl, indolizinyl, purinyl, carbazolyl, indazolyl, phthalazinyl, naphthyridinyl, quinoxalinyl, quinazolinyl, cinnolinyl, pteridinyl, phenanthridinyl, phenazinyl, phenanthrolinyl, perimidinyl, furyl, dibenzofuryl, xanthenyl, benzofuryl, thiophenyl, thianthrenyl, benzothiophenyl, phosphorinyl, phosphinolinyl, phosphindolyl, thiazolyl, oxazolyl, isoxazolyl, and the like.

As used herein, the term "substituted" is used as it would normally be understood to a person of skill in the art and generally refers to a compound or chemical entity that has one chemical group replaced with a different chemical group. Unless otherwise specified, a substituted alkyl, alkylenyl, alkenylenyl, or alkynylenyl has one or more hydrogen atom(s) independently replaced with an atom that is not hydrogen. For example, chloromethyl is a non-limiting example of a substituted alkyl, more particularly an example of a substituted methyl. Aminoethyl is another non-limiting example of a substituted alkyl, more particularly an example of a substituted ethyl. Unless otherwise specified, a substituted compound or group (e.g. R-group or L-group) may be substituted with any chemical group reasonable to the person of skill in the art. For example, but without limitation, a hydrogen bonded to a carbon or heteroatom (e.g. N) may be substituted with halide (e.g. F, I, Br, Cl), amine, amide, oxo, hydroxyl, thiol, phosphate, phosphonate, sulfate, $SO_2H$, $SO_3H$, alkyls, heteroalkyls, aryl, heteroaryl, ketones, carboxaldehyde, carboxylates, carboxamides, nitriles, monohalomethyl, dihalomethyl or trihalomethyl. In som embodiments, each carbon may be independently substituted or unsubstituted with oxo, hydroxyl, sulfhydryl, amine, amide, urea, halogen, guanidino, carboxylic acid, sulfonic acid, sulfinic acid, or phosphoric acid. In some embodiments, the amide substituent is —C(O)—$NH_2$.

As used herein, the term "unsubstituted" is used as it would normally be understood to a person of skill in the art. Non-limiting examples of unsubstituted alkyls include methyl, ethyl, tert-butyl, pentyl and the like. The expression "optionally substituted" is used interchangeably with the expression "unsubstituted or substituted". The expression "optionally independently substituted" means that each location may be substituted or may not be substituted, and when substituted each substituent may be the same or different.

In the structures provided herein, hydrogen may or may not be shown. In some embodiments, hydrogens (whether shown or implicit) may be protium (i.e. $^1H$), deuterium (i.e. $^2H$) or combinations of $^1H$ and $^2H$. Methods for exchanging $^1H$ with $^2H$ are well known in the art. For solvent-exchangeable hydrogens, the exchange of $^1H$ with $^2H$ occurs readily in the presence of a suitable deuterium source, without any catalyst. The use of acid, base or metal catalysts, coupled with conditions of increased temperature and pressure, can facilitate the exchange of non-exchangeable hydrogen atoms, generally resulting in the exchange of all $^1H$ to $^2H$ in a molecule.

The term "Xaa" refers to an amino acid residue in a peptide chain or an amino acid that is otherwise part of a compound. Amino acids have both an amino group and a carboxylic acid group, either or both of which can be used for covalent attachment. In attaching to the remainder of the compound, the amino group and/or the carboxylic acid group may be converted to an amide or other structure; e.g. a carboxylic acid group of a first amino acid is converted to an amide (i.e. a peptide bond) when bonded to the amino group of a second amino acid. As such, Xaa may have the formula —N($R^a$)$R^b$C(O)—, where $R^a$ and $R^b$ are R-groups. $R^a$ will typically be hydrogen or alkyl (e.g. methyl) or $R^a$ and $R^b$ may form a cyclic structure. The amino acid residues of a peptide may comprise typical peptide (amide) bonds and may further comprise bonds between side chain functional groups and the side chain or main chain functional group of another amino acid. For example, the side chain carboxylate of one amino acid residue in the peptide (e.g. Asp, Glu, etc.) may be bonded to and the amine of another amino acid residue in the peptide (e.g. Dap, Dab, Orn, Lys). Further details are provided below. Unless otherwise indicated, "Xaa" may be any amino acid, including a proteinogenic or nonproteinogenic amino acid. Non-limiting examples of nonproteinogenic amino acids are shown in Table 1 and include: D-amino acids (including without limitation any D-form of the following amino acids), ornithine (Orn), 3-(1-naphtyl)alanine (Nal), 3-(2-naphtyl)alanine (2-Nal), α-aminobutyric acid, norvaline, norleucine (Nle), homonorleucine, beta-(1,2,3-triazol-4-yl)-L-alanine, 1,2,4-triazole-3-alanine, Phe(4-F), Phe(4-Cl), Phe(4-Br), Phe(4-I), Phe(4-$NH_2$), Phe(4-$NO_2$), homoarginine (hArg), 2-amino-4-guanidinobutyric acid (Agb), 2-amino-3-guanidinopropionic acid (Agp), B-alanine, 4-aminobutyric acid, 5-aminovaleric acid, 6-aminohexanoic acid, 7-aminoheptanoic acid, 8-aminooctanoic acid, 9-aminononanoic acid, 10-aminodecanoic acid, 2-aminooctanoic acid, 2-amino-3-(anthracen-2-yl)propanoic acid, 2-amino-3-(anthracen-9-yl) propanoic acid, 2-amino-3-(pyren-1-yl)propanoic acid, Trp(5-Br), Trp(5-$OCH_3$), Trp(6-F), Trp(5-OH) or Trp(CHO), 2-aminoadipic acid (2-Aad), 3-aminoadipic acid (3-Aad), propargylglycine (Pra), homopropargylglycine (Hpg), beta-homopropargylglycine (Bpg), 2,3-diaminopropionic acid (Dap), 2,4-diaminobutyric acid (Dab), azidolysine (Lys($N_3$)), azido-ornithine (Orn($N_3$)), 2-amino-4-azidobutanoic acid Dab($N_3$), Dap(N 3), 2-(5'-azidopentyl)alanine, 2-(6'-azidohexyl)alanine, 4-amino-1-carboxymethyl-piperidine (Pip), 4-(2-aminoethyl)-1-carboxymethyl-piperazine (Acp), tranexamic acid, tert-leucine (Tle), 4-chlorophenylalanine (Cpa), thiazoline-4-carboxylic acid (Thz), αMe-Trp, p-aminomethylaniline-diglycolic acid (pABzA-DIG), 4-amino-1-carboxymethyl-piperidine (Pip), $NH_2(CH_2)_2O(CH_2)_2C(O)OH$, $NH_2(CH_2)_2[O(CH_2)_2]_2C(O)OH$ (dPEG2), $NH_2(CH_2)_2[O(CH_2)_2]_3C(O)OH$, $NH_2(CH_2)_2[O(CH_2)_2]_4C(O)OH$, $NH_2(CH_2)_2[O(CH_2)_2]_5C(O)OH$, $NH_2(CH_2)_2[O(CH_2)_2]_6C(O)OH$, oxazolidine-4-carboxylic acid (4-oxa-L-Pro), β-(3-benzothienyl)alanine (Bta), citrulline (Cit), Trp(Me), Trp (7-Me), Trp(6-Me), Trp(5-Me), Trp(4-Me), Trp(2-Me), Trp(7-F), Trp (5-F), Trp(4-F) or cyclopentylglycine (Cpa). If not specified as an L- or D-amino acid, an amino acid shall be understood to be an L-amino acid.

TABLE 1

List of non-limiting examples of non-proteinogenic amino acids.

| | |
|---|---|
| p-aminomethylaniline-diglycolic acid (pABzA-DIG) | 2-amino-3-(anthracen-2-yl)propanoic acid |
| ornithine (Orn) | 2-amino-3-(anthracen-9-yl)propanoic acid |
| 3-(1-naphtyl)alanine (Nal) | 2-amino-3-(pyren-1-yl)propanoic acid |
| 3-(2-naphtyl)alanine (2-Nal) | Trp(5-Br), |
| α-aminobutyric acid | Trp(5-$OCH_3$), |
| norvaline | Trp(6-F) |
| norleucine (Nle) | Trp(5-OH) |
| homonorleucine | Trp(CHO) |
| beta-(1,2,3-triazol-4-yl)-L-alanine | $N^\varepsilon,N^\varepsilon,N^\varepsilon$-trimethyl-lysine |
| 1,2,4-triazole-3-alanine | cysteic acid |
| Phe(4-F), Phe(2-F), Phe(3-F), | 2-aminoadipic acid (2-Aad) |
| Phe(4-Cl), Phe(2-Cl), Phe(3-Cl), | 3-aminoadipic acid (3-Aad) |
| Phe(4-Br), Phe(2-Br), Phe(3-Br), | propargylglycine (Pra) |
| Phe(4-I), Phe(2-I), Phe(2-I), | homopropargylglycine (Hpg) |
| Phe(4-$NH_2$), Phe(2-$NH_2$), Phe(3-$NH_2$), | beta-homopropargylglycine (Bpg) |
| Phe(4-$NO_2$), Phe(2-$NO_2$), Phe(2-$NO_2$), | 2,3-diaminopropionic acid (Dap) |

TABLE 1-continued

List of non-limiting examples of non-proteinogenic amino acids.

| | |
|---|---|
| homoarginine (hArg) | 2,4-diaminobutyric acid (Dab) |
| 4-(2-aminoethyl)-1-carboxymethyl-piperazine (Acp) | azidolysine (Lys($N_3$)) |
| 2-(5'-azidopentyl)alanine, 2-(6'-azidohexyl)alanine | azido-ornithine (Orn($N_3$)) |
| 2-amino-4-guanidinobutyric acid (Agb) | amino-4-azidobutanoic acid Dab($N_3$) |
| 2-amino-3-guanidinopropionic acid (Agp) | tranexamic acid |
| β-alanine | 4-amino-1-carboxymethyl-piperidine (Pip) |
| 4-aminobutyric acid | $NH_2(CH_2)_2O(CH_2)_2C(O)OH$ |
| 5-aminovaleric acid | $NH_2(CH_2)_2[O(CH_2)_2]_2C(O)OH$ (dPEG2) |
| 6-aminohexanoic acid | $NH_2(CH_2)_2[O(CH_2)_2]_3C(O)OH$ |
| 7-aminoheptanoic acid | $NH_2(CH_2)_2[O(CH_2)_2]_4C(O)OH$ |
| 8-aminooctanoic acid | $NH_2(CH_2)_2[O(CH_2)_2]_5C(O)OH$ |
| 9-aminononanoic acid | $NH_2(CH_2)_2[O(CH_2)_2]_6C(O)OH$ |
| 10-aminodecanoic acid | citrulline (Cit) |
| 2-aminooctanoic acid | β-(3-benzothienyl)alanine (Bta) |
| tert-leucine (Tle) | oxazolidine-4-carboxylic acid (4-oxa-L-Pro) |
| 4-chlorophenylalanine (Cpa) | cyclopentylglycine (Cpg) |
| thiazoline-4-carboxylic acid (Thz) | any N-methylated version of a proteinogenic amino acid or non-proteinogenic amino acid in this Table |
| αMe-Trp | any D-amino acid of a proteinogenic amino acid or any D-amino acid of a non-proteinogrenic amino acid in this Table |
| Trp(Me) | Trp(7-Me) |
| Trp(6-Me) | Trp(5-Me) |
| Trp(4-Me) | Trp(2-Me) |
| Trp(7-F) | Trp(5-F) |
| Tpi(2,3,4,9-tetrahydro-1H-pyrido[3,4-b]indol-3-carboxylic acid) | cyclobutylglycine |
| Trp(4-F) | 5,5-dimethyl-1,3-thiazolidine-4-carboxylic acid ($Me_2Thz$) |
| 7-Aza (7-azatryptophan) | 2,3-dehyrdo-Val cyclopropylglycine |

The wavy line " " symbol shown through or at the end of a bond in a chemical formula (e.g. in the definitions $L^1$ or $R^{alb}$ of Formula I) is intended to define the group on one side of the wavy line, without modifying the definition of the structure on the opposite side of the wavy line. Where an R-group or L-group is bonded on two or more sides, any atoms shown outside the wavy lines are intended to clarify orientation of the defined group. As such, only the atoms between the two wavy lines constitute the definition of the R-group or L-group. When atoms are not shown outside the wavy lines (e.g. $L^1$), or for a chemical group shown without wavy lines but does have bonds on multiple sides (e.g. —C(O)NH—, and the like), the chemical group should be read from left to right matching the orientation in the formula that the group relates to; e.g. for formula -$R^a$-$R^b$-$R^c$-, the definition of $R^b$ as —C(O)NH— would be incorporated into the formula as -$R^a$—C(O)NH—$R^c$— not as -$R^a$—NHC(O)—$R^2$—.

In various aspects, there is disclosed a peptidic compound, wherein the compound has the structure of Formula I or is a salt or solvate of Formula I defined as follows:

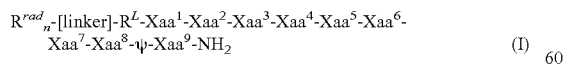

$R^{rad}{}_n$-[linker]-$R^L$-$Xaa^1$-$Xaa^2$-$Xaa^3$-$Xaa^4$-$Xaa^5$-$Xaa^6$-$Xaa^7$-$Xaa^8$-ψ-$Xaa^9$-$NH_2$ (I)

wherein:
$Xaa^1$ is an N-terminal amino acid residue selected from D-Phe, Cpa (4-chlorophenylalanine), D-Cpa, Nal (3-(1-naphthyl)alanine), D-Nal, 2-Nal (3-(2-naphthyl)alanine), or D-2-Nal;
$Xaa^2$ is Asn, Gln, homoserine (Hse), citrulline (Cit) or His;
$Xaa^3$ is Trp, 8-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(5-OH) or αMe-Trp;
$Xaa^4$ is Ala or Ser;
$Xaa^5$ is Val, Cpg (cyclopentylglycine) or tert-leucine (Tle);
$Xaa^6$ is Gly, NMe-Gly, or D-Ala;
$Xaa^7$ is His or NMe-His;
$Xaa^8$ is Leu, D-Pro, or Phe;
$Xaa^9$-$NH_2$ is a C-terminally amidated amino acid residue selected from Pro, Phe, 4-oxa-L-Pro (oxazolidine-4-carboxylic acid), $Me_2Thz$ (5,5-dimethyl-1,3-thiazolidine-4-carboxylic acid), or Thz (thiazoline-4-carboxylic acid);
ψ is a peptide bond or reduced peptide bond between $Xaa^8$ and $Xaa^9$;
excluding compounds in which $Xaa^2$, $Xaa^3$, $Xaa^5$, and $Xaa^7$ are Gln, Trp, Val, and His, respectively, in which ψ is a reduced peptide bond;
$R^L$ is —C(O)—, —NH—C(O)—, or —NH—C(S)—;
the linker is a linear or branched chain of n1 units of —$L^1R^1$— and/or —($L^1)_2R^1$—, wherein:
n1 is 1-20;
each $R^1$ is, independently, a linear, branched, and/or cyclic $C_{n2}$ alkylenyl, alkenylenyl and/or alkynylenyl, wherein each n2 is independently 1-20, wherein any carbon bonded to two other carbons is optionally independently replaced by N, S, or O, and carbons are optionally independently substituted with oxo, hydroxyl, sulfhydryl, -SeH, halogen, guanidino, amine, amide, urea, carboxylic acid, sulfonic acid, sulfinic acid, or phosphoric acid;

L¹ bonds to carbon, wherein each L¹ is independently —S—, —N(R²)C(O)—, —C(O)N(R²)—, —NH—C(O)—NH—, —NH—C(S)—NH—,

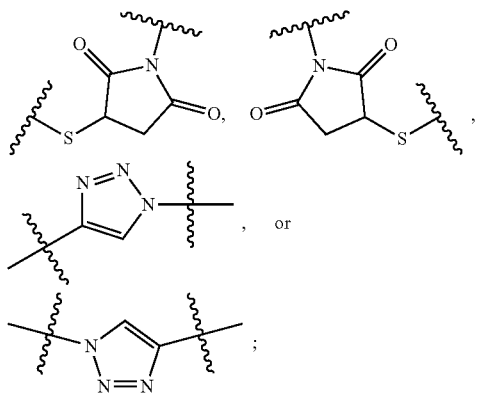

or and

R² is H, methyl or ethyl; and an albumin binder ($R^{alb}$) is optionally bonded to an L¹ of the linker, wherein the albumin binder is:
—$(CH_2)_{n3}$—$CH_3$ wherein n3 is 8-20;
—$(CH_2)_{n4}$—C(O)OH wherein n4 is 8-20;

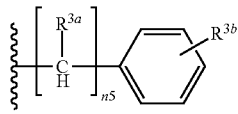

wherein n5 is 1-4 and $R^{3a}$ is H or methyl, and $R^{3b}$ is I, Br, F, Cl, H, OH, $OCH_3$, $NH_2$, $NO_2$ or $C_1$-$C_6$ alkyl; or

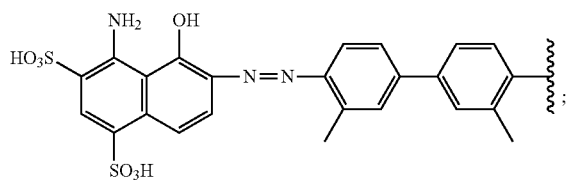

n6 is 1-5; and each $R^{rad}$ is a radiolabeling group bonded to or incorporating an L¹ of the linker, wherein each radiolabeling group is independently: a radiometal chelator; an aryl or heteroaryl substituted with a radiohalogen; a prosthetic group containing a trifluoroborate; a prosthetic group containing a silicon-fluorine-acceptor moiety; or a prosthetic group containing a fluorophosphate, fluorosulfate, sulfonyl fluoride, or a combination thereof.

In another embodiment, the peptidic compound may be a compound with the structure of Formula A or is a salt or solvate of Formula A as follows:

$R^{rad}_{n6}$-[linker]-$R^L$-$Xaa^1$-$Xaa^2$-$Xaa^3$-$Xaa^4$-$Xaa^5$-$Xaa^6$-$Xaa^7$-$Xaa^8$-ψ-$Xaa^9$-$NH_2$ (Formula A), wherein:

$Xaa^1$ is an N-terminal amino acid residue selected from D-Phe, 4-chlorophenylalanine (Cpa), D-Cpa, 3-(1-naphthyl)alanine (Nal), D-Tpi, D-Nal, 3-(2-naphthyl)alanine (2-Nal), or D-2-Nal;

$Xaa^2$ is Asn, Gln, homoserine (Hse), citrulline (Cit) or His;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(5-OH), Tpi, 7-Aza, or αMe-Trp;

$Xaa^4$ is Ala or Ser;

$Xaa^5$ is Val, 2,3-dehydro-Val, Cpg (cyclopentylglycine), cyclopropylglycine, cyclobutylglycine, or tert-leucine (Tle);

$Xaa^6$ is Gly, NMe-Gly, or D-Ala;

$Xaa^7$ is His or NMe-His;

$Xaa^8$ is Leu, D-Pro, or Phe;

$Xaa^9$-$NH_2$ is a C-terminally amidated amino acid residue selected from Pro, Phe, oxazolidine-4-carboxylic acid (4-oxa-L-Pro), $Me_2$Thz (5,5-dimethyl-1,3-thiazolidine-4-carboxylic acid), or thiazoline-4-carboxylic acid (Thz);

ψ represents a peptide bond or reduced peptide bond joining $Xaa^8$ to $Xaa^9$; excluding compounds in which $Xaa^2$, $Xaa^3$, $Xaa^6$, and $Xaa^7$ are Gln, Trp, Val, and His, respectively, in which ψ is a reduced peptide bond; $R^L$ is —C(O)—, —NH—C(O)—, or —NH—C(S)—;

the linker is a linear or branched chain of n1 units of -$L^1R^1$- and/or -$(L^1)_2R^1$-, wherein:

n1 is 1-20; each $R^1$ is, independently, a linear, branched, and/or cyclic $C_{n2}$ alkylenyl, alkenylenyl and/or alkynylenyl, wherein each n2 is independently 1-20, wherein any carbon bonded to two other carbons is optionally independently replaced by N, S, or O, and carbons are optionally independently substituted with oxo, hydroxyl, sulfhydryl, —SeH, halogen, guanidino, amine, amide, urea, carboxylic acid, sulfonic acid, sulfinic acid, or phosphoric acid;

L¹ bonds to carbon, wherein each L¹ is independently —S—, —N(R²)C(O)—, —C(O)N(R²)—, —NH—C(O)—NH—, —NH—C(S)—NH—,

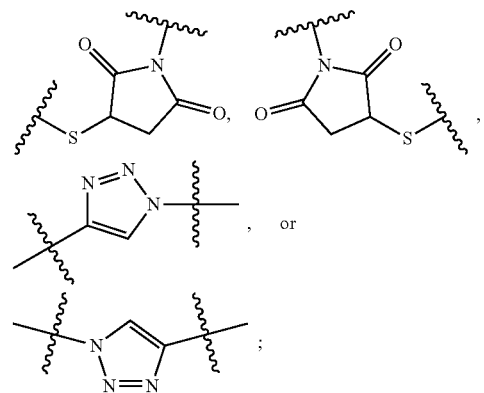

and R² is H, methyl or ethyl; and an albumin binder ($R^{alb}$) is optionally bonded to an L¹ of the linker, wherein the albumin binder is: —$(CH_2)_{n3}$—$CH_3$ wherein n3 is 8-20; —$(CH_2)_{n4}$—C(O)OH wherein n4 is 8-20;

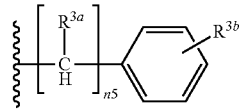

wherein n5 is 1-4 and $R^{3a}$ is H or methyl, and $R^{3b}$ is I, Br, F, Cl, H, OH, $OCH_3$, $NH_2$, $NO_2$ or $C_1$-$C_6$ alkyl; or

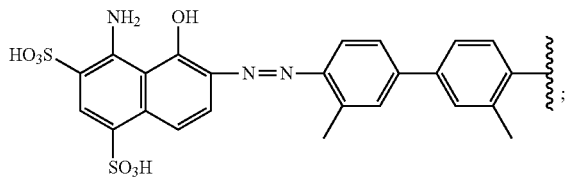

n6 is 1-5; and each $R^{rad}$ is a radiolabeling group bonded to or incorporating an $L^1$ of the linker, wherein each radiolabeling group is independently: a radiometal chelator; an aryl or heteroaryl substituted with a radiohalogen; a prosthetic group containing a trifluoroborate; a prosthetic group containing a silicon-fluorine-acceptor moiety; or a prosthetic group containing a fluorophosphate, fluorosulfate, sulfonyl fluoride, or a combination thereof.

In another embodiment, the invention may include a peptidic compound where $Xaa^1$ is an N-terminal amino acid residue selected from D-Phe, 4-chlorophenylalanine (Cpa), D-Cpa, 3-(1-naphthyl)alanine (Nal), D-Nal, 3-(2-naphthyl) alanine (2-Nal), or D-2-Nal; $Xaa^3$ is Trp, β-(3-benzothienyl) alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(5-OH), or αMe-Trp; and $Xaa^5$ is Val, Cpg (cyclopentylglycine), or tert-leucine (Tle).

In another specific embodiment, $Xaa^1$ is an N-terminal amino acid residue selected from D-Phe, or D-2-Nal. In another specific embodiment, $Xaa^2$ is Gln, or His. In another specific embodiment, $Xaa^5$ is Val, or tert-leucine (Tle). In another specific embodiment, $Xaa^6$ is Gly, or NMe-Gly. In another specific embodiment, $Xaa^9$-$NH_2$ is a C-terminally amidated amino acid residue selected from Pro or thiazoline-4-carboxylic acid (Thz). In another specific embodiment, $Xaa^1$ is an N-terminal amino acid residue selected from D-Phe, or D-2-Nal; $Xaa^2$ is Gln, or His; $Xaa^4$ is Ala; $Xaa^5$ is Val, or tert-leucine (Tle); $Xaa^6$ is Gly, or NMe-Gly; $Xaa^8$ is Leu; and $Xaa^9$-$NH_2$ is a C-terminally amidated amino acid residue selected from Pro or thiazoline-4-carboxylic acid (Thz).

In another specific embodiment, $Xaa^3$ is β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(5-OH), Tpi, 7-Aza, or αMe-Trp. In another specific embodiment, ψ is a peptide bond. In another specific embodiment, $Xaa^9$ is Thz. In another specific embodiment, $Xaa^2$ is His. In another specific embodiment, wherein $Xaa^3$ is Trp. In another specific embodiment, $Xaa^5$ is Tle. In another specific embodiment, $Xaa^7$ is NMe-His.

In another specific embodiment of the peptidic compounds described herein, ψ is a peptide bond; $Xaa^9$ is Thz; $Xaa^2$ is His; $Xaa^3$ is Trp; $Xaa^5$ is Tle; and $Xaa^7$ is NMe-His.

In another embodiment, $Xaa^3$ is αMe-Trp. In another embodiment, $Xaa^6$ is Gly. In another embodiment, $Xaa^8$ is Leu.

In another embodiment, at least one of $Xaa^1$, $Xaa^2$, $Xaa^3$, $Xaa^4$, $Xaa^5$, $Xaa^6$, $Xaa^7$, $Xaa^8$, or $Xaa^9$ is methylated.

In another embodiment, the peptidic compounds of the present invention may have the structure of Formula B or is a salt or solvate of Formula B, wherein Formula B is as follows:

$R^{rad}_{n6}$-[linker]-$R^L$-$Xaa^1$-$Xaa^2$-$Xaa^3$-$Xaa^4$-$Xaa^5$-$Xaa^6$-$Xaa^7$-$Xaa^8$-ψ-$Xaa^9$-$NH_2$ (Formula B)

wherein:
$Xaa^1$ is an N-terminal amino acid residue selected from D-Phe, 4-chlorophenylalanine (Cpa), D-Cpa, 3-(1-naphthyl)alanine (Nal), D-Tpi, D-Nal, 3-(2-naphthyl) alanine (2-Nal), or D-2-Nal;
$Xaa^2$ is Asn, Gln, homoserine (Hse), citrulline (Cit) or His;
$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(5-OH), Tpi, 7-Aza, or αMe-Trp;
$Xaa^4$ is Ala or Ser;
$Xaa^5$ is Val, 2,3-dehydro-Val, Cpg (cyclopentylglycine), cyclopropylglycine, cyclobuylglycine, or tert-leucine (Tle);
$Xaa^6$ is Gly, NMe-Gly, or D-Ala;
$Xaa^7$ is His or NMe-His;
$Xaa^8$ is Leu, D-Pro, or Phe;
$Xaa^9$-$NH_2$ is a C-terminally amidated amino acid residue selected from Pro, oxazolidine-4-carboxylic acid (4-oxa-L-Pro), $Me_2$Thz (5,5-dimethyl-1,3-thiazolidine-4-carboxylic acid), or thiazoline-4-carboxylic acid (Thz);
ψ represents a peptide bond or reduced peptide bond joining $Xaa^8$ to $Xaa^9$;
$R^L$ is —C(O)—, —NH—C(O)—, or —NH—C(S)—;
the linker is a linear or branched chain of n1 units of -$L^1R^1$- and/or -$(L^1)_2R^1$-, wherein:
n1 is 1-20;
each $R^1$ is, independently, a linear, branched, and/or cyclic $C_{n2}$ alkylenyl, alkenylenyl and/or alkynylenyl, wherein each n2 is independently 1-20, wherein any carbon bonded to two other carbons is optionally independently replaced by N, S, or O, and carbons are optionally independently substituted with oxo, hydroxyl, sulfhydryl, —SeH, halogen, guanidino, amine, amide, urea, carboxylic acid, sulfonic acid, sulfinic acid, or phosphoric acid;
$L^1$ bonds to carbon, wherein each $L^1$ is independently —S—, —N($R^2$)C(O)—, —C(O)N($R^2$)—, —NH—C(O)—NH—, —NH—C(S)—NH—,

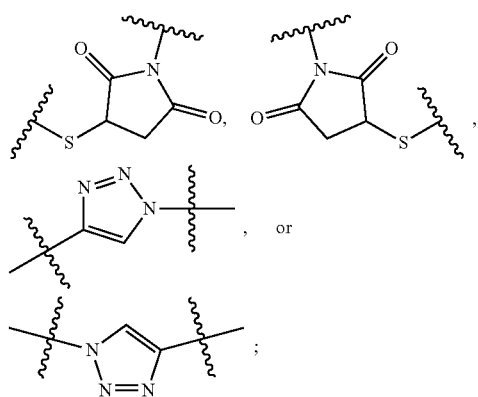

and
$R^2$ is H, methyl or ethyl; and
an albumin binder ($R^{alb}$) is optionally bonded to an $L^1$ of the linker, wherein the albumin binder is:
—$(CH_2)_{n3}$-$CH_3$ wherein n3 is 8-20;
—$(CH_2)_{n4}$—C(O)OH wherein n4 is 8-20;

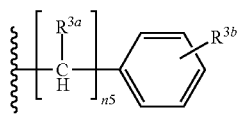

wherein n5 is 1-4 and $R^{3a}$ is H or methyl, and $R^{3b}$ is I, Br, F, Cl, H, OH, OCH$_3$, NH$_2$, NO$_2$ or $C_1$-$C_6$ alkyl; or

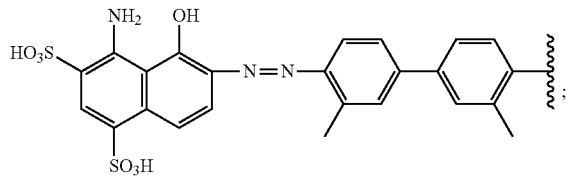 [SMILES: *c1ccc(-c2ccc(N=Nc3ccc4c(S(=O)(=O)O)cc(S(=O)(=O)O)c(N)c4c3O)c(C)c2)cc1C]

n6 is 1-5; and each $R^{rad}$ is a radiolabeling group bonded to or incorporating an $L^1$ of the linker, wherein each radiolabeling group is independently: a radiometal chelator; an aryl or heteroaryl substituted with a radiohalogen; a prosthetic group containing a trifluoroborate; a prosthetic group containing a silicon-fluorine-acceptor moiety; or a prosthetic group containing a fluorophosphate, fluorosulfate, sulfonyl fluoride, or a combination thereof.

In a specific embodiment, the compounds of Formulas I, A, or B do not comprise the albumin binder $R^{alb}$ in the linker.

In a specific embodiment, at least one of Xaa$^1$, Xaa$^2$, Xaa$^3$, Xaa$^4$, Xaa$^5$, Xaa$^6$, Xaa$^7$, Xaa$^8$, or Xaa$^9$ is methylated. In another specific embodiment, ψ is a reduced peptide bond joining Xaa$^8$ to Xaa$^9$. In another specific embodiment, Xaa$^1$ is D-Phe; and/or Xaa$^6$ is Gly; and/or Xaa$^8$ is Leu; and/or Xaa$^9$ is Pro, Thz or 4-oxa-L-Pro. In another specific embodiment, Xaa$^6$ is Gly or N-methyl-Gly. In another specific embodiment, Xaa$^9$ is Thz. In another specific embodiment, Xaa$^9$ is Pro. In another embodiment, Xaa$^1$ is D-phe, Xaa$^2$ is Gln, Xaa$^3$ is Trp, Xaa$^4$ is Ala, Xaa$^5$ is Val, Xaa$^6$ Xaa$^6$ is Gly or N-methyl-Gly, Xaa$^7$ is His, Xaa$^8$ is Leu, Xaa$^9$ is Thz, and ψ is a reduced peptide bond joining Xaa$^8$ to Xaa$^9$. In another specific embodiment, Xaa$^6$ is N-methyl-Gly.

In another specific embodiment, the peptidic compound is any compound from Formula I, A, or B, wherein the compounds described in PCT application publication WO2009/109332, which is incorporated by reference in its entirety herein, are excluded. In a specific embodiment, the peptidic compound is any compound from Formula B, wherein the compounds described in PCT application publication WO2009/109332, which is incorporated by reference in its entirety herein, are excluded. In another specific embodiment, the peptidic compound is any compound from Formula I, A, or B, wherein the compounds described in PCT application publication WO2021/068051, which is incorporated by reference in its entirety herein, are excluded. In a specific embodiment, the peptidic compound is any compound from Formula B, wherein the compounds described in PCT application publication WO2021/068051, which is incorporated by reference in its entirety herein, are excluded.

In a specific embodiment, the peptidic compound is any compound described in PCT application publication WO2021/068051, which is incorporated by reference in its entirety herein.

In a specific embodiment, the peptidic compound is any compound from Formula B, wherein the compounds described in Wang, L et al., Molecules, 2022 27, 3777, which is incorporated by reference in its entirety herein, are excluded.

In a specific embodiment, the peptidic compound is any compound described in Wang, L et al., Molecules, 2022 27, 3777, which is incorporated by reference in its entirety herein.

In another specific embodiment, peptidic compounds of Formula I, A, or B exclude $R^{rad}_{n6}$-[linker]-$R^L$-, or $R^{rad}_{n6}$, or [linker] or $R^L$-.

In another specific embodiment of the peptidic compounds described herein, the radiometal, the radionuclide-bound metal, or the radionuclide-bound metal-containing prosthetic group is: $^{68}$Ga, $^{61}$Cu, $^{64}$CU, $^{67}$Ga, $^{99m}$TC, $^{110m}$In, $^{111}$In, $^{44}$Sc, $^{86}$Y, $^{89}$Zr, $^{90}$Nb, $^{152}$Tb, $^{155}$Tb, [$^{18}$F]AlF, $^{131}$I, $^{123}$I, $^{124}$I, and $^{203}$Pb, $^{72}$As.

In another specific embodiment of the peptidic compounds described herein, the radiometal, the radionuclide-bound metal, or the radionuclide-bound metal-containing prosthetic group is: $^{165}$Er, $^{212}$Bi, $^{211}$At, $^{166}$Ho, $^{149}$Pm, $^{159}$Gd, $^{105}$Rh, $^{109}$Pd, $^{198}$Au, $^{199}$Au, $^{175}$Yb, $^{142}$Pr, $^{177}$Lu, $^{111}$In, $^{213}$Bi, $^{47}$Sb, $^{90}$Y, $^{225}$Ac, $^{117m}$Sn, $^{153}$Sm, $^{149}$Tb, $^{161}$Tb, $^{224}$Ra, $^{223}$Ra, $^{212}$Pb, $^{227}$Th, $^{223}$Ra, $^{77}$As, $^{186}$Re, $^{188}$Re, $^{67}$Cu, or $^{64}$Cu.

In another specific embodiment, the compounds or peptidic compounds may be included in a pharmaceutical composition. In a specific embodiment, the pharmaceutical composition may include one or more compounds from Formula I, A, or B and a pharmaceutically acceptable carrier. In another specific embodiment, the peptidic compound(s) may be bound to or include a radiometal. In a specific embodiment, the radiometal is $^{165}$Er, $^{212}$Bi, $^{211}$At, $^{166}$Ho, $^{149}$Pm, $^{159}$Gd, $^{105}$Rh, $^{109}$Pd, $^{198}$Au, $^{199}$Au, $^{175}$Yb, $^{142}$Pr, $^{177}$Lu, $^{111}$In, $^{213}$Bi, $^{47}$Sb, $^{90}$Y, $^{225}$Ac, $^{117}$Sn, $^{153}$Sm, $^{149}$Tb, $^{161}$Tb, $^{224}$Ra, $^{223}$Ra, $^{212}$Pb, $^{227}$Th, $^{223}$Ra, $^{77}$As, $^{186}$Re, $^{188}$Re, $^{67}$Cu, or $^{64}$Cu.

In another embodiment, the invention may include using the peptidic compounds described herein for imaging methods. In a specific embodiment, the methods may include imaging Gastrin-releasing peptide receptor (GRPR) in a subject, the method comprising: administering to the subject a peptidic compound of any one of Formulas I, A or B; and imaging tissue of the subject. In a specific embodiment, the methods may include the methods of treating cancer in a subject comprising, administering to the subject in need thereof a peptidic compound of any one of Formulas I, A or B and a pharmaceutically acceptable excipient.

In another specific embodiment, the methods may include treating a GRPR-expressing condition or disease. In a specific embodiment, the GRPR-expressing condition or disease may be a psychiatric disorder, neurological disorder, inflammatory disease, prostate cancer, lung cancer, head and neck cancer, colon cancer, kidney cancer, ovarian cancer, liver cancer, pancreatic cancer, breast cancer, glioma or neuroblastoma. In some embodiments, the cancer is prostate cancer.

As described herein, the peptidic moiety -Xaa$^1$-Xaa$^2$-Xaa$^3$-Xaa$^4$-Xaa$^5$-Xaa$^6$-Xaa$^7$-Xaa$^8$-ψ-Xaa$^9$-NH$_2$ is the GRPR-targeting moiety of the compound; i.e. it is capable of specifically binding GRPR and potentially producing antagonist effects.

In some embodiments, Xaa$^1$ is D-Phe. In other embodiments, Xaa$^1$ is Cpa. In other embodiments, Xaa$^1$ is D-Cpa. In other embodiments, Xaa$^1$ is Nal. In other embodiments, Xaa$^1$ is D-Nal. In other embodiments, Xaa$^1$ is 2-Nal. In other embodiments, Xaa$^1$ is D-2-Nal. D-Phe at position Xaa$^1$ has been reported to retain binding affinity for GRPR (e.g. see: Lau, et al., 2019, ACS Omega 4:1470-1478). D-Cpa, Tpi, D-Tpi and D-Nal at position Xaa$^1$ have been reported to retain strong binding affinity for GRPR (e.g. see: Tables 1 and 3 in Cai et al., 1994 *Proc. Natl. Acad. Sci. USA* 91:12664-12668; RC-3965-II disclosed in Reile et al., 1995 *International Journal of Oncology* 7:749-754). Since both L-Tpi and D-Tpi retain binding affinity, the L-isomers of D-Nal and D-Cpa would also retain strong binding affinity for GRPR.

In some embodiments, Xaa$^2$ is Asn. In other embodiments, Xaa$^2$ is Gln. In other embodiments, Xaa$^2$ is Hse. In other embodiments, Xaa$^2$ is Cit. In other embodiments, Xaa$^2$ is His. Gln at position Xaa$^2$ is found in wildtype BBN. His at position Xaa$^2$ is found in wildtype GRP. Hse and Cit at position Xaa$^2$ have been reported to retain binding affinity for GRPR (see Gunther, et al., 2021, J Nucl Med. 62 (supplement 1) 1474).

In some embodiments, Xaa$^3$ is Trp. In other embodiments, Xaa$^3$ is Bta. In other embodiments, Xaa$^3$ is αMe-Trp. In other embodiments, Xaa$^3$ is Trp(Me). In other embodiments, Xaa$^3$ is Trp(7-Me). In other embodiments, Xaa$^3$ is Trp(6-Me). In other embodiments, Xaa$^3$ is Trp(5-Me). In other embodiments, Xaa$^3$ is Trp(4-Me). In other embodiments, Xaa$^3$ is Trp(2-Me). In other embodiments, Xaa$^3$ is Trp(7-F). In other embodiments, Xaa$^3$ is Trp(6-F). In other embodiments, Xaa$^3$ is Trp(5-F). In other embodiments, Xaa$^3$ is Trp(4-F). In other embodiments, Xaa$^3$ is Trp(5-OH). Trp at position Xaa$^3$ is found in wildtype BBN and GRP. Bta and αMe-Trp at position Xaa$^3$ have been reported to retain binding affinity for GRPR (see Gunther, et al., 2021, Journal of Nuclear Medicine 62 (supplement 1) 1474; Gunther, et al., J Nucl Med. 2022, jnumed.121.263323; DOI: https://doi.org/10.2967/jnumed.121.263323).

In some embodiments, Xaa$^4$ is Ala. In other embodiments, Xaa$^4$ is Ser.

In some embodiments, Xaa$^5$ is Val. In other embodiments, Xaa$^5$ is Cpg. In other embodiments, Xaa$^5$ is Tle. Val in position Xaa$^5$ is found in wildtype BBN and GRP.

In some embodiments, Xaa$^6$ is Gly. In other embodiments, Xaa$^6$ is N-methyl-Gly. In other embodiments, Xaa$^6$ is D-Ala. N-methyl-Gly and D-Ala at position Xaa$^6$ have been reported to retain strong binding affinity for GRPR (e.g. see: Table 4 in Horwell et al., 1996 *Int. J. Peptide Protein Res.* 48:522-531; Table 3 in Lin et al., 1995 *European Journal of Pharmacology* 284:55-69).

In some embodiments, Xaa$^7$ is His. In other embodiments, Xaa$^7$ is NMe-His. His at position Xaa$^7$ is found in wildtype BBN and GRP. NMe-His at position Xaa7 has been reported to retain binding affinity for GRPR (e.g. see: Table 4 in Horwell et al., 1996 *Int. J. Peptide Protein Res.* 48:522-531).

In some embodiments, Xaa$^8$ is Leu. In other embodiments, Xaa$^8$ is D-Pro. In other embodiments, Xaa$^8$ is Phe. Leu at position Xaa$^8$ is found in wildtype BBN and GRP. D-Pro at position Xaa$^8$ has been reported to retain binding affinity for GRPR (e.g. see: Leban, et al., 1994, J. Med. Chem. 37:439-445). Phe at position Xaa$^8$ is supported by Phe at this position in ranatensin and litorin, which have very strong binding affinity to the GRPR (Heimbrook et al., 1991 *J. Med. Chem.* 34:2102-2107; Lin et al., 1995 *European Journal of Phamacology* 294:55-69).

In some embodiments, Xaa$^9$ is Pro (i.e. Xaa$^9$-NH$_2$ is C-terminally amidated Pro). In other embodiments, Xaa$^9$ is Phe (i.e. Xaa$^9$-NH$_2$ is C-terminally amidated Phe). In other embodiments, Xaa$^9$ is 4-oxa-L-Pro (i.e. Xaa$^9$-NH$_2$ is C-terminally amidated 4-oxa-L-Pro). In other embodiments, Xaa$^9$ is Me$_2$Thz (i.e. Xaa$^9$-NH$_2$ is C-terminally amidated Me$_2$Thz). In other embodiments, Xaa$^9$ is Thz (i.e. Xaa$^9$-NH$_2$ is C-terminally amidated Thz). Pro at position Xaa$^9$ has been reported to retain binding affinity for GRPR (e.g. see: Lau, et al., 2019, ACS Omega 4:1470-1478; WO/2021/068051). Phe at position Xaa$^9$ has been reported to retain affinity for GRPR (e.g. see: Leban, et al., 1994, J. Med. Chem. 37:439-445). Thz at position Xaa$^9$ has been reported to retain binding affinity for GRPR (e.g. see: Cai, et al., 1994 Proc Natl Acad Sci USA 91:12664-12668).

In some embodiments, "ψ" represents a peptide bond joining Xaa$^8$ and Xaa$^9$. In other embodiments, "ψ" represents a reduced peptide bond joining Xaa$^8$ and Xaa$^9$, meaning that the main chain amide (e.g. —C(O)NH—) formed between Xaa$^8$ and Xaa$^9$ is replaced by —CH$_2$—N—.

In some embodiments, -Xaa$^1$-Xaa$^2$-Xaa$^3$-Xaa$^4$-Xaa$^5$-Xaa$^6$-Xaa$^7$-Xaa$^8$-ψ-Xaa$^9$-NH$_2$ is -D-Phe-Gln-Trp-Ala-Val-Gly-His-Leu-Thz-NH$_2$.

In some embodiments, -Xaa$^1$-Xaa$^2$-Xaa$^3$-Xaa$^4$-Xaa$^5$-Xaa$^6$-Xaa$^7$-Xaa$^8$-ψ-Xaa$^9$-NH$_2$ is -D-2-Nal-Gln-Trp-Ala-Val-Gly-His-Leu-Thz-NH$_2$.

In some embodiments, -Xaa$^1$-Xaa$^2$-Xaa$^3$-Xaa$^4$-Xaa$^5$-Xaa$^6$-Xaa$^7$-Xaa$^8$-ψ-Xaa$^9$-NH$_2$ is -D-Phe-Gln-Trp-Ala-Val-Gly-NMe-His-Leu-Thz-NH$_2$.

In some embodiments, -Xaa$^1$-Xaa$^2$-Xaa$^3$-Xaa$^4$-Xaa$^5$-Xaa$^6$-Xaa$^7$-Xaa$^8$-ψ-Xaa$^9$-NH$_2$ is -D-Phe-Gln-Trp-Ala-Tle-Gly-His-Leu-Thz-NH$_2$.

In some embodiments, -Xaa$^1$-Xaa$^2$-Xaa$^3$-Xaa$^4$-Xaa$^5$-Xaa$^6$-Xaa$^7$-Xaa$^8$-ψ-Xaa$^9$-NH$_2$ is -Phe-Gln-Trp-Ala-Tle-Gly-NMe-His-Leu-Thz-NH$_2$.

In some embodiments, -Xaa$^1$-Xaa$^2$-Xaa$^3$-Xaa$^4$-Xaa$^5$-Xaa$^6$-Xaa$^7$-Xaa$^8$-ψ-Xaa$^9$-NH$_2$ is -D-Phe-His-Trp-Ala-Val-Gly-His-LeuψThz-NH$_2$.

In some embodiments, -Xaa$^1$-Xaa$^2$-Xaa$^3$-Xaa$^4$-Xaa$^5$-Xaa$^6$-Xaa$^7$-Xaa$^8$-ψ-Xaa$^9$-NH$_2$ is -D-Phe-His-Trp-Ala-Tle-Gly-NMe-His-Leu-Thz-NH$_2$.

In some embodiments, -Xaa$^1$-Xaa$^2$-Xaa$^3$-Xaa$^4$-Xaa$^5$-Xaa$^6$-Xaa$^7$-Xaa$^8$-ψ-Xaa$^9$-NH$_2$ is -D-Phe-Gln-Trp-Ala-Tle-Gly-His-LeuψThz-NH$_2$.

R$^L$ is a linkage moiety joining the linker to the N-terminus of Xaa$^1$. In some embodiments, R$^L$ is —C(O)—. In other embodiments, R$^L$ is —NH—C(O)—. In yet other embodiments, R$^L$ is—NH—C(S)—;

The linker enables attachment of 1-5 radiolabelling groups, and optionally an albumin binder, to the compound.

A non-limiting example of a suitable linker is a peptide linker. More generally, the linker is a linear or branched chain of n1 units of -L$^1$R$^1$- and/or -(L$^1$)$_2$R$^1$-(i.e. each unit is independently -L$^1$R$^1$- or -(L$^1$)$_2$R$^1$-), wherein n1 is 1-20. In alternative embodiments, n1 is 1, 2, 3, 4, 5, 6, 7, 8, 9, 10, 11, 12, 13, 14, 15, 16, 17, 18, 19, or 20. In some embodiments, n1 is 1-7. In some embodiments, n1 is 1. In other embodiments, n1 is 2. In other embodiments, n1 is 3. In other embodiments, n1 is 4. In other embodiments, n1 is 5. In other embodiments, n1 is 6. In other embodiments, n1 is 7.

In some embodiments, n6 is 1 and n1 is 1.

In some embodiments, n6 is 1, n1 is 1, and L$^1$ is —C(O)NH—.

In some embodiments, n6 is 1, n1 is 1, L$^1$ is —C(O)NH—, and R$^L$ is —C(O)—.

In some embodiments, n6 is 1, n1 is 1, L$^1$ is —C(O)NH—, R$^L$ is —C(O)—, and R$^1$ is a linear C$_{1-5}$ alkylenyl or —(CH$_2$)$_2$—[(CH$_2$)$_2$]$_{1-6}$—(CH$_2$)$_{0-2}$.

In some embodiments, R$^{rad}_{n6}$-[linker]- is configured as shown in Formula II:

(II)

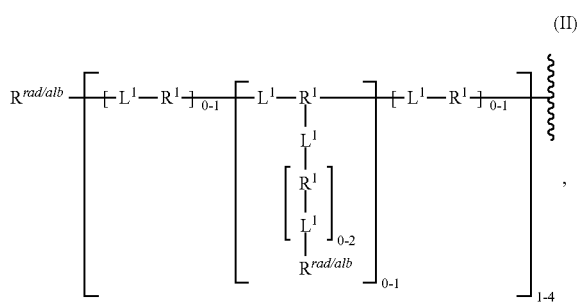

wherein L¹ and R¹ are as defined in the definition of the linker in Formula I, and $R^{rad/alb}$ is either $R^{rad}$ or $R^{alb}$, and wherein 0-1 $R^{rad/alb}$ is $R^{alb}$.

Each R¹ (Formula I or II) is, independently, a linear, branched, and/or cyclic $C_{n2}$ alkylenyl, alkenylenyl and/or alkynylenyl, wherein each n2 is independently 1-20, wherein any carbon bonded to two other carbons is optionally independently replaced by N, S, or O, and carbons are optionally independently substituted. In some embodiments, each n2 is independently 1-15 or 1-10. In alternative embodiments, each n2 is independently 1, 2, 3, 4, 5, 6, 7, 8, 9, 10, 11, 12, 13, 14, 15, 16, 17, 18, 19, or 20. In some embodiments, each R¹ is independently a $C_{n2}$ alkylenyl wherein any carbon bonded to two other carbons is optionally independently replaced by N, S, or O, and carbons are optionally independently substituted. In some embodiments, each R¹ is independently a linear $C_{1-5}$ alkylenyl or $—(CH_2)_2—[(CH_2)_2]_{1-6}—(CH_2)_{0-2}—$; in some of these embodiments, n1 is 1-7. In some embodiments, each R¹ is independently $—C(R^{aa})H—$, wherein each $R^{aa}$ is independently the sidechain of a proteinogenic amino acid or the sidechain of an alpha amino acid from Table 1. In some embodiments, each R¹ is independently a proteinogenic amino acid or an amino acid from Table 1 omitting the backbone amino and carboxylic acid groups of the amino acid.

Each L¹ (Formula I or II) is a linkage group. In some embodiments, at least one L¹ is —S—. In some embodiments, at least one L¹ is —N(R²)C(O)—; in some of these embodiments, at least one R² is hydrogen. In some embodiments, at least one L¹ is —C(O)N(R²)—; in some of these embodiments, at least one R² is hydrogen. In some embodiments, at least one L¹ is —NH—C(O)—NH—. In some embodiments, at least one L¹ is —NH—C(S)—NH—. In some embodiments, at least one L¹ is

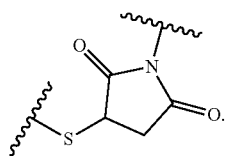 [SMILES: *SC1CC(=O)N(*)C1=O]

In some embodiments, at least one L¹ is

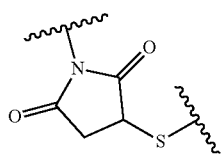

In some embodiments, at least one L¹ is

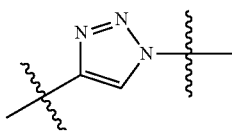

In some embodiments, at least one L¹ is

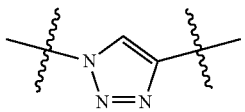

In some embodiments, the linker has the configuration shown in Formula II, and each R¹ is independently a linear $C_{1-5}$ alkylenyl or $—(CH_2)_2—[O(CH_2)_2]_{1-6}—(CH_2)_{0-2}—$.

In some embodiments, n6 is 1, the linker is L¹ R¹ and together with $R^L$ forms —C(O)-Xaa¹¹- wherein Xaa¹¹ is a proteinogenic amino acid residue or an amino acid residue selected from Table 1. In some embodiments, Xaa¹¹ is pABzA-DIG. In other embodiments, Xaa¹¹ is Pip. In other embodiments, Xaa¹¹ is dPEG2. In other embodiments, Xaa¹¹ is Acp.

In some embodiments, the linker together with $R^L$ forms a peptide linker, wherein peptide (amide) bonds are independently optionally methylated, optionally replacing one or more amide bonds with 1,2,3-triazole linkages (product of a reaction between an azide and an alkyne). In some embodiments, the peptide linker is a linear peptide linker, optionally replacing one or more amide bonds with 1,2,3-triazole linkages. In some embodiments, the peptide linker is a branched peptide linker, where the amino acid residues may be connected through a combination of main chain amide (peptide) bonds and 'side chain'-to-'main chain' or 'side chain'-to-'side chain' bonds. For example, a branched peptide may be connected by one or more of: backbone (main chain) peptide (amide) bonds, 'main chain'-to-side chain amide bonds (between an amino group and a carboxylic acid group), optionally replacing one or more amide bonds with 1,2,3-triazole linkages. In some such embodiments, the peptide linker is $(Xaa^{10})_{1-20}$, wherein each $Xaa^{10}$ is independently a proteinogenic amino acid residue or a non-proteinogenic amino acid residue (e.g. selected from Table 1) linked together as a linear or branched peptide linker. In some embodiments, $(Xaa^{10})_{1-20}$ is a linear peptide linker. In some embodiments, $(Xaa^{10})_{1-20}$ is a branched peptide linker. $R^{rad}$ is bonded to the peptide linker through an amide bond or another L¹ linkage group; in some embodiments, Rrad is bonded to the peptide linker through an amide bond.

In some embodiments, each $Xaa^{10}$ is independently $—N(R^a)R^bC(O)—$ wherein: $R^a$ may be H or methyl; $R^b$ may be a 1- to 30-atom alkylenyl, heteroalkylenyl, alkenylenyl, heteroalkenylenyl, alkynylenyl, or heteroalkynylenyl, including linear, branched, and/or cyclic (whether aromatic or nonaromatic as well as mono-cyclic, multicyclic or fused cyclic) structures; or N, $R^a$ and $R^b$ together may form a 5- to 7-atom heteroalkylenyl or heteroalkenylenyl.

In some embodiments, $(Xaa^{10})_{1-20}$ consists of a single amino acid or residue. In some embodiments, $(Xaa^{10})_{1-20}$ is a dipeptide, wherein each $Xaa^{10}$ may be the same or different. In some embodiments, $(Xaa^{10})_{1-20}$ is a tripeptide, wherein each $Xaa^{10}$ may be the same, different or a combination thereof. In some embodiments, $(Xaa^{10})_{1-20}$ consists of 4 amino acid residues connected by peptide bonds, wherein each $Xaa^{10}$ may be the same, different or a combination thereof. In some embodiments, each $Xaa^{10}$ is independently selected from proteinogenic amino acids and the non-proteinogenic amino acids listed in Table 1, wherein each peptide backbone amino group of the peptide linker is independently optionally methylated. In some embodiments, all peptide backbone amino groups of the peptide linker are methylated. In other embodiments, only one peptide backbone amino group of the peptide linker is methylated. In other embodiments, only two peptide backbone amino groups of the peptide linker are methylated. In other embodiments, no peptide backbone amino groups of the peptide linker are methylated.

In some embodiments, n6 is 1. In other embodiments, n6 is 2. In other embodiments, n6 is 3. In other embodiments, n6 is 4. In other embodiments, n6 is 5.

In some embodiments, the linker does not comprise $R^{alb}$.

In some embodiments, the linker comprises $R^{alb}$ bonded to an $L^1$ of the linker.

In some embodiments, $R^{alb}$ is $-(CH_2)_{n3}-CH_3$ wherein n3 is 8-20. In alternative embodiments, n3 is 8, 9, 10, 11, 12, 13, 14, 15, 16, 17, 18, 19, or 20.

In some embodiments, $R^{alb}$ is $-(CH_2)_{n4}-C(O)OH$ wherein n4 is 8-20. In alternative embodiments, n4 is 8, 9, 10, 11, 12, 13, 14, 15, 16, 17, 18, 19, or 20.

In some embodiments, $R^{alb}$ is

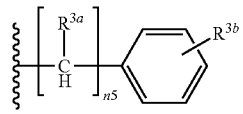

wherein n5 is 1-4 and $R^{3a}$ is H or methyl, and $R^{3b}$ is I, Br, F, Cl, H, OH, $OCH_3$, $NH_2$, $NO_2$ or $C_1$-$C_6$ alkyl. In alternative embodiments, n5 is 1, 2, 3, or 4. In certain embodiments, $R^{3a}$ is H. In certain embodiments, $R^{3a}$ is methyl. In certain embodiments, $R^{3b}$ is I, Br, F, or Cl, optionally in para position. In certain embodiments, $R^{3b}$ is H. In certain embodiments, $R^{3b}$ is OH, optionally in para position. In certain embodiments, $R^{3b}$ is $OCH_3$, optionally in para position. In certain embodiments, $R^{3b}$ is $NH_2$, optionally in para position. In certain embodiments, $R^{3b}$ is $NO_2$, optionally in para position. In certain embodiments, $R^{3b}$ is $C_1$-$C_6$ alkyl, optionally in para position. In certain embodiments, $R^{3a}$ is H and $R^{3b}$ is $OCH_3$ or $NO_2$. In some embodiments, $R^{3a}$ is methyl and $R^{3b}$ is isobutyl, optionally para-isobutyl.

In some embodiments, $R^{alb}$ is

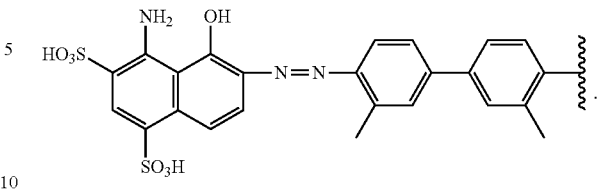

In some embodiments, at least one $R^{rad}$ is or comprises a radiometal chelator. The radiometal chelator may be any chelator suitable for binding a radiometal, a radionuclide-bound metal, or a radionuclide-bound metal-containing prosthetic group, and which is attached to the linker by forming an amide bond (between an amino group and a carboxylic acid group) or a 1,2,3-triazole (reaction between an azide and an alkyne), or by reaction between a maleimide and a thiol group. Many suitable radiometal chelators are known, e.g. as summarized in Price and Orvig, *Chem. Soc. Rev.*, 2014, 43, 260-290. In some embodiments, but without limitation, each radiometal chelator is independently selected from the group consisting of: DOTA and DOTA derivatives; DOTAGA; NOTA; NODAGA; NODASA; CB-DO2A; 3p-C-DEPA; TCMC; DO3A; DTPA and DTPA analogues optionally selected from CHX-A"-DTPA and 1B4M-DTPA; TETA; NOPO; Me-3,2-HOPO; CB-TE1A1P; CB-TE2P; MM-TE2A; DM-TE2A; sarcophagine and sarcophagine derivatives optionally selected from SarAr, SarAr-NCS, diamSar, AmBaSar, and BaBaSar; TRAP; AAZTA; DATA and DATA derivatives; H2-macropa or a derivative thereof; $H_2$dedpa, $H_2$octapa, $H_4$py4pa, $H_4$Pypa, $H_2$azapa, $H_5$decapa, and other picolinic acid derivatives; CP256; PCTA; C-NETA; C-NE3TA; HBED; SHBED; BCPA; CP256; YM103; desferrioxamine (DFO) and DFO derivatives; $H_6$phospa; a trithiol chelate; mercaptoacetyl; hydrazinonicotinamide; dimercaptosuccinic acid; 1,2-ethylenediylbis-L-cysteine diethyl ester; methylenediphosphonate; hexamethylpropyleneamineoxime; and hexakis (methoxy isobutyl isonitrile). In some embodiments, at least one radiometal chelator is DOTA or a DOTA derivative.

Exemplary non-limiting examples of radiometal chelators and example radionuclides that may be chelated by these chelators are shown in Table 2. In alternative embodiments, at least one $R^{rad}$ is a radiometal chelator selected from those listed above or in Table 2. It is noted, however, that one skilled in the art could replace any of the chelators listed herein with another chelator.

TABLE 2

Exemplary chelators and exemplary radionuclide which bind said chelators

| Chelator | Radionuclide |
|---|---|
| ![DOTA structure]<br>DOTA, 1,4,7,10-tetraazacyclododecane-<br>1,4,7,10-tetraacetic acid | Cu-64/67<br>Ga-67/68<br>In-111<br>Lu-177<br>Y-86/90<br>Bi-203/212/213<br>Pb-212<br>Ac-225<br>Gd-159<br>Yb-175<br>Ho-166<br>As-211<br>Sc-44/47 |

TABLE 2-continued

Exemplary chelators and exemplary radionuclide which bind said chelators

| Chelator | Radionuclide |
| --- | --- |
| | Pm-149 |
| | Pr-142 |
| | Sn-117m |
| | Sm-153 |
| | Tb-149/152/155/161 |
| | Er-165 |
| | Ra-223/224 |
| | Th-227 |
| CB-DO2A, 4,10-bis(carboxymethyl)-1,4,7,10-tetraazabicyclo[5.5.2]tetradecane | Cu-64/67 |
| TCMC, 1,4,7,10-tetrakis(carbamoylmethyl)-1,4,7,10-tetraazacyclododecane | Pb-212 |
| 3p-C-DEPA | Bi-212/213 |
| p-NH$_2$-Bn-Oxo-DO3A | Cu-64/67 |
| TETA, 1,4,8,11-tetraazacyclotetradecane-1,4,8,11-tetraacetic acid | Cu-64/67 |

TABLE 2-continued

Exemplary chelators and exemplary radionuclide which bind said chelators

| Chelator | Radionuclide |
|---|---|
| 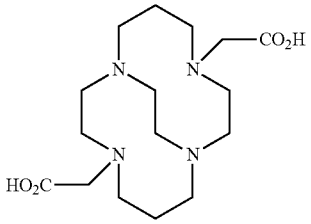 [SMILES: O=C(O)CN1CCCN2CCN(CCCN(CC(=O)O)CC2)CC1]<br>CB-TE2A, 4,11-bis-(carboxymethyl)-1,4,8,11-tetraazabicyclo[6.6.2]-hexadecane | Cu-64/67 |
| 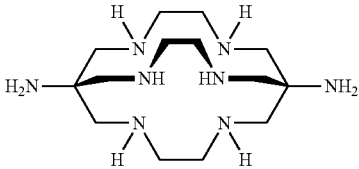<br>Diamsar | Cu-64/67 |
| 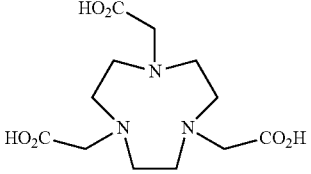 [SMILES: O=C(O)CN1CCN(CC(=O)O)CCN(CC(=O)O)CC1]<br>NOTA, 1,4,7-triazacyclononane-1,4,7-triacetic acid | Cu-64/67<br>Ga-68<br>In-111<br>Sc-44/47 |
| 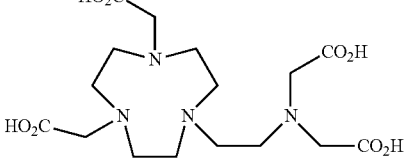<br>NETA, {4-[2-(bis-carboxymethylamino)-ethyl]-7-carboxymethyl-[1,4,7]triazonan-1-yl}-acetic acid | Cu-64/67<br>Ga-68<br>Lu-177<br>Y-86/90<br>Bi-213<br>Pb-212 |
| 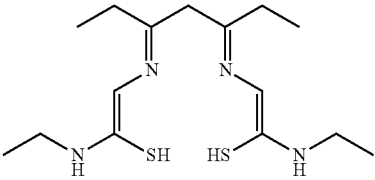 [SMILES: CCN/C(S)=C/N=C(\CC)C/C(CC)=N/C=C(\S)NCC]<br>HxTSE | Au-198/199 |
| 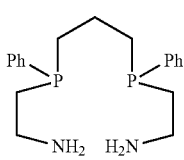<br>P₂N₂Ph₂ | Rh-105 |

TABLE 2-continued

Exemplary chelators and exemplary radionuclide which bind said chelators

| Chelator | Radionuclide |
|---|---|
| 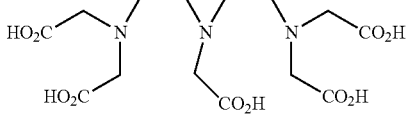<br>DTPA, diethylenetriaminepentaacetic acid | In-111<br>Sc-44/47<br>Lu-177<br>Y-86/90<br>Sn-117m<br>Pd-109 |
| 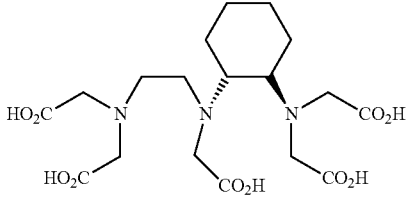<br>CHX-A00-DTPA, 2-(p-isothiocyanatobenzyl)-cyclohexyldiethylenetriaminepentaacetic acid | In-111<br>Lu-177<br>Y-86/90<br>Bi-212/213 |
| 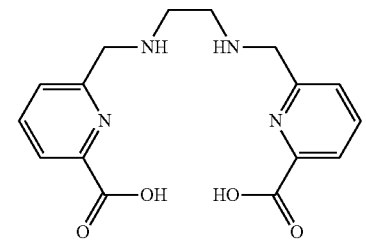 [SMILES: O=C(O)c1cccc(CNCCNCc2cccc(C(=O)O)n2)n1]<br>H$_2$dedpa, 1,2-[[6-(carboxy)-pyridin-2-yl]-methylamino]ethane | Cu-64/67 |
| 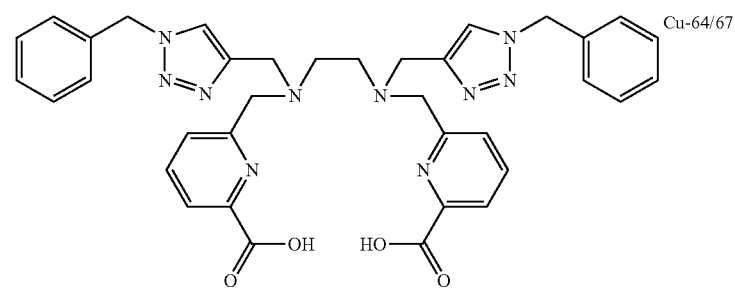<br>H$_2$azapa, N,N0-[1-benzyl-1,2,3-triazole-4-yl]methyl-N,N0-[6-(carboxy)pyridin-2-yl]-1,2-diaminoethane | Cu-64/67 |
| 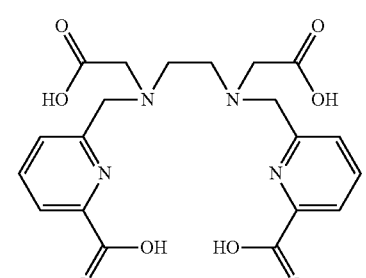<br>H$_4$octapa | In-111<br>Lu-177<br>Y-86/90<br>Ac-225 |

TABLE 2-continued

Exemplary chelators and exemplary radionuclide which bind said chelators

| Chelator | Radionuclide |
| --- | --- |
| H₆phospa | Ac-225 |
| H₄CHXoctapa | In-111<br>Ac-225 |
| H₅decapa | In-111<br>Lu-177<br>Ac-225 |
| H₄neunpa-p-Bn-NO₂ | In-111<br>Lu-177<br>Ac-225 |

TABLE 2-continued
Exemplary chelators and exemplary radionuclide which bind said chelators
| Chelator | Radionuclide |
|---|---|
| 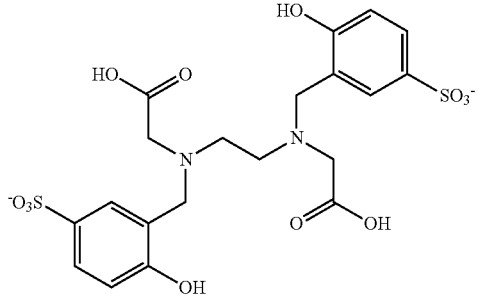<br>SHBED, N,N0-bis(2-hydroxy-5-sulfobenzyl)-ethylenediamine-N,N0-diacetic acid | In-111<br>Ga-68 |
| 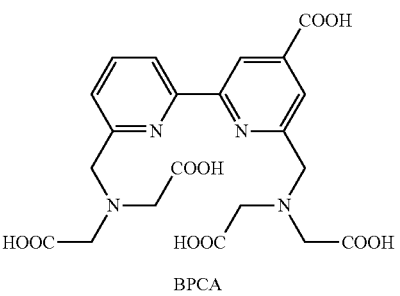<br>BPCA | In-111 |
| 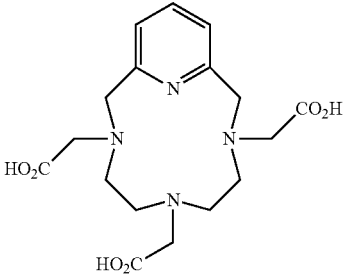<br>PCTA, 3,6,9,15-tetraazabicyclo[9.3.1]-pentadeca-1(15),11,13-triene-3,6,9,-triacetic acid | Cu-64/67 |
| 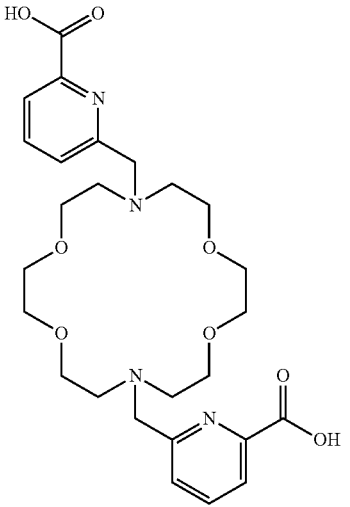 [SMILES: O=C(O)c1cccc(CN2CCOCCOCCN(Cc3cccc(C(=O)O)n3)CCOCCOCC2)n1]<br>H2-MACROPA | Ac-225 |

TABLE 2-continued
Exemplary chelators and exemplary radionuclide which bind said chelators
| Chelator | Radionuclide |
|---|---|
(N,N'-bis[(6-carboxy-2-pyridil)methyl]-4,13-diaza-18-crown-6)
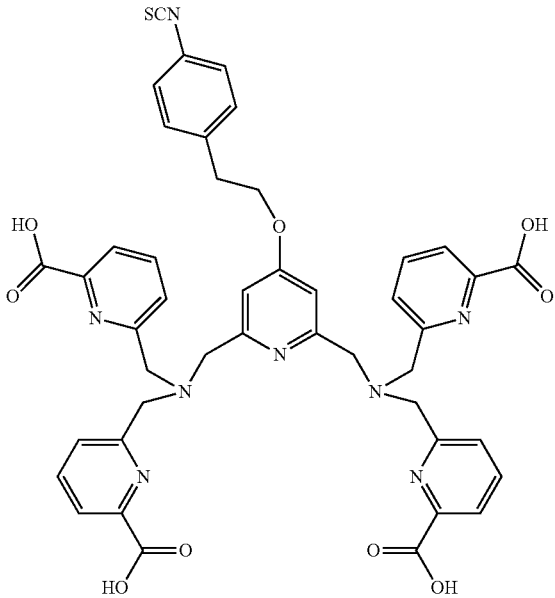
H4py4pa-phenyl-NCS
Ac-225
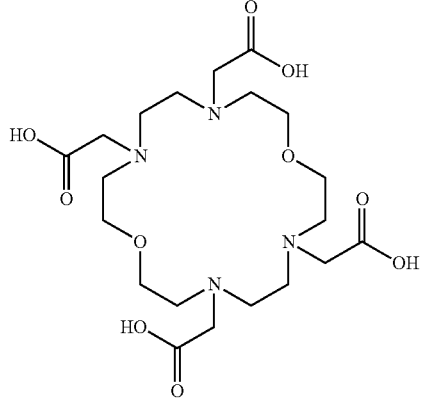 [SMILES: O=C(O)CN1CCOCCN(CC(=O)O)CCN(CC(=O)O)CCOCCN(CC(=O)O)CC1]
Crown
Ac-225
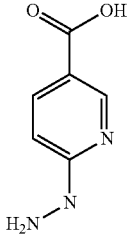
HYNIC
Tc-99m
Tc-94m TABLE 2-continued Exemplary chelators and exemplary radionuclide which bind said chelators

| Chelator | Radionuclide |
|---|---|
| 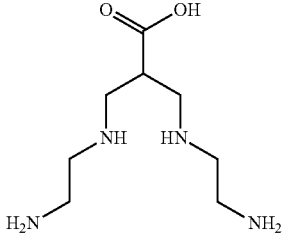 [SMILES: NCCNCC(CNCCN)C(=O)O]<br>N4 (6-carboxy-1,4,7,11-tetraazaundecane) | Tc-99m<br>Tc-94m |
| 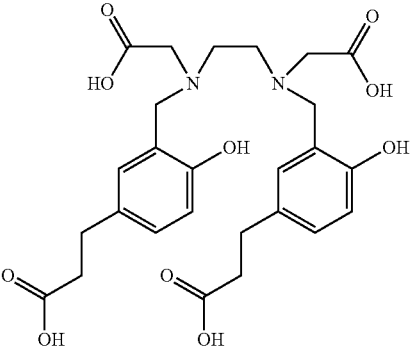 [SMILES: O=C(O)CCc1ccc(O)c(CN(CCN(CC(=O)O)Cc2cc(CCC(=O)O)ccc2O)CC(=O)O)c1]<br>HBED-CC | Ga-68 |

In some embodiments, each radiometal chelator is independently selected from Table 2, wherein each chelator is optionally bound by a radiometal. In some embodiments, each radiometal chelator is bound by one of the corresponding radionuclides shown in Table 2.

In some embodiments, at least one $R^{rad}$ is DOTA, or a derivative thereof, linked via an amide (e.g. formed from one of the carboxyl groups shown in Table 2. In some embodiments, at least one $R^{rad}$ is CB-DO2A, or a derivative thereof, linked via an amide (e.g. formed from one of the carboxyl groups shown in Table 2). In some embodiments, at least one $R^{rad}$ is TCMC, or a derivative thereof, linked via an amide (e.g. formed from one of the —$CONH_2$ groups shown in Table 2). In some embodiments, the chelator at least one $R^{rad}$ is 3p-C-DEPA, or a derivative thereof, linked via an amide (e.g. formed from one of the carboxyl groups shown in Table 2). In some embodiments, at least one $R^{rad}$ is p-NH 2-Bn-Oxo-DO3A or a derivative thereof, linked via an amide (e.g. formed from one of the carboxyl groups shown in Table 2). In some embodiments, at least one $R^{rad}$ is TETA, or a derivative thereof, linked via an amide (e.g. formed from one of the carboxyl groups shown in Table 2). In some embodiments, at least one $R^{rad}$ is CB-TE2A, or a derivative thereof, linked via an amide (e.g. formed from one of the carboxyl groups shown in Table 2). In some embodiments, at least one $R^{rad}$ is Diamsar, or a derivative thereof, linked via an amide (e.g. formed from one of the amino groups shown in Table 2). In some embodiments, at least one $R^{rad}$ is NOTA, or a derivative thereof, linked via an amide (e.g. formed from one of the carboxyl groups shown in Table 2). In some embodiments, at least one $R^{rad}$ is NETA, or a derivative thereof, linked via an amide (e.g. formed from one of the carboxyl groups shown in Table 2).

In some embodiments, at least one $R^{rad}$ is HxTSE, or a derivative thereof, linked via an amide (e.g. formed from one of the amino groups shown in Table 2). In some embodiments, at least one $R^{rad}$ is $P_2N_2Ph_2$, or a derivative thereof, linked via an amide (e.g. formed from one of the amino groups shown in Table 2). In some embodiments, at least one $R^{rad}$ is DTPA, or a derivative thereof, linked via an amide (e.g. formed from one of the carboxyl groups shown in Table 2). In some embodiments, at least one $R^{rad}$ is CHX-A00-DTPA, or a derivative thereof, linked via an amide (e.g. formed from one of the carboxyl groups shown in Table 2). In some embodiments, at least one $R^{rad}$ is H 2 dedpa, or a derivative thereof, linked via an amide (e.g. formed from one of the carboxyl groups shown in Table 2). In some embodiments, at least one $R^{rad}$ is $H_2$azapa, or a derivative thereof, linked via an amide (e.g. formed from one of the carboxyl groups shown in Table 2). In some embodiments, at least one $R^{rad}$ is $H_4$octapa, or a derivative thereof, linked via an amide (e.g. formed from one of the carboxyl groups shown in Table 2). In some embodiments, at least one $R^{rad}$ is $H_6$phospa, or a derivative thereof, linked via an amide (e.g. formed from one of the carboxyl groups shown in Table 2). In some embodiments, at least one $R^{rad}$ is $H_4$CHXoctapa, or a derivative thereof, linked via an amide (e.g. formed from one of the carboxyl groups shown in Table 2). In some embodiments, at least one $R^{rad}$ is $H_6$decapa, or a derivative thereof, linked via an amide (e.g. formed from one of the carboxyl groups shown in Table 2). In some embodiments, at least one $R^{rad}$ is $H_4$neunpa-p-Bn-NO2, or a derivative thereof, linked via an amide (e.g. formed from one of the carboxyl groups shown in Table 2). In some embodiments, at least one $R^{rad}$ is SHBED, or a derivative thereof, linked via an amide (e.g. formed from one of the carboxyl groups shown in Table 2). In some embodiments, at least one $R^{rad}$ is BPCA, or a derivative thereof, linked via an amide (e.g. formed from one of the carboxyl groups shown in Table 2). In some embodiments, at least one $R^{rad}$ is PCTA, or a derivative thereof, linked via an amide (e.g. formed from one of the carboxyl groups shown in Table 2). In some embodiments, at least one $R^{rad}$ is H2-MACROPA, or a derivative thereof, linked via an amide (e.g. formed from one of the carboxyl groups shown in Table 2). In some embodiments, at least one $R^{rad}$ is Crown, or a derivative thereof, linked via an amide (e.g. formed from one of the carboxyl groups shown in Table 2). In some embodiments, at least one $R^{rad}$ is HYNIC, or a derivative thereof, linked via an amide (e.g. formed from the carboxyl group shown in Table 2). In some embodiments, at least one $R^{rad}$ is N4, or a derivative thereof, linked via an amide (e.g. formed from the carboxyl group shown in Table 2). In some embodiments, at least one $R^{rad}$ is HBED-CC, or a derivative thereof, linked via an amide (e.g. formed from one of the carboxyl groups shown in Table 2).

In some embodiments, the radiometal chelator (or one of the radiometal chelators) is a derivative of a radiometal chelator shown in Table 2. A derivative may include, e.g. (1) modification of a functional group of the chelator (e.g. a carboxyl group, an amino group, etc.) or (2) attachment of a new functional group (e.g. attachment of an R-group to an ethylene carbon located between two nitrogen atoms, wherein the R-group is a functional group fused to a spacer). In some embodiments, a carboxyl functional group shown in Table 2 is replaced with azidopropyl ethylacetamide (e.g. azido-mono-amide-DOTA), butynylacetamide (e.g. butyne-DOTA), thioethylacetamide (e.g. DO3A-thiol), maleimido-ethylacetamide (e.g. maleimido-mono-amide-DOTA), or N-hydroxysuccinimide ester (e.g. DOTA-NHS-ester). When linked, these derivative chelators can be linked either via an amide (formed from a remaining carboxyl group) or via —C(O)—NH—$(CH_2)_{2-3}$-(triazole) or —C(O)—NH—$(CH_2)_{2-3}$-(thiomaleimide). In other embodiments, a backbone carbon (e.g. in an ethylene positioned between two backbone nitrogen atoms) in the chelator ring is fused to an R-group containing a functional group, optionally wherein the R-group is —$(CH_2)_{1-3}$-(phenyl)-N=C=S or —$(CH_2)_{1-3}$-(phenyl)-N=C=O, optionally 1,4-isothiocyanatobenzyl; e.g. p-SCN-Bn-DOTA (S-2-(4-isothiocyanatobenzyl)-1,4,7,10-tetraazacyclododecane tetraacetic acid), p-SCN-Bn-NOTA (2-S-(4-isothiocyanatobenzyl)-1,4,7-triazacyclononane-1,4,7-triacetic acid), and the like. When linked, these derivatives can form a urea linkage (formed from isocyanate) or a thiourea linkage (formed from isothiocyanate).

In some embodiments, a radiometal chelator is conjugated with a radiometal, a radionuclide-bound metal, or a radionuclide-bound metal-containing prosthetic group, and the radiometal, the radionuclide-bound metal, or the radionuclide-bound metal-containing prosthetic group is chelated to the radionuclide-chelator complex. In some embodiments, the radiometal, the radionuclide-bound metal, or the radionuclide-bound metal-containing prosthetic group is: $^{68}$Ga, $^{61}$Cu, $^{64}$Cu, $^{67}$Cu, $^{67}$Ga, $^{111}$In, $^{44}$Sc, $^{86}$Y, $^{89}$Zr, $^{90}$Nb, $^{177}$Lu, $^{117m}$Sn, $^{165}$Er, $^{90}$Y, $^{227}$Th, $^{225}$Ac, $^{213}$Bi, $^{212}$Bi, $^{72}$As, $^{77}$As, $^{211}$At, $^{203}$Pb, $^{212}$Pb, $^{47}$Sc, $^{166}$Ho, $^{188}$Re, $^{186}$Re, $^{149}$Pm, $^{159}$Gd, $^{105}$Rh, $^{109}$Pd, $^{198}$Au, $^{199}$Au, $^{175}$Yb, $^{142}$Pr, $^{114m}$In, $^{94m}$Tc, $^{99m}$Tc, $^{149}$Tb, $^{152}$Tb, $^{155}$Tb, $^{161}$Tb, or [$^{18}$F]AlF. In other embodiments, the radiometal, the radionuclide-bound metal, or the radionuclide-bound metal-containing prosthetic group is: $^{68}$Ga, $^{61}$Cu, $^{64}$Cu, $^{67}$Cu, $^{67}$Ga, $^{111}$In, $^{44}$Sc, $^{86}$Y, $^{177}$Lu, $^{90}$Y, $^{225}$Ac, $^{213}$Bi, or $^{212}$Bi. In some embodiments, the chelator is a chelator from Table 2 and the chelated radionuclide is a radionuclide indicated in Table 2 as a binder of the chelator.

In some embodiments, the chelator is: DOTA or a derivative thereof, conjugated with $^{177}$Lu, $^{111}$In, $^{213}$Bi, $^{68}$Ga, $^{87}$Ga, $^{203}$Pb, $^{212}$Pb, $^{44}$Sc, $^{47}$Sc, $^{90}$Y, $^{86}$Y, $^{225}$Ac, $^{117m}$Sn, $^{153}$Sm, $^{149}$Tb, $^{152}$Tb, $^{155}$Tb, $^{161}$Tb, $^{165}$Er, $^{213}$Bi, $^{224}$Ra, $^{212}$Bi, $^{212}$Pb, $^{225}$Ac, $^{227}$Th, $^{223}$Ra, $^{47}$Sc, $^{64}$Cu or $^{67}$Cu; H2-MACROPA conjugated with $^{225}$Ac; Me-3,2-HOPO conjugated with $^{227}$Th; H$_4$py4pa conjugated with $^{225}$Ac, $^{227}$Th or $^{177}$Lu; H$_4$pypa conjugated with $^{177}$Lu; NODAGA conjugated with $^{68}$Ga; DTPA conjugated with $^{111}$In; or DFO conjugated with $^{89}$Zr.

In some embodiments, the chelator is TETA (1,4,8,11-tetraazacyclotetradecane-1,4,8,11-tetraacetic acid), SarAr (1-N-(4-Aminobenzyl)-3,6,10,13,16,19-hexaazabicyclo[6.6.6]-eicosane-1,8-diamine), NOTA (1,4,7-triazacyclononane-1,4,7-triacetic acid), TRAP (1,4,7-triazacyclononane-1,4,7-tris[methyl(2-carboxyethyl)phosphinic acid), HBED (N,N0-bis(2-hydroxybenzyl)-ethylenediamine-N,N0-diacetic acid), 2,3-HOPO (3-hydroxypyridin-2-one), PCTA (3,6,9,15-tetraazabicyclo[9.3.1]-pentadeca-1(15),11,13-triene-3,6,9,-triacetic acid), DFO (desferrioxamine), DTPA (diethylenetriaminepentaacetic acid), OCTA PA (N,N0-bis(6-carboxy-2-pyridylmethyl)-ethylenediamine-N,N0-diacetic acid) or another picolinic acid derivative.

In some embodiments, an $R^{rad}$ is a chelator for radiolabelling with $^{99m}$Tc, $^{94m}$Tc, $^{186}$Re, or $^{188}$Re, such as mercaptoacetyl, hydrazinonicotinamide, dimercaptosuccinic acid, 1,2-ethylenediylbis-L-cysteine diethyl ester, methylenediphosphonate, hexamethylpropyleneamineoxime and hexakis(methoxy isobutyl isonitrile), and the like. In some embodiments, an $R^{rad}$ is a chelator, wherein the chelator is mercaptoacetyl, hydrazinonicotinamide, dimercaptosuccinic acid, 1,2-ethylenediylbis-L-cysteine diethyl ester, methylenediphosphonate, hexamethylpropyleneamineoxime or hexakis(methoxy isobutyl isonitrile). In some of these embodiments, the chelator is bound by a radionuclide. In some such embodiments, the radionuclide is $^{99m}$Tc, $^{94m}$Tc, $^{186}$Re, or $^{188}$Re.

In some embodiments, an $R^{rad}$ is a chelator that can bind $^{18}$F-aluminum fluoride ([$^{18}$F]AlF), such as 1,4,7-triazacyclononane-1,4-diacetate (NODA) and the like. In some embodiments, the chelator is NODA. In some embodiments, the chelator is bound by [$^{18}$F]AlF.

In some embodiments, an $R^{rad}$ is a chelator that can bind $^{72}$As or $^{77}$As, such as a trithiol chelate and the like. In some embodiments, the chelator is a trithiol chelate. In some embodiments, the chelator is conjugated to $^{72}$As. In some embodiments, the chelator is conjugated to $^{77}$As.

In certain embodiments, at least one $R^{rad}$ is a prosthetic group containing a trifluoroborate (BF$_3$), capable of $^{18}$F/$^{19}$F exchange radiolabeling. In some of these embodiments, the $R^{rad}$ is BF$_3$—$R^5$—$R^4$—, wherein $R^4$ is —$(CH_2)_{1-5}$, optionally methylene, and wherein BF$_3$—$R^5$— forms:

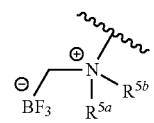

wherein $R^{5a}$ and $R^{5b}$ are each independently a $C_1$-$C_5$ linear or branched alkyl group, or a structure listed in Table 3 (below) or Table 4 (below). For Tables 3 and 4, each R group in each pyridine substituted with —OR, —SR, —NR—, —NHR or —NR$_2$ is independently a $C_1$-$C_5$ linear or branched alkyl. In some embodiments, at least one BF$_3$—R$^5$— forms

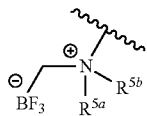

wherein R$^{5a}$ and R$^{5b}$ are each independently a $C_1$-$C_5$ linear or branched alkyl group. In some embodiments, at least one of the BF$_3$—R$^5$— group(s) is/are selected from those listed in Table 3. In some embodiments, at least one of the BF$_3$—R$^5$— group(s) is/are selected from those listed in Table 4. The trifluoroborate-containing prosthetic group(s) may comprise $^{18}$F. In some embodiments, one fluorine in BF$_3$ forms is $^{18}$F. In some embodiments, all three fluorines in BF$_3$ are $^{18}$F. In some embodiments, all three fluorines in BF$_3$ are $^{19}$F.

TABLE 3-continued
Exemplary BF$_3$—R$^5$— groups.
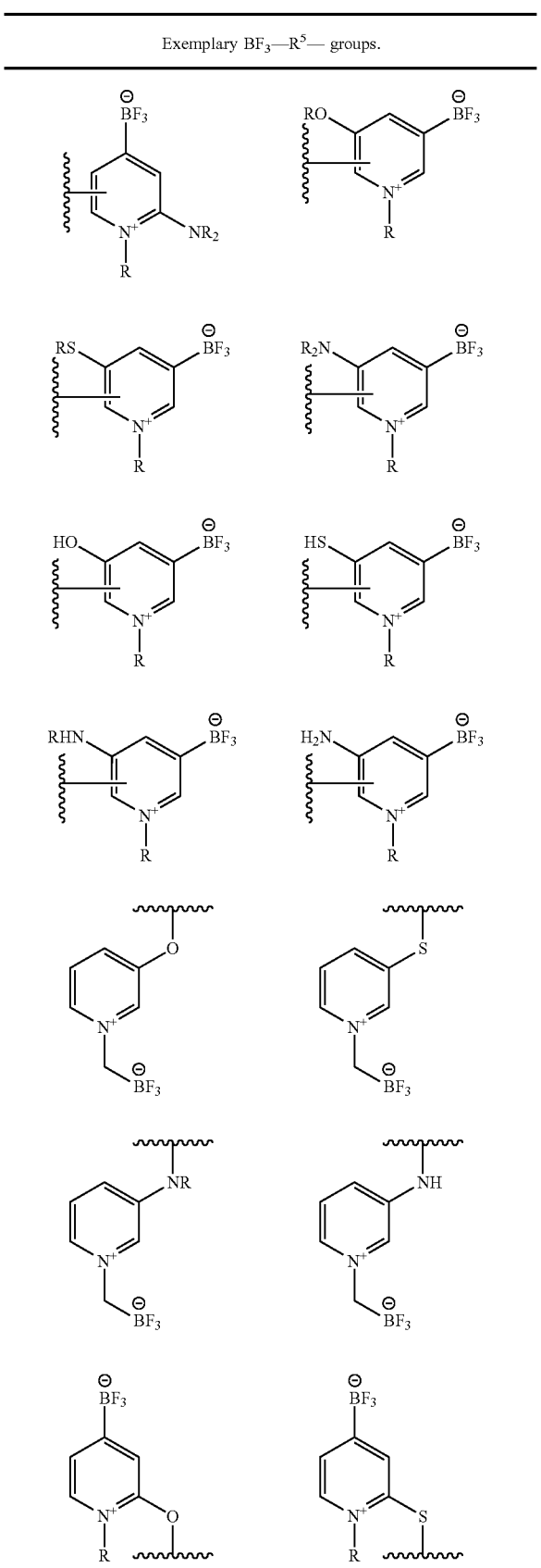
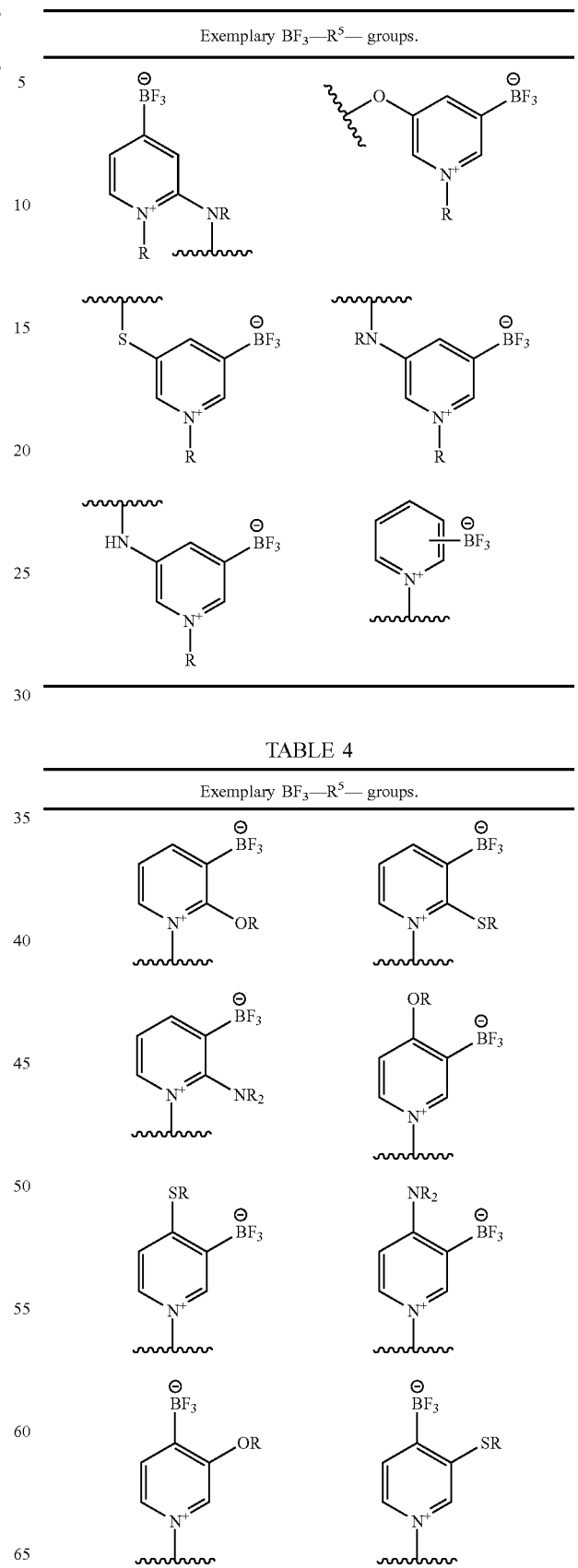
TABLE 4
Exemplary BF$_3$—R$^5$— groups.

TABLE 4-continued
Exemplary BF$_3$—R$^5$— groups.
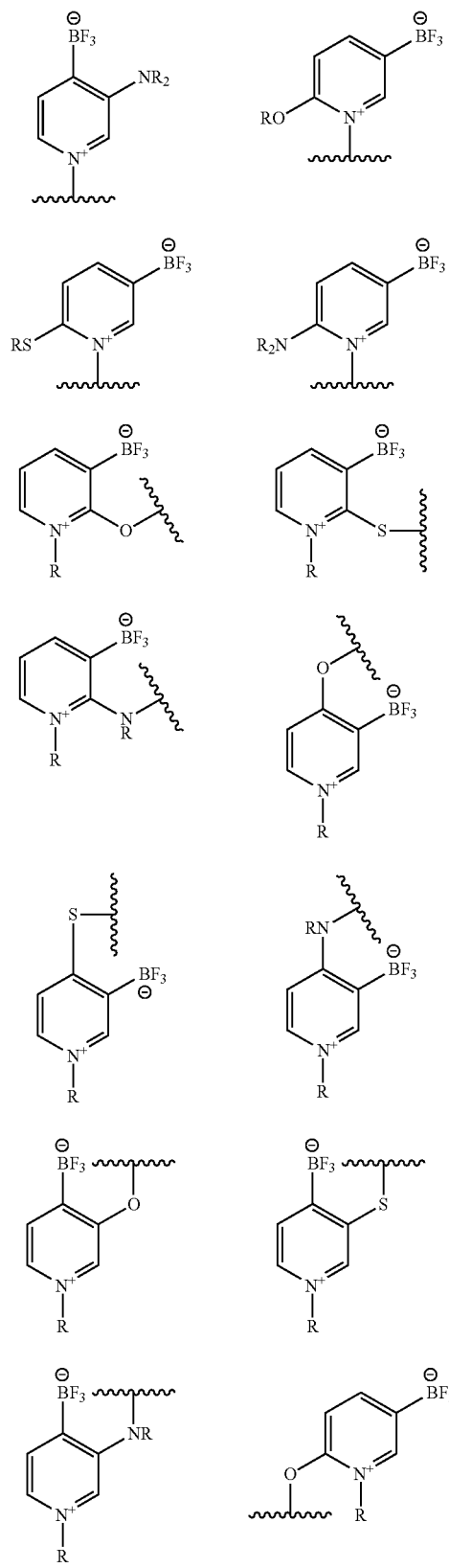
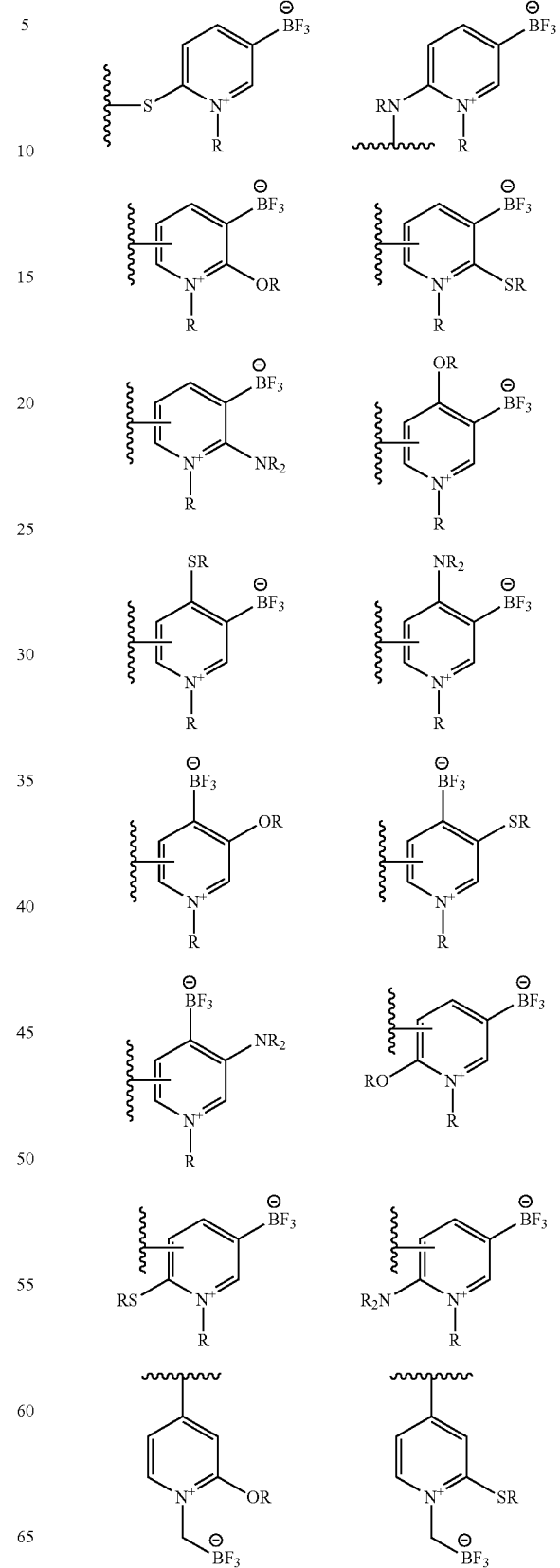

TABLE 4-continued
Exemplary BF$_3$—R$^5$— groups.
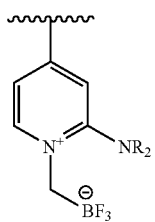 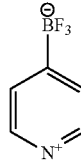
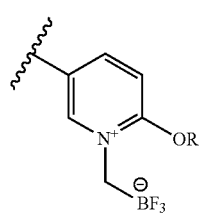 
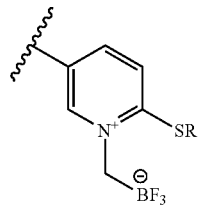 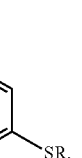
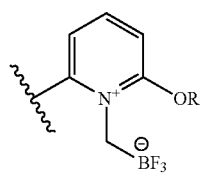 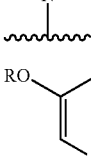
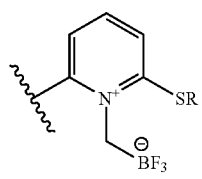 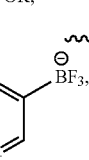
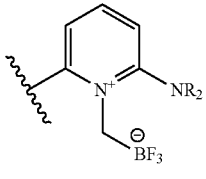 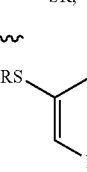
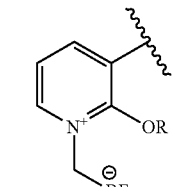 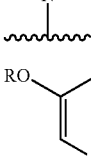
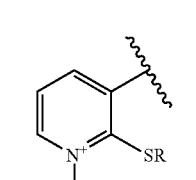 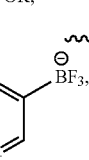
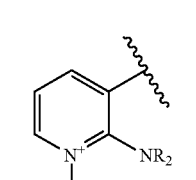 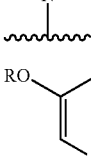
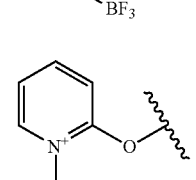 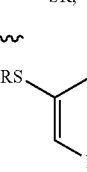
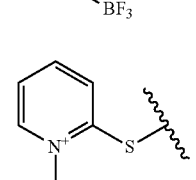 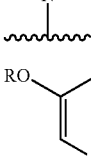
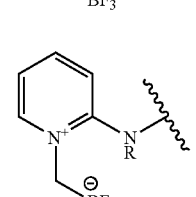 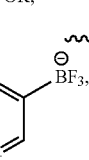
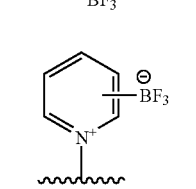 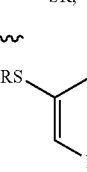
 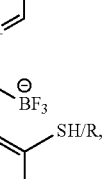
 
In some embodiments, a BF$_3$—R$^5$— may independently form

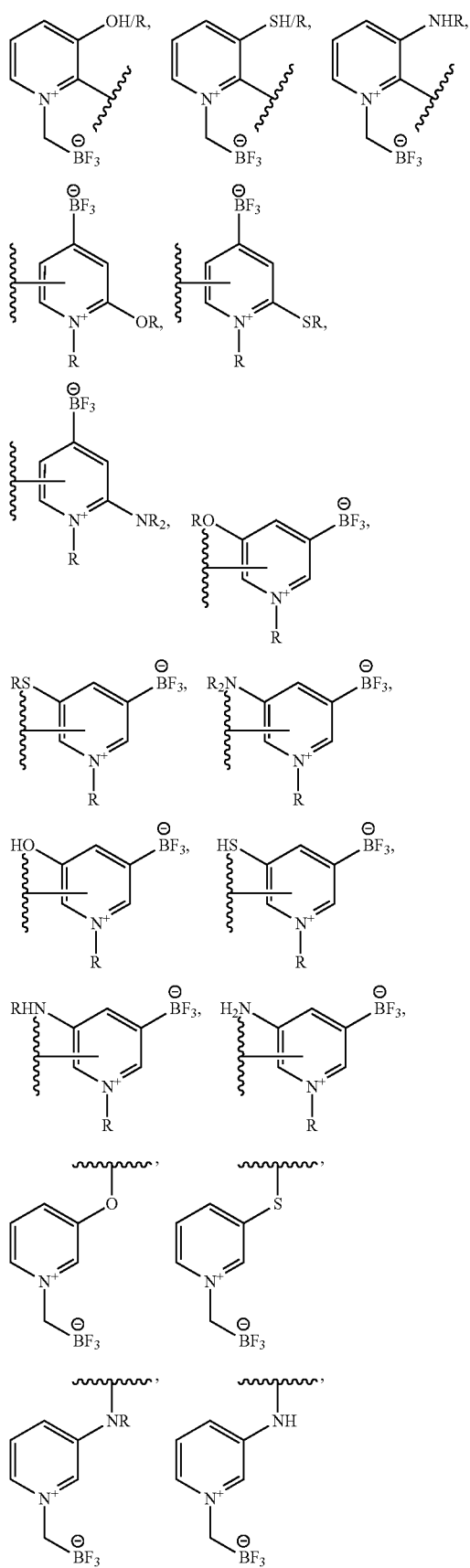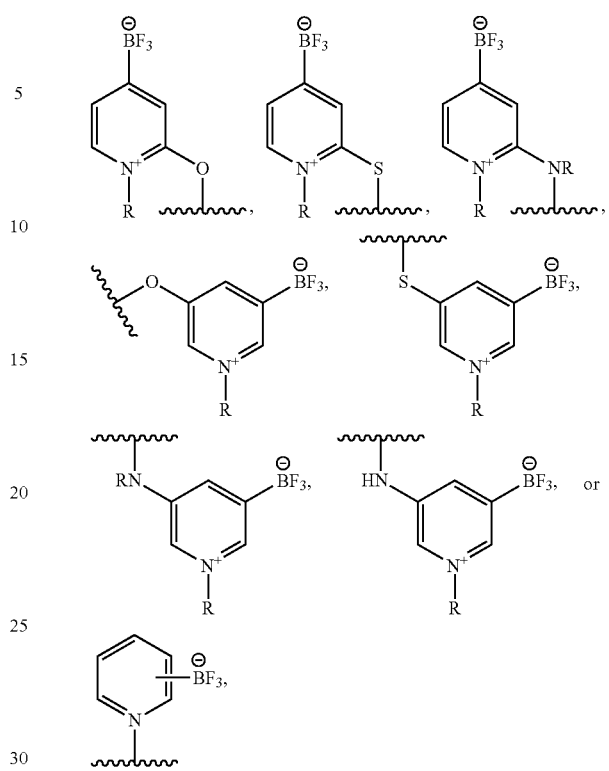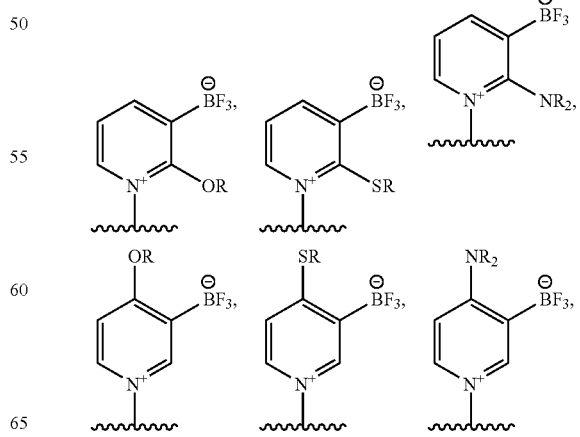

in which each R (when present) in the pyridine substituted —OR, —SR, —NR—, —NHR or —NR$_2$ is independently a linear or branched $C_1$-$C_5$ alkyl. In some embodiments, R is methyl. In some embodiments, R is ethyl. In some embodiments, R is propyl. In some embodiments, R is isopropyl. In some embodiments, R is n-butyl. The trifluoroborate-containing prosthetic group(s) may comprise $^{18}$F. In some embodiments, one fluorine is a BF$_3$—R$^5$— is $^{18}$F. In some embodiments, all three fluorines in a BF$_3$—R$^5$— are $^{18}$F. In some embodiments, all three fluorines in a BF$_3$—R$^5$— are $^{19}$F.

In some embodiments, a BF$_3$—R$^5$— may independently form

-continued
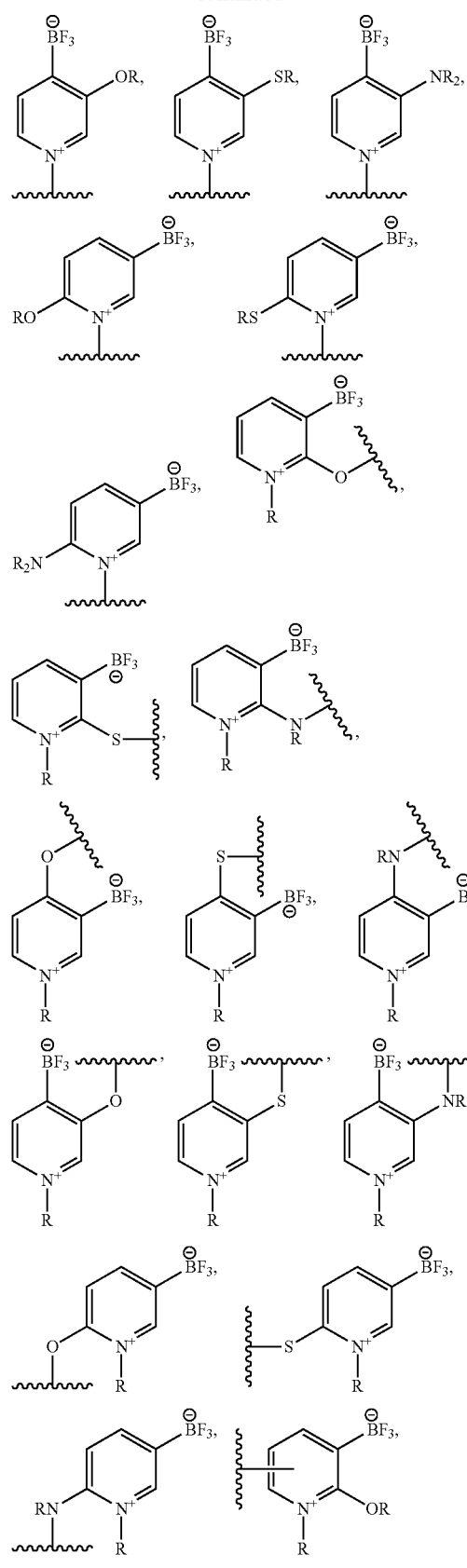
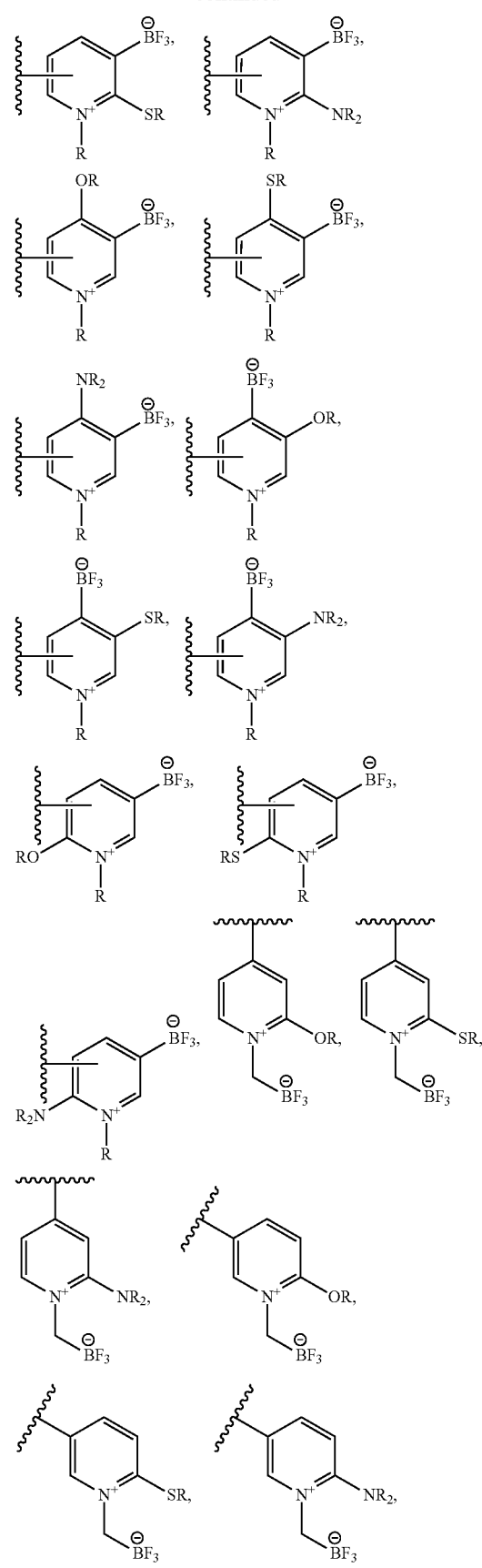

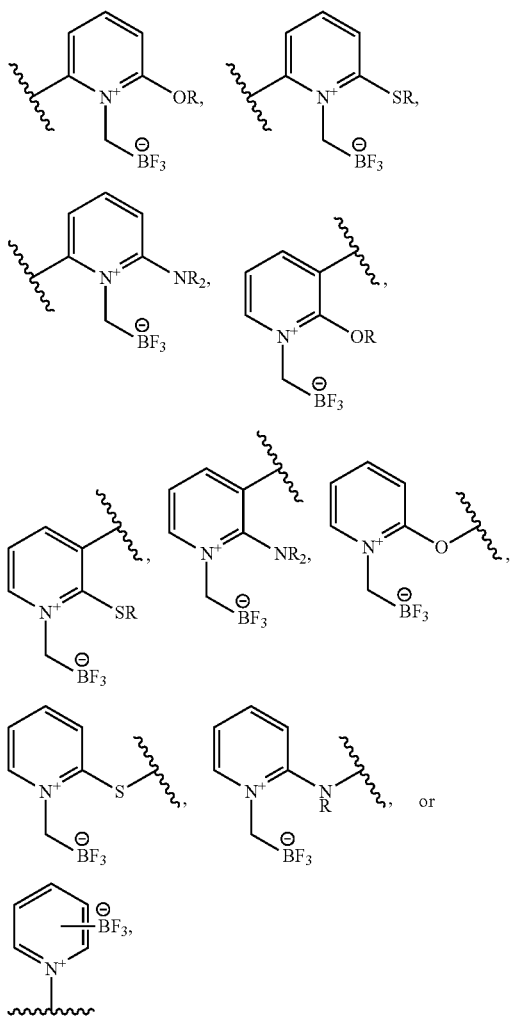

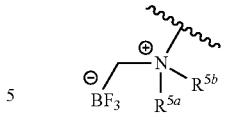

wherein $R^{5a}$ and $R^{5b}$ are each independently a $C_1$-$C_5$ linear or branched alkyl group. In some embodiments, $R^{5a}$ is methyl. In some embodiments, $R^{5a}$ is ethyl. In some embodiments, $R^{5a}$ is propyl. In some embodiments, $R^{5a}$ is isopropyl. In some embodiments, $R^{5a}$ is butyl. In some embodiments, $R^{5a}$ is n-butyl. In some embodiments, $R^{5a}$ is pentyl. In some embodiments, $R^{5b}$ is methyl. In some embodiments, $R^{5b}$ is ethyl. In some embodiments, $R^{5b}$ is propyl. In some embodiments, $R^{5b}$ is isopropyl. In some embodiments, $R^{5b}$ is butyl. In some embodiments, $R^{5b}$ is n-butyl. In some embodiments, $R^{5b}$ is pentyl. In some embodiments, $R^{5a}$ and $R^{5b}$ are both methyl. The trifluoroborate-containing prosthetic group may comprise $^{18}F$. In some embodiments, one fluorine in $BF_3$—$R^5$— is $^{18}F$. In some embodiments, all three fluorines in $BF_3$—$R^5$— are $^{18}F$. In some embodiments, all three fluorines in $BF_3$—$R^5$— are $^{19}F$.

In certain embodiments, the compound is conjugated with a radionuclide for positron emission tomography (PET) or single photon emission computed tomography (SPECT) imaging of GRPR expressing tumors, wherein the compound is conjugated with a radionuclide that is a positron emitter or a gamma emitter. Without limitation, the positron or gamma emitting radionuclide is $^{68}Ga$, $^{67}Ga$, $^{61}Cu$, $^{64}Cu$, $^{67}Ga$, $^{99m}Tc$, $^{110m}In$, $^{111}In$, $^{44}Sc$, $^{86}Y$, $^{89}Zr$, $^{90}Nb$, $^{152}Tb$, $^{155}Tb$, $^{18}F$, $^{131}I$, $^{123}I$, $^{124}I$, $^{203}Pb$ and $^{72}As$.

In certain embodiments the compound is conjugated with a radionuclide that is used for therapy. This includes radioisotopes such as $^{165}Er$, $^{212}Bi$, $^{211}At$, $^{166}Ho$, $^{149}Pm$, $^{159}Gd$, $^{105}Rh$, $^{109}Pd$, $^{198}Au$, $^{199}Au$, $^{175}Yb$, $^{142}Pr$, $^{177}Lu$, $^{111}In$, $^{213}Bi$, $^{47}Sc$, $^{90}Y$, $^{225}Ac$, $^{117m}Sn$, $^{153}Sm$, $^{149}Tb$, $^{161}Tb$, $^{165}Er$, $^{213}Bi$, $^{224}Ra$, $^{223}Ra$, $^{212}Bi$, $^{212}Pb$, $^{225}Ac$, $^{227}Th$, $^{223}Ra$, $^{47}Sc$, $^{77}As$, $^{186}Re$, $^{188}Re$, $^{64}Cu$ or $^{67}Cu$.

In some embodiments, n6 is 1, and the linker and $R^L$ together form a p-aminomethylaniline-diglycolic acid (pABzA-DIG) linker, a 4-amino-(1-carboxymethyl)piperidine (Pip) linker, a 9-amino-4,7-dioxanonanoic acid (dPEG2) linker, or a 4-(2-aminoethyl)-1-carboxymethylpiperazine (Acp) linker. In some embodiments, the linker and $R^L$ together form:

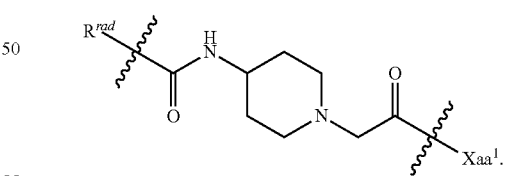

In some embodiments, the compound is LW01025, optionally conjugated by a radiometal. In some embodiments, the compound is LW01029, optionally conjugated by a radiometal. In some embodiments, the compound is LW01107, optionally conjugated by a radiometal. In some embodiments, the compound is LW01108, optionally conjugated by a radiometal. In some embodiments, the compound is LW01110, optionally conjugated by a radiometal. In some embodiments, the compound is LW01102, optionally conjugated by a radiometal. In some embodiments, the compound is LW01142, optionally conjugated by a radioin which each R (when present) in the pyridine substituted —OR, —SR, —NR—, —NHR or —$NR_2$ is independently a linear or branched $C_1$-$C_5$ alkyl. In some embodiments, R is methyl. In some embodiments, R is ethyl. In some embodiments, R is propyl. In some embodiments, R is isopropyl. In some embodiments, R is n-butyl. In some embodiments, a $BF_3$—$R^5$— is

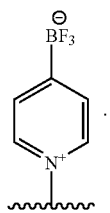

In some embodiments, all three fluorines in a $BF_3$—$R^5$— are $^{18}F$. In some embodiments, one fluorine in a $BF_3$—$R^5$— is $^{18}F$. In some embodiments, all three fluorines in a $BF_3$—$R^5$— are $^{19}F$.

In some embodiments, at least one $BF_3$—$R^5$— or optionally each $BF_3$—$R^5$— is independently metal. In some embodiments, the compound is LW01158, optionally conjugated by a radiometal. In some embodiments, the compound is LW01186, optionally conjugated by a radiometal.

In some embodiments, the compound is LW02002, optionally conjugated by a radiometal. In some embodiments, the compound is LW02021, optionally conjugated by a radiometal. In some embodiments, the compound is LW02023, optionally conjugated by a radiometal. In some embodiments, the compound is LW02025, optionally conjugated by a radiometal.

In some embodiments, the compound is LW01045, optionally conjugated by a radiometal. In some embodiments, the compound is LW01059, optionally conjugated by a radiometal. In some embodiments, the compound is LW01061, optionally conjugated by a radiometal. In some embodiments, the compound is LW01090, optionally conjugated by a radiometal. In some embodiments, the compound is LW01117, optionally conjugated by a radiometal.

In some embodiments, the compound is:
- LW01025 (DOTA-Pip-D-Phe-Gln-Trp-Ala-Val-Gly-His-Leu-Thz-NH$_2$);
- LW01029 (DOTA-Pip-D-2-Nal-Gln-Trp-Ala-Val-Gly-His-Leu-Thz-NH$_2$);
- LW01107 (DOTA-Pip-D-Phe-Gln-Trp-Ala-Val-Gly-NMe-His-Leu-Thz-NH$_2$);
- LW01108 (DOTA-Pip-D-Phe-Gln-Trp-Ala-Tle-Gly-His-Leu-Thz-NH$_2$);
- LW01110 (DOTA-Pip-D-Phe-Gln-Trp-Ala-Tle-Gly-NMe-His-Leu-Thz-NH$_2$);
- LW01142 (DOTA-Pip-D-Phe-His-Trp-Ala-Tle-Gly-NMe-His-Leu-Thz-NH$_2$);
- LW01102 (DOTA-Pip-D-Phe-His-Trp-Ala-Val-Gly-His-LeuψThz-NH$_2$);
- LW01158 (DOTA-Pip-D-Phe-Gln-Trp-Ala-Tle-Gly-His-LeuψThz-NH$_2$);
- LW01080 (D-Phe-Gln-Trp-Ala-Tle-Gly-His-Leu-Thz-NH$_2$);
- LW01085 (D-Phe-Gln-Trp-Ala-Val-Gly-His-Leu-Thz-NH$_2$);
- LW01088 (D-Phe-Gln-Trp-Ala-Val-Gly-NMe-His-Leu-Thz-NH$_2$);
- LW01136 (D-Phe-Gln-Trp(Me)-Ala-Val-Gly-His-Leu-Thz-NH$_2$);
- LW01186 (DOTA-Pip-D-Phe-Gln-αMe-Trp-Ala-Tle-Gly-His-LeuψThz-NH$_2$);
- LW02002 (DOTA-Pip-D-Phe-Gln-Trp-Ala-Tle-N-Me-Gly-His-LeuψThz-NH$_2$);
- LW02021 (DOTA-Pip-D-Phe-Gln-7-F-Trp-Ala-Val-Gly-His-Leu-Thz-NH$_2$);
- LW01142 (DOTA-Pip-D-Phe-His-Trp-Ala-Tle-Gly-NMe-His-Leu-Thz-NH$_2$);
- LW02023 (DOTA-Pip-D-Phe-Gln-5-Me-Trp-Ala-Val-Gly-His-Leu-Thz-NH$_2$);
- LW02025 (DOTA-Pip-D-Phe-Gln-2-Me-Trp-Ala-Val-Gly-His-Leu-Thz-NH$_2$);
- LW02045 (DOTA-Pip-D-Phe-Gln-Trp-Ala-Val-N-MeGly-His-LeuψPro-NH$_2$);
- LW02042 (DOTA-Pip-D-Phe-Gln-Trp-Ala-Val-Gly-His-Phe-Thz-NH$_2$);
- LW02011 (D-Phe-Gln-Trp-Ala-2,3-dehydro-Val-Gly-His-Leu-Thz-NH$_2$);
- LW02016 (D-Phe-Gln-Trp-Ala-L-cyclopropylycine-Gly-His-Leu-Thz-NH$_2$);
- LW02019 (D-Phe-Gln-Trp-Ala-cyclobutaneacetic acid-Gly-His-Leu-Thz-NH$_2$);
- LW01166 (D-Phe-Gln-5-F-Trp-Ala-Val-Gly-His-Leu-Thz-NH$_2$);
- LW01171 (D-Phe-Gln-6-Me-Trp-Ala-Val-Gly-His-Leu-Thz-NH$_2$);
- LW01173 (D-Phe-Gln-5-OH-Trp-Ala-Val-Gly-His-Leu-Thz-NH$_2$);
- LW01175 (D-Phe-Gln-6-F-Trp-Ala-Val-Gly-His-Leu-Thz-NH$_2$);
- LW01177 (D-Phe-Gln-7-F-Trp-Ala-Val-Gly-His-Leu-Thz-NH$_2$);
- LW01180 (D-Phe-Gln-4-F-Trp-Ala-Val-Gly-His-Leu-Thz-NH$_2$);
- LW01182 (D-Phe-Gln-5-Me-Trp-Ala-Val-Gly-His-Leu-Thz-NH$_2$);
- LW01183 (D-Phe-Gln-4-Me-Trp-Ala-Val-Gly-His-Leu-Thz-NH$_2$);
- LW01191 (D-Phe-Gln-D-Tpi-Ala-Val-Gly-His-Leu-Thz-NH$_2$);
- LW02007 (D-Phe-Gln-7-Me-Trp-Ala-Val-Gly-His-Leu-Thz-NH$_2$);
- LW02009 (D-Phe-Gln-2-Me-Trp-Ala-Val-Gly-His-Leu-Thz-NH$_2$);
- LW02013 (D-Phe-Gln-7-Aza-Trp-Ala-Val-Gly-His-Leu-Thz-NH$_2$); or
- LW02015 (D-Phe-Gln-Bta-Ala-Val-Gly-His-Leu-Thz-NH$_2$), wherein ψ for these compounds is a reduced peptide bond.

In another embodiment, the compound is:
- LW01080* (DOTA-Pip-D-Phe-Gln-Trp-Ala-Tle-Gly-His-Leu-Thz-NH$_2$);
- LW01085* (DOTA-Pip-D-Phe-Gln-Trp-Ala-Val-Gly-His-Leu-Thz-NH$_2$);
- LW01088* (DOTA-Pip-D-Phe-Gln-Trp-Ala-Val-Gly-NMe-His-Leu-Thz-NH$_2$);
- LW01136* (DOTA-Pip-D-Phe-Gln-Trp(Me)-Ala-Val-Gly-His-Leu-Thz-NH$_2$);
- LW02011* (DOTA-Pip-D-Phe-Gln-Trp-Ala-2,3-dehydro-Val-Gly-His-Leu-Thz-NH$_2$);
- LW02016* (DOTA-Pip-D-Phe-Gln-Trp-Ala-L-cyclopropylycine-Gly-His-Leu-Thz-NH$_2$);
- LW02019* (DOTA-Pip-D-Phe-Gln-Trp-Ala-cyclobutaneacetic acid-Gly-His-Leu-Thz-NH$_2$);
- LW01166* (DOTA-Pip-D-Phe-Gln-5-F-Trp-Ala-Val-Gly-His-Leu-Thz-NH$_2$);
- LW01171* (DOTA-Pip-D-Phe-Gln-6-Me-Trp-Ala-Val-Gly-His-Leu-Thz-NH$_2$);
- LW01173* (DOTA-Pip-D-Phe-Gln-5-OH-Trp-Ala-Val-Gly-His-Leu-Thz-NH$_2$);
- LW01175* (DOTA-Pip-D-Phe-Gln-6-F-Trp-Ala-Val-Gly-His-Leu-Thz-NH$_2$);
- LW01177* (DOTA-Pip-D-Phe-Gln-7-F-Trp-Ala-Val-Gly-His-Leu-Thz-NH$_2$);
- LW01180* (DOTA-Pip-D-Phe-Gln-4-F-Trp-Ala-Val-Gly-His-Leu-Thz-NH$_2$);
- LW01182* (DOTA-Pip-D-Phe-Gln-5-Me-Trp-Ala-Val-Gly-His-Leu-Thz-NH$_2$);
- LW01183 (DOTA-Pip-D-Phe-Gln-4-Me-Trp-Ala-Val-Gly-His-Leu-Thz-NH$_2$);
- LW01191* (DOTA-Pip-D-Phe-Gln-D-Tpi-Ala-Val-Gly-His-Leu-Thz-NH$_2$);
- LW02007* (DOTA-Pip-D-Phe-Gln-7-Me-Trp-Ala-Val-Gly-His-Leu-Thz-NH$_2$);
- LW02009*(DOTA-Pip-D-Phe-Gln-2-Me-Trp-Ala-Val-Gly-His-Leu-Thz-NH$_2$);
- LW02013* (DOTA-Pip-D-Phe-Gln-7-Aza-Trp-Ala-Val-Gly-His-Leu-Thz-NH$_2$); or LW02015* (DOTA-Pip-D-Phe-Gln-Bta-Ala-Val-Gly-His-Leu-Thz-NH$_2$), wherein ψ for these compounds is a reduced peptide bond.

In another embodiment, the compound is:

LW01045 (DOTA-Pip-D-Phe-Gln-Trp-Ala-Val-Gly-His-Leu-ψ-Thz-NH$_2$),

LW01059 (DOTA-Pip-D-2-Nal-Gln-Trp-Ala-Val-Gly-His-Leu-ψ-Thz-NH$_2$),

LW01061 (DOTA-Pip-D-Tpi-Gln-Trp-Ala-Val-Gly-His-Leu-ψ-Thz-NH$_2$),

LW01090 (DOTA-Pip-D-Phe-Gln-Trp-Ala-Val-NMe-Gly-His-Leu-ψ-Thz-NH$_2$), or

LW01117 (DOTA-Cysteic acid-Pip-D-2-Nal-Gln-Trp-Ala-Val-Gly-His-Leu-ψ-Thz-NH$_2$), wherein ip for these compounds is a reduced peptide bond.

In another specific embodiment, the LW0 compounds listed above and described herein may be included in a pharmaceutical composition. In a specific embodiment, the pharmaceutical composition may include one or more compounds from LW0 compounds listed above and described herein or Formula I, A, or B and a pharmaceutically acceptable carrier. In another specific embodiment, the compound(s) may be bound to or include a radiometal. In a specific embodiment, the radiometal is $^{165}$Er, $^{212}$Bi, $^{211}$At, $^{166}$Ho, $^{149}$Pm, $^{159}$Gd, $^{105}$Rh, $^{109}$Pd, $^{198}$Au, $^{199}$Au, $^{175}$Yb, $^{142}$Pr, $^{177}$Lu, $^{111}$In, $^{213}$Bi, $^{47}$Sc, $^{90}$Y, $^{225}$Ac, $^{117m}$Sn, $^{153}$Sm, $^{149}$Tb, $^{161}$Tb, $^{224}$Ra, $^{223}$Ra, $^{212}$Pb, $^{227}$Th, $^{223}$Ra, $^{77}$As, $^{186}$Re, $^{188}$Re, $^{67}$Cu, or $^{64}$Cu.

In a specific embodiment, the LW0 compounds listed above and described herein, may used for imaging methods. In a specific embodiment, the methods may include imaging Gastrin-releasing peptide receptor (GRPR) in a subject, the method comprising: administering to the subject a peptidic compound, including the LW0 compounds listed above and described herein, and/or any compound of Formulas I, A or B; and imaging tissue of the subject. In a specific embodiment, the methods may include the methods of treating cancer in a subject comprising, administering to the subject in need thereof a peptidic compound including the LW0 compounds listed above and described herein, and/or any compound of Formulas I, A or B.

In another specific embodiment, the methods may include treating a GRPR-expressing condition or disease. In a specific embodiment, the GRPR-expressing condition or disease may be a psychiatric disorder, neurological disorder, inflammatory disease, prostate cancer, lung cancer, head and neck cancer, colon cancer, kidney cancer, ovarian cancer, liver cancer, pancreatic cancer, breast cancer, glioma or neuroblastoma. In some embodiments, the cancer is prostate cancer.

In some embodiments, the compounds described herein are optionally conjugated by a radiometal, and may be used for the methods described herein.

In alternative embodiments, the radiometal is $^{177}$Lu, $^{111}$In, $^{213}$Bi, $^{68}$Ga, $^{67}$Ga, $^{203}$Pb, $^{212}$Pb, $^{44}$Sc, $^{47}$Sb, $^{90}$Y, $^{86}$Y, $^{225}$Ac, $^{117m}$Sn, $^{153}$Sm, $^{149}$Tb, $^{152}$Tb, $^{155}$Tb, $^{161}$Tb, $^{165}$Er, $^{213}$Bi, $^{224}$Ra, $^{212}$Bi, $^{212}$Pb, $^{225}$Ac, $^{227}$Th, $^{223}$Ra, $^{47}$Sc, $^{64}$Cu or $^{67}$Cu. In some embodiments, the radiometal is $^{68}$Ga. In some embodiments, the radiometal is $^{64}$Cu. In some embodiments, the radiometal is $^{67}$Cu. In some embodiments, the radiometal is $^{67}$Ga. In some embodiments, the radiometal is $^{111}$In. In some embodiments, the radiometal is $^{177}$Lu. In some embodiments, the radiometal is $^{90}$Y In some embodiments, the radiometal is $^{225}$Ac.

When the radiolabeling group (i.e. $R^{rad}$ in Formula I) comprises or is conjugated to a diagnostic radionuclide, there is disclosed use of certain embodiments of a compound as disclosed herein for preparation of a radiolabelled tracer for imaging GRPR-expressing tissues in a subject. There is also disclosed a method of imaging GRPR-expressing tissues in a subject, in which the method comprises: administering to the subject a composition comprising a compound described herein and a pharmaceutically acceptable excipient; and imaging tissue of the subject, e.g. using PET or SPECT. When the tissue is a diseased tissue (e.g. a GRPR-expressing cancer), GRPR-targeted treatment may then be selected for treating the subject.

When the radiolabeling group (i.e. $R^{rad}$ in Formula I) comprises or is conjugated to a therapeutic radionuclide, there is disclosed use of certain embodiments of the compound (or a pharmaceutical composition thereof) for the treatment of GRPR-expressing conditions or diseases (e.g. cancer and the like) in a subject. Accordingly, there is provided use of a compound disclosed herein in preparation of a medicament for treating a GRPR-expressing condition or disease in a subject. There is also provided a method of treating GRPR-expressing disease in a subject, in which the method comprises: administering to the subject a composition comprising the compound and a pharmaceutically acceptable excipient. For example, but without limitation, the disease may be a GRPR-expressing cancer. In a specific embodiment, the LW0 compounds listed above and described herein, may include or be conjugated to a radiometal. In a specific embodiment, the methods may include imaging Gastrin-releasing peptide receptor (GRPR) in a subject, the method comprising: administering to the subject a peptidic compound, including the LW0 compounds listed above with a radiometal and described herein, and/or any compound of Formulas I, A or B with a radiometal; and imaging tissue of the subject. In a specific embodiment, the methods may include the methods of treating cancer in a subject comprising, administering to the subject in need thereof a peptidic compound including the LW0 compounds listed above with a radiometal and described herein, and/or any compound of Formulas I, A or B with a radiometal.

Aberrant or ectopic GRPR expression has been detected in various conditions and diseases, including psychiatric/neurological disorders, inflammatory disease, and cancer (Cornelio, et al. Ann Oncol. 2007, 18:1457-1466; Bajo et al. Proc Natl Acad Sci U S A. 2002, 99:3836-3841; Koppan et al. Cancer. 1998, 83:1335-1343; Shirahige et al. Biomed Pharmacother. 1994 48:465-472; Cai et al. Int J Oncol. 1995, 6:1165-1172; Jungwirth, Eur J Cancer Part A. 1997, 33:1141-1148; Gonzalez et al., J Pharmacol Exp Ther. 200, 331 (1): 265-276; Dalm et al. PLoS One. 2017, 12 (1): e0170536; Guo et al., Curr Opin Endocrinol Diabetes Obes. 2015, 22 (1): 3-8; Ischia et al., BJU Int. 201,113 Suppl 2:40-47; Ramos-Alvarez et al. Peptide 2015, 72: 128 -144). Accordingly, without limitation, the GRPR-expressing condition or disease may be psychiatric disorder, neurological disorder, inflammatory disease, prostate cancer, lung cancer, head and neck cancer, colon cancer, kidney cancer, ovarian cancer, liver cancer, pancreatic cancer, breast cancer, glioma or neuroblastoma. In some embodiments, the cancer is prostate cancer.

The compounds presented herein incorporate peptides, which may be synthesized by any of a variety of methods established in the art. This includes but is not limited to liquid-phase as well as solid-phase peptide synthesis using methods employing 9-fluorenylmethoxycarbonyl (Fmoc) and/or t-butyloxycarbonyl (Boc) chemistries, and/or other synthetic approaches.

Solid-phase peptide synthesis methods and technology are well-established in the art. For example, peptides may be synthesized by sequential incorporation of the amino acid residues of interest one at a time. In such methods, peptide synthesis is typically initiated by attaching the C-terminal amino acid of the peptide of interest to a suitable resin. Prior to this, reactive side chain and alpha amino groups of the amino acids are protected from reaction by suitable protecting groups, allowing only the alpha carboxyl group to react with a functional group such as an amine group, a hydroxyl group, or an alkyl halide group on the solid support. Following coupling of the C-terminal amino acid to the support, the protecting group on the side chain and/or the alpha amino group of the amino acid is selectively removed, allowing the coupling of the next amino acid of interest. This process is repeated until the desired peptide is fully synthesized, at which point the peptide can be cleaved from the support and purified. A non-limiting example of an instrument for solid-phase peptide synthesis is the Aapptec Endeavor 90 peptide synthesizer.

To allow coupling of additional amino acids, Fmoc protecting groups may be removed from the amino acid on the solid support, e.g. under mild basic conditions, such as piperidine (20-50% v/v) in DMF. The amino acid to be added must also have been activated for coupling (e.g. at the alpha carboxylate). Non-limiting examples of activating reagents include without limitation 2-(1H-benzotriazol-1-yl)-1,1,3,3-tetramethyluronium hexafluorophosphate (HBTU), 2-(1H-benzotriazol-1-yl)-1,1,3,3-tetramethyluronium tetrafluoroborate (TBTU), 2-(7-Aza-1H-benzotriazole-1-yl)-1,1,3,3-tetramethyluronium hexafluorophosphate (HATU), benzotriazole-1-yl-oxy-tris(dimethylamino)phosphoniumhexafluorophosphate (BOP), benzotriazole-1-yl-oxy-tris(pyrrolidino)phosphoniumhexafluorophosphate (PyBOP). Racemization is minimized by using triazoles, such as 1-hydroxy-benzotriazole (HOBt) and 1-hydroxy-7-azabenzotriazole (HOAt). Coupling may be performed in the presence of a suitable base, such as N,N-diisopropylethylamine (DIPEA/DIEA) and the like.

Apart from forming typical peptide bonds to elongate a peptide, peptides may be elongated in a branched fashion by attaching to side chain functional groups (e.g. carboxylic acid groups or amino groups), either: side chain to side chain; or side chain to backbone amino or carboxylate. Coupling to amino acid side chains may be performed by any known method, and may be performed on-resin or off-resin. Non-limiting examples include: forming an amide between an amino acid side chain containing a carboxyl group (e.g. Asp, D-Asp, Glu, D-Glu, and the like) and an amino acid side chain containing an amino group (e.g. Lys, D-Lys, Orn, D-Orn, Dab, D-Dab, Dap, D-Dap, and the like) or the peptide N-terminus; forming an amide between an amino acid side chain containing an amino group (e.g. Lys, D-Lys, Orn, D-Orn, Dab, D-Dab, Dap, D-Dap, and the like) and either an amino acid side chain containing a carboxyl group (e.g. Asp, D-Asp, Glu, D-Glu, and the like) or the peptide C-terminus; and forming a 1,2,3-triazole via click chemistry between an amino acid side chain containing an azide group (e.g. Lys($N_3$), D-Lys($N_3$), and the like) and an alkyne group (e.g. Pra, D-Pra, and the like). The protecting groups on the appropriate functional groups must be selectively removed before amide bond formation, whereas the reaction between an alkyne and an azido groups via the click reaction to form an 1,2,3-triazole does not require selective deprotection. Non-limiting examples of selectively removable protecting groups include 2-phenylisopropyl esters (O-2-PhiPr) (e.g. on Asp/Glu) as well as 4-methyltrityl (Mtt), allyloxycarbonyl (alloc), 1-(4,4-dimethyl-2,6-dioxocyclohex-1-ylidene))ethyl (Dde), and 1-(4,4-dimethyl-2,6-dioxocyclohex-1-ylidene)-3-methylbutyl (ivDde) (e.g. on Lys/Orn/Dab/Dap). O-2-PhiPr and Mtt protecting groups can be selectively deprotected under mild acidic conditions, such as 2.5% trifluoroacetic acid (TFA) in DCM. Alloc protecting groups can be selectively deprotected using tetrakis(triphenylphosphine)palladium(O) and phenyl silane in DCM. Dde and ivDde protecting groups can be selectively deprotected using 2-5% of hydrazine in DMF. Deprotected side chains of Asp/Glu (L- or D-forms) and Lys/Orn/Dab/Dap (L- or D-forms) can then be coupled, e.g. by using the coupling reaction conditions described above. The above provides means for including multiple $BF_3$ groups.

Peptide backbone amides may be N-methylated (i.e. alpha amino methylated) or N-alkylated. This may be achieved by directly using Fmoc-N-methylated (or Fmoc-N-alkylated) amino acids during peptide synthesis. Alternatively, N-methylation under Mitsunobu conditions may be performed. First, a free primary amine group is protected using a solution of 4-nitrobenzenesulfonyl chloride (Ns-Cl) and 2,4,6-trimethylpyridine (collidine) in NMP. N-methylation (or N-alkylation) may then be achieved in the presence of triphenylphosphine, diisopropyl azodicarboxylate (DIAD) and methanol. Subsequently, N-deprotection may be performed using mercaptoethanol and 1,8-diazabicyclo[5.4.0]undec-7-ene (DBU) in NMP. For coupling protected amino acids to N-methylated (or N-alkylated) alpha amino groups, HATU, HOAt and DIEA may be used.

The formation of the thioether (—S—) linkages (e.g. for L 1) can be achieved either on solid phase or in solution phase. For example, the formation of thioether (—S—) linkage can be achieved by coupling between a thiol-containing compound (such as the thiol group on cysteine side chain) and an alkyl halide (such as 3-(Fmoc-amino)propyl bromide and the like) in an appropriate solvent (such as N,N-dimethylformamide and the like) in the presence of base (such as N,N-diisopropylethylamine and the like). If the reactions are carried out in solution phase, the reactants used are preferably in equivalent molar ratio (1 to 1), and the desired products can be purified by flash column chromatography or high performance liquid chromatography (HPLC). If the reactions are carried out on solid phase, meaning one reactant has been attached to a solid phase, then the other reactant is normally used in excess amount (≥3 equivalents of the reactant attached to the solid phase). After the reactions, the excess unreacted reactant and reagents can be removed by sequentially washing the solid phase (resin) using a combination of solvents, such as N,N-dimethylformamide, methanol and dichloromethane, for example.

The formation of the linkage (e.g. for L 1) between a thiol group and a maleimide group can be performed using the conditions described above for the formation of the thioether (—S—) linkage simply by replacing the alkyl halide with a maleimide-containing compounds. Similarly, this reaction can be conducted in solid phase or solution phase. If the reactions are carried out in solution phase, the reactants used are preferably in equivalent molar ratio (1 to 1), and the desired products can be purified by flash column chromatography or high performance liquid chromatography (HPLC). If the reactions are carried out on solid phase, meaning one reactant has been attached to a solid phase, then the other reactant is normally used in excess amount (≥3 equivalents of the reactant attached to the solid phase). After the reactions, the excess unreacted reactant and reagents can be removed by sequentially washing the solid phase (resin) using a combination of solvents, such as N,N-dimethylformamide, methanol and dichloromethane, for example.

Urea or thiourea linkages can be made from reaction of an amine group with an isocyanate or an isothiocyanate, respectively, which are common functional groups on radiometal chelators. The isothiocyanate functional group may be added to the radiometal chelator by reacting an amino group on the chelator with thiophosgene [i.e. $C(S)Cl_2$]. Similarly, the isocyanate functional group may be added to the radiometal chelator by reacting an amino group on the chelator with phosgene [i.e. $C(O)Cl_2$].

Non-peptide moieties (e.g. radiolabeling groups and/or albumin binders) may be coupled to the peptide N-terminus while the peptide is attached to the solid support. This is facile when the non-peptide moiety comprises an activated carboxylate (and protected groups if necessary) so that coupling can be performed on resin. For example, but without limitation, a bifunctional chelator, such as 1,4,7,10-tetraazacyclododecane-1,4,7,10-tetraacetic acid (DOTA) tris (tert-butyl ester) may be activated in the presence of N-hydroxysuccinimide (NHS) and N,N'-dicyclohexylcarbodiimide (DCC) for coupling to a peptide. Alternatively, a non-peptide moiety may be incorporated into the compound via a copper-catalyzed click reaction under either liquid or solid phase conditions. Copper-catalyzed click reactions are well established in the art. For example, 2-azidoacetic acid is first activated by NHS and DCC and coupled to a peptide. Then, an alkyne-containing non-peptide moiety may be clicked to the azide-containing peptide in the presence of $Cu^{2+}$ and sodium ascorbate in water and organic solvent, such as acetonitrile (ACN) and DMF and the like. Non-peptide moieties may also be added in solution phase, which is routinely performed.

The synthesis of radiometal chelators is well-known and many chelators are commercially available (e.g. from Sigma-Aldrich™/Milipore Sigma™ and others). Protocols for conjugation of radiometals to the chelators is also well known (e.g. see Examples, below).

The synthesis of the $BF_3$—$R^5$—$R^4$— component of the compounds can be achieved following previously reported procedures (Liu et al. Angew Chem Int Ed 2014 53:11876-11880; Liu et al. J Nucl Med 2015 55:1499-1505; Liu et al. Nat Protoc 2015 10:1423-1432; Kuo et al. J Nucl Med, 2019 60:1160-1166; each of which is incorporated by reference in its entirety). Generally, the $BF_3$-containing motif can be coupled to the linker via click chemistry by forming a 1,2,3-triazole ring between a $BF_3$-containg azido (or alkynyl) group and an alkynyl (or azido) group on the linker, or by forming an amide linkage between a $BF_3$-containg carboxylate and an amino group on the linker. To make the $BF_3$-containing azide, alkyne or carboxylate, a boronic acid ester-containing azide, alkyne or carboxylate is first prepared following by the conversion of the boronic acid ester to $BF_3$ in a mixture of HCl, DMF and $KHF_2$. For alkyl $BF_3$, the boronic acid ester-containing azide, alkyne or carboxylate can be prepared by coupling boronic acid ester-containing alkyl halide (such as iodomethylboronic acid pinacol ester) with an amine-containing azide, alkyne or carboxylate (such as N,N-dimethylpropargylamine). For aryl $BF_3$, the boronic acid ester can be prepared via Suzuki coupling using aryl halide (iodine or bromide) and bis(pinacolato)diboron.

$^{18}$F-Fluorination of the $BF_3$-containing compounds via $^{18}$F-$^{19}$F isotope exchange reaction can be achieved following previously published procedures (Liu et al. Nat Protoc 2015 10:1423-1432, incorporated by reference in its entirety). Generally, ~100 nmol of the $BF_3$-containing compound is dissolved in a mixture of 15 µl of pyridazine-HCl buffer (pH=2.0-2.5, 1 M), 15 µl of DMF and 1 µl of a 7.5 mM $KHF_2$ aqueous solution. $^{18}$F-Fluoride solution (in saline, 60 µl) is added to the reaction mixture, and the resulting solution is heated at 80° C. for 20 min. At the end of the reaction, the desired product can be purified by solid phase extraction or by reversed high performance liquid chromatography (HPLC) using a mixture of water and acetonitrile as the mobile phase.

When the peptide has been fully synthesized on the solid support, the desired peptide may be cleaved from the solid support using suitable reagents, such as TFA, tri-isopropylsilane (TIS) and water. Side chain protecting groups, such as Boc, pentamethyldihydrobenzofuran-5-sulfonyl (Pbf), trityl (Trt) and tert-butyl (tBu) are simultaneously removed (i.e. deprotection). The crude peptide may be precipitated and collected from the solution by adding cold ether followed by centrifugation. Purification and characterization of the peptides may be performed by standard separation techniques, such as high performance liquid chromatography (HPLC) based on the size, charge and polarity of the peptides. The identity of the purified peptides may be confirmed by mass spectrometry or other similar approaches. The inventions described herein are further represented by the following embodiments.

Embodiments of the Present Invention

Embodiment 1. A peptidic compound, wherein the compound has the structure of Formula I or is a salt or solvate of Formula I,

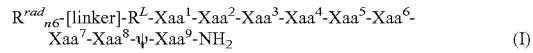

$R^{rad}_{n6}$-[linker]-$R^L$-Xaa$^1$-Xaa$^2$-Xaa$^3$-Xaa$^4$-Xaa$^5$-Xaa$^6$-Xaa$^7$-Xaa$^8$-ψ-Xaa$^9$-NH$_2$     (I)

wherein:
Xaa$^1$ is an N-terminal amino acid residue selected from D-Phe, 4-chlorophenylalanine (Cpa), D-Cpa, 3-(1-naphthyl)alanine (Nal), D-Nal, 3-(2-naphthyl)alanine (2-Nal), or D-2-Nal;

Xaa$^2$ is Asn, Gln, homoserine (Hse), citrulline (Cit) or His;

Xaa$^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(5-OH) or αMe-Trp;

Xaa$^4$ is Ala or Ser;

Xaa$^5$ is Val, Cpg (cyclopentylglycine) or tert-leucine (Tle);

Xaa$^6$ is Gly, NMe-Gly, or D-Ala;

Xaa$^7$ is His or NMe-His;

Xaa$^8$ is Leu, D-Pro, or Phe;

Xaa$^9$-NH$_2$ is a C-terminally amidated amino acid residue selected from Pro, Phe, oxazolidine-4-carboxylic acid (4-oxa-L-Pro), Me$_2$Thz (5,5-dimethyl-1,3-thiazolidine-4-carboxylic acid), or thiazoline-4-carboxylic acid (Thz);

ψ represents a peptide bond or reduced peptide bond joining Xaa$^8$ to Xaa$^9$;

excluding compounds in which Xaa$^2$, Xaa$^3$, Xaa$^5$, and Xaa$^7$ are Gln, Trp, Val, and His, respectively, in which ψ is a reduced peptide bond;

$R^L$ is —C(O)—, —NH—C(O)—, or —NH—C(S)—;

the linker is a linear or branched chain of n1 units of -L$^1$R$^1$- and/or -(L$^1$)$_2$R$^1$-, wherein:
n1 is 1-20;
each R$^1$ is, independently, a linear, branched, and/or cyclic $C_{n2}$ alkylenyl, alkenylenyl and/or alkynylenyl, wherein each n2 is independently 1-20, wherein any carbon bonded to two other carbons is optionally independently replaced by N, S, or O, and carbons are optionally independently substituted with oxo, hydroxyl, sulfhydryl, —SeH, halogen, guanidino, amine, amide, urea, carboxylic acid, sulfonic acid, sulfinic acid, or phosphoric acid;

$L^1$ bonds to carbon, wherein each $L^1$ is independently —S—, —N($R^2$)C(O)—, —C(O)N($R^2$)—, —NH—C(O)—NH—, —NH—C(S)—NH—,

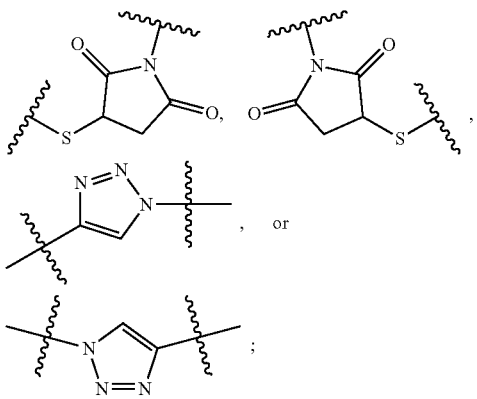

and $R^2$ is H, methyl or ethyl; and an albumin binder ($R^{alb}$) is optionally bonded to an $L^1$ of the linker, wherein the albumin binder is:
—$(CH_2)_{n3}$-$CH_3$ wherein n3 is 8-20;
—$(CH_2)_{n4}$—C(O)OH wherein n4 is 8-20;

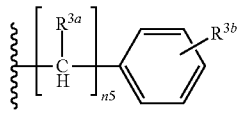

wherein n5 is 1-4 and $R^{3a}$ is H or methyl, and $R^{3b}$ is I, Br, F, Cl, H, OH, $OCH_3$, $NH_2$, $NO_2$ or $C_1$-$C_6$ alkyl; or

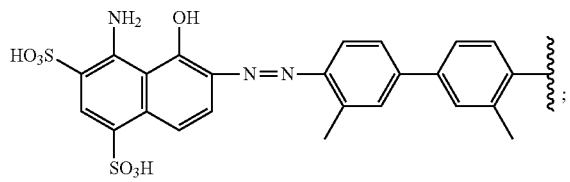 [SMILES: *c1ccc(-c2ccc(N=Nc3ccc4c(S(=O)(=O)O)cc(S(=O)(=O)O)c(N)c4c3O)c(C)c2)cc1C]

n6 is 1-5; and each $R^{rad}$ is a radiolabeling group bonded to or incorporating an $L^1$ of the linker, wherein each radiolabeling group is independently: a radiometal chelator; an aryl or heteroaryl substituted with a radiohalogen; a prosthetic group containing a trifluoroborate; a prosthetic group containing a silicon-fluorine-acceptor moiety; or a prosthetic group containing a fluorophosphate, fluorosulfate, sulfonyl fluoride, or a combination thereof.

Embodiment 2. The peptidic compound of Embodiment 1, wherein ψ is a peptide bond.

Embodiment 3. The peptidic compound of Embodiment 1 or 2, wherein $Xaa^3$ is αMe-Trp.

Embodiment 4. The peptidic compound of any one of Embodiments 1 to 3, wherein $Xaa^5$ is Tle.

Embodiment 5. The peptidic compound of any one of Embodiments 1 to 4, wherein $Xaa^7$ is NMe-His.

Embodiment 6. The peptidic compound of any one of Embodiments 1 to 5, wherein $Xaa^1$ is D-Phe or D-2-Nal.

Embodiment 7. The peptidic compound of any one of Embodiments 1 to 6, wherein $Xaa^2$ is Gln or His.

Embodiment 8. The peptidic compound of any one of Embodiments 1 to 7, wherein $Xaa^3$ is Trp.

Embodiment 9. The peptidic compound of any one of Embodiments 1 to 8, wherein $Xaa^6$ is Gly.

Embodiment 10. The peptidic compound of any one of Embodiments 1 to 9, wherein $Xaa^8$ is Leu.

Embodiment 11. The peptidic compound of any one of Embodiments 1 to 10, wherein $Xaa^9$ is Thz.

Embodiment 12. The peptidic compound of any one of Embodiments 1 to 11, wherein at least one $R^{rad}$ is a radiometal chelator, optionally selected from the group consisting of: DOTA and derivatives; DOTAGA; NOTA; NODAGA; NODASA; CB-DO2A; 3p-C-DEPA; TCMC; DO3A; DTPA and DTPA analogues optionally selected from CHX-A"-DTPA and 1B4M-DTPA; TETA; NOPO; Me-3,2-HOPO; CB-TE1A1P; CB-TE2P; MM-TE2A; DM-TE2A; sarcophagine and sarcophagine derivatives optionally selected from SarAr, SarAr-NCS, diamSar, AmBaSar, and BaBaSar; TRAP; AAZTA; DATA and DATA derivatives; H2-macropa or a derivative thereof; $H_2$dedpa, $H_4$octapa, $H_4$py4pa, $H_4$Pypa, $H_2$azapa, $H_5$decapa, and other picolinic acid derivatives; CP256; PCTA; C-NETA; C-NE3TA; HBED; SHBED; BCPA; CP256; YM103; desferrioxamine (DFO) and DFO derivatives; $H_6$phospa; a trithiol chelate; mercaptoacetyl; hydrazinonicotinamide; dimercaptosuccinic acid; 1,2-ethylenediylbis-L-cysteine diethyl ester; methylenediphosphonate; hexamethylpropyleneamineoxime; hexakis (methoxy isobutyl isonitrile), H4py4pa-phenyl-NCS, and Crown.

Embodiment 13. The peptidic compound of Embodiment 12, wherein the radiometal chelator is bound by a radiometal, a radionuclide-bound metal, or a radionuclide-bound metal-containing prosthetic group, optionally selected from the group consisting of: $^{68}$Ga, $^{61}$Cu, $^{64}$Cu, $^{67}$Cu, $^{67}$Ga, $^{111}$In, $^{44}$Sc, $^{86}$Y, $^{89}$Zr, $^{90}$Nb, $^{177}$Lu, $^{117m}$Sn, $^{165}$Er, $^{90}$Y, $^{227}$Th, $^{225}$Ac, $^{213}$Bi, $^{212}$Bi, $^{72}$As, $^{77}$As, $^{211}$At, $^{203}$Pb, $^{212}$Pb, $^{47}$Sc, $^{166}$Ho, $^{188}$Re, $^{186}$Re, $^{149}$Pm, $^{159}$Gd, $^{105}$Rh, $^{109}$Pd, $^{198}$Au, $^{199}$Au, $^{175}$Yb, $^{142}$Pr, $^{114m}$In, $^{99m}$Tc, $^{149}$Tb, $^{152}$Tb, $^{155}$Tb, $^{161}$Tb, and [$^{18}$F]AlF.

Embodiment 14. The peptidic compound of any one of Embodiments 1 to 13, wherein at least one $R^{rad}$ is a trifluoroborate containing prosthetic group $BF_3$—$R^5$—$R^4$—, wherein $R^4$ is —$(CH_2)_{1-5}$— and optionally methylene, and wherein $BF_3$—$R^5$— forms:

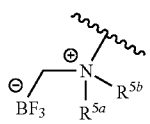

wherein $R^{5a}$ and $R^{5b}$ are each independently a $C_1$-$C_5$ linear or branched alkyl group,

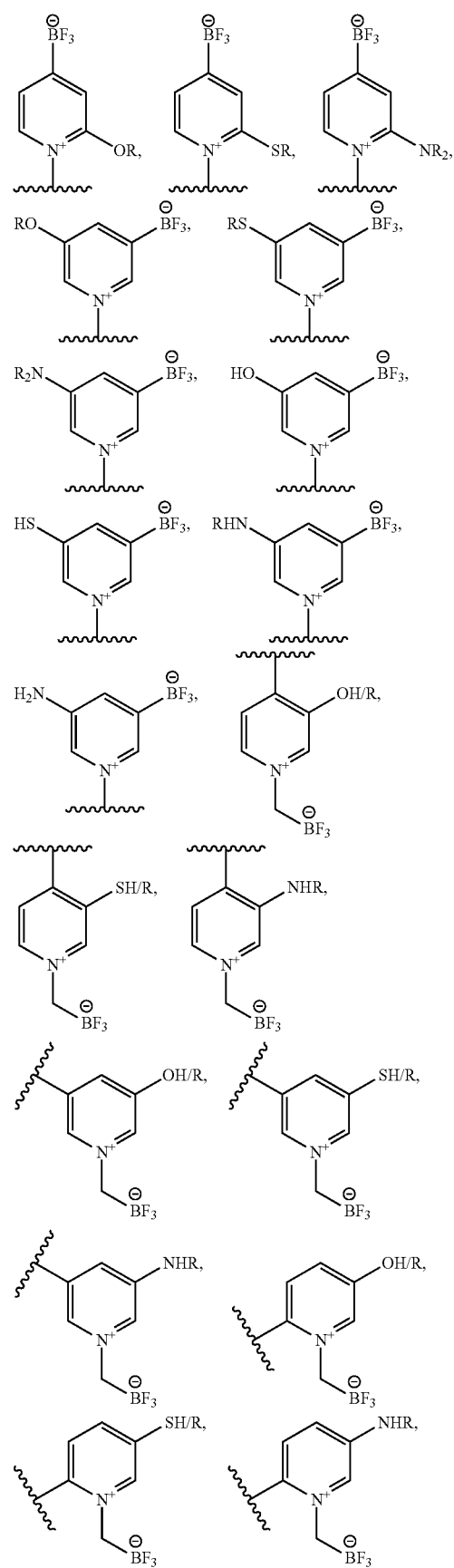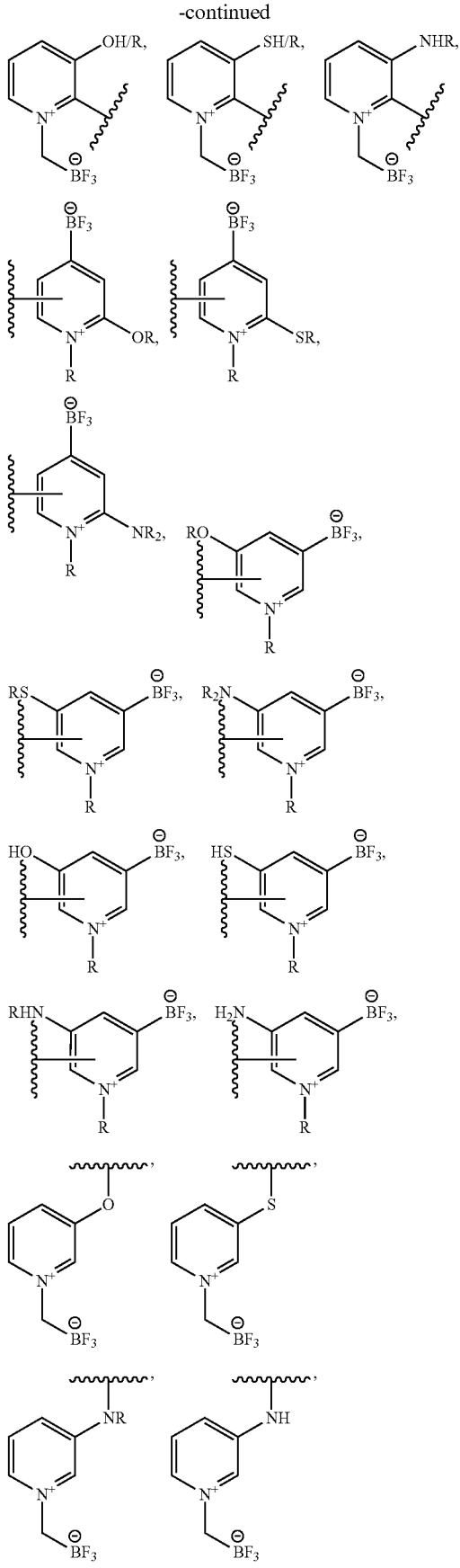

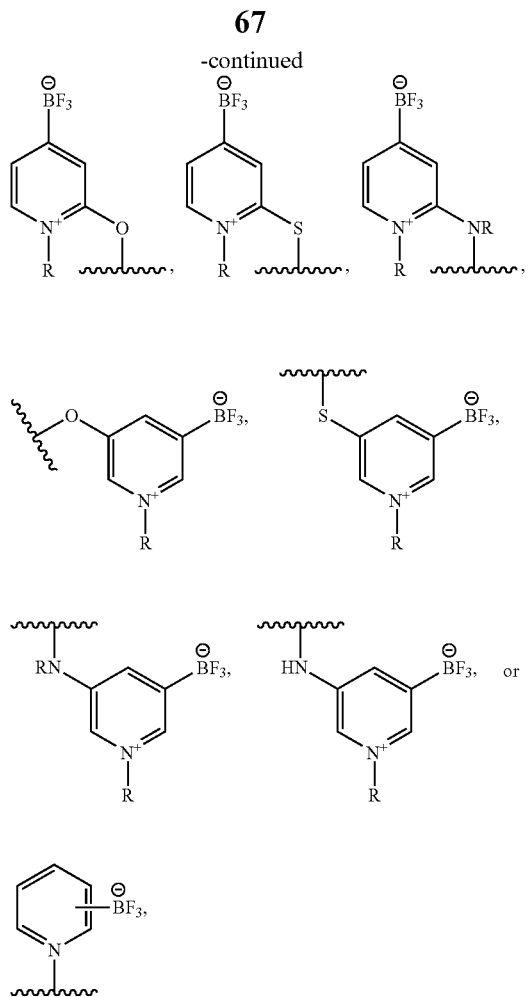
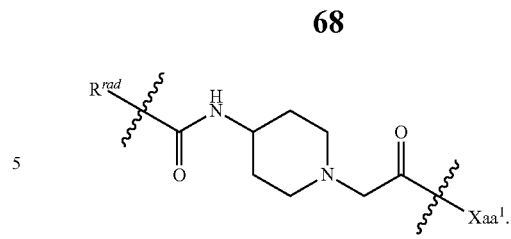

in which the R in each pyridine substituted —OR, —SR, —NR—, —NHR or —NR₂ is independently a branched or linear $C_1$-$C_5$ alkyl, optionally wherein the fluorines in $BF_3$—$R^5$—$R^4$— comprise $^{18}F$.

Embodiment 15. The peptidic compound of any one of Embodiment 1 to 11, wherein n6 is 2 and $R^{rad}_{n6}$ comprises a first $R^{rad}$ and a second $R^{rad}$, wherein the first $R^{rad}$ is a radiometal chelator as defined in Embodiment 12, optionally bound by a radiometal, a radionuclide-bound metal, or a radionuclide-bound metal-containing prosthetic group as defined in Embodiment 13, and wherein the second $R^{rad}$ is a trifluoroborate containing prosthetic group as defined in Embodiment 14 or an aryl or heteroaryl substituted with a radiofluoride.

Embodiment 16. The peptidic compound of any one of Embodiments 1 to 15, wherein the linker and $R^L$ together form a linear or branched peptide linker $(Xaa^{10})_{1-20}$, wherein each $Xaa^{10}$ is independently a proteinogenic or non-proteinogenic amino acid residue, wherein each peptide backbone amino group is independently optionally methylated, and wherein each non-proteinogenic amino acid residue is independently selected from Table 1.

Embodiment 17. The peptidic compound of any one of Embodiments 1 to 11, wherein n6 is 1, and wherein the linker and $R^L$ together form a p-aminomethylaniline-diglycolic acid (pABzA-DIG) linker, a 4-amino-(1-carboxymethyl)piperidine (Pip) linker, a 9-amino-4,7-dioxanonanoic acid (dPEG2) linker, or a 4-(2-aminoethyl)-1-carboxymethyl-piperazine (Acp) linker, optionally wherein the linker and $R^L$ together form:

The present invention will be further illustrated in the following examples:

EXAMPLE 1

General Methods

Chemicals were procured from commercial sources and used without further purification. All peptides were synthesized on an AAPPTec (Louisville, KY) Endeavor 90 peptide synthesizer. Purification and quality control of radiolabeling precursor, nonradioactive Ga-complexed standards and $^{68}$Ga-labeled peptides were performed on Agilent (Santa Clara, CA) HPLC systems equipped with a model 1200 quaternary pump, a model 1200 UV absorbance detector (set at 220 nm), and a Bioscan (Washington, DC) NaI scintillation detector. The operation of Agilent HPLC systems was controlled using the Agilent ChemStation software. HPLC columns used were a semipreparative column (Luna C18, 5 μm particle size, 100 Å pore size, 250×10 mm) and an analytical column (Luna C18, 5 μm particle size, 100 Å pore size, 250×4.6 mm) from Phenomenex (Torrance, CA). The collected HPLC eluates containing the desired peptides were lyophilized using a Labconco (Kansas City, MO) FreeZone 4.5 Plus freeze drier. Mass analyses were performed using a Waters (Milford, MA) ACQUITY QDa mass spectrometer equipped with a 2489 UV/Vis detector, and an e2695 Separations module. C18 Sep-Pak cartridges (1 cm³, 50 mg) were obtained from Waters (Milford, MA). $^{68}$Ga was eluted from an iThemba Laboratories (Somerset West, South Africa) generator and purified using a DGA resin column from Eichrom Technologies LLC (Lisle, IL). Radioactivity of $^{68}$Ga-labeled peptides was measured using a Capintec (Ramsey, NJ) CRC-25R/W dose calibrator. PET/CT imaging was performed using a Siemens Inveon (Knoxville, TN) micro PET/CT scanner. The radioactivity of mouse tissues collected from biodistribution studies was counted using a PerkinElmer (Waltham, MA) Wizard2 2480 automatic gamma counter.

Synthesis of Fmoc-LeuψThz-OH (4) Wherein ψ is a Reduced Peptide Bond

Compound 4 was synthesized following the reaction steps depicted in Scheme 1, shown below:

Scheme 1

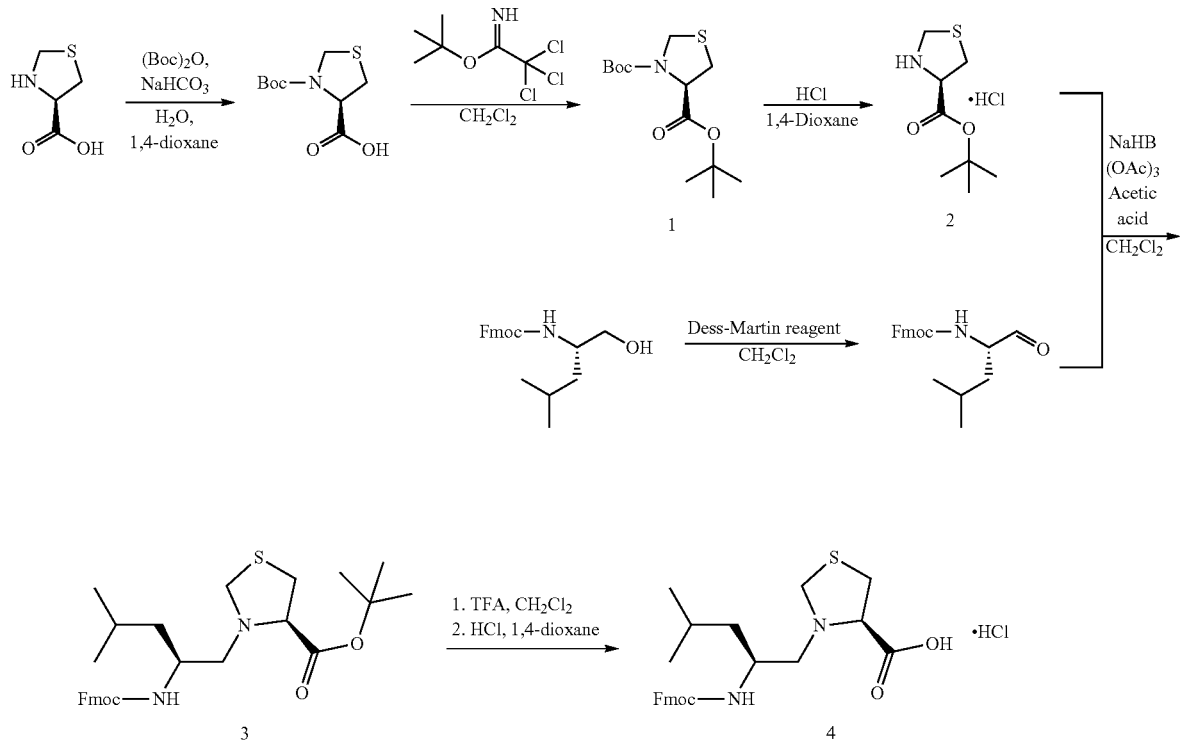

Synthesis of Boc-Thz-OtBu 1: Thiazolidine-4-carboxylic acid (2.66 g, 20 mmol), di-tert-butyl dicarbonate (4.37 g, 20 mmol), and sodium bicarbonate (2.52 g, 30 mmol) were stirring in water (40 mL) and 1,4-dioxane (40 mL) at room temperature overnight. The reaction mixture was washed with ether (100 mL×2) and the aqueous layer was collected. The collected aqueous fraction was adjusted to pH 3 by using concentrated hydrochloric acid before extracted with ethyl acetate (100 mL×2), dried over magnesium sulfate, filtered, and evaporated to obtain white solid. The obtained white solid was dissolved in 30 mL dichloromethane with tert-butyl 2,2,2-trichloroacetimidate (8.74 g, 40 mmol) and the mixture was stirred for 48 hours at room temperature. The mixture was filtered and the filtrate was concentrated in vacuo and purified by flash column chromatography eluted with 1:5 ethyl acetate/hexane to obtain compound 1 (4.36 g, 75% yield) as a colorless oil.

Synthesis of Thz-OtBu HCl salt (2): Compound 1 (4.31 g) was dissolved in a mixture of ethyl acetate (56.3 mL) and 4M HCl in 1,4-dioxane (18.8 mL), and stirred for 4 hours at room temperature. The precipitate was collected by filtration to obtain 2 as a white solid (1.78 g, 53% yield).

Synthesis of Fmoc-LeuψThz-OtBu (3) wherein ψ is a reduced peptide bond: Solution 1: Fmoc-Leucinol (3.79 g, 11.1 mmol) was converted to aldehyde by treating with Dess-Martin periodinane (5.87 g, 13.8 mol) in dichloromethane (70 mL) under ice/water bath for 4 hours. The reaction mixture was then mixed with saturated NaHCO$_3$ aqueous solution (130 mL) and sodium thiosulfate (13.0 g) and stirred for 30 min before being extracted with dichloromethane (130 mL). The organic layer was collected, dried over anhydrous magnesium sulfate, concentrated in vacuo to ~20 mL in volume.

Solution 2: Compound 2 was dissolved in saturated NaHCO$_3$ aqueous solution (35 mL) and the mixture was extracted with ethyl acetate (100 mL×2). The organic phases were combined, dried over anhydrous magnesium sulfate, evaporated in vacuo to obtain colorless oil. The oil was mixed with acetic acid (400 µL, 7.0 mmol) in dichloromethane (30 mL).

Solutions 1 and 2 were mixed and the mixture was stirred for 30 min at room temperature. Sodium triacetoxyborohydride (5.41 g, 25.5 mmol) was added into the mixture and stirred for 20 hours. Saturated NaHCO$_3$ aqueous solution (100 mL) was added and stirred for 10 min. The mixture was extracted with ethyl acetate (100 mL×2). The organic phases were combined, dried over anhydrous MgSO$_4$ and purified by flash column chromatography eluted with 1:3 ether/hexane to obtain 3 as a white solid (2.13 g, 63% yield).

Synthesis of Fmoc-LeuψThz-OH (4) wherein ψ is a reduced peptide bond: Compound 3 was dissolved in a mixture of dichloromethane (25 mL) and trifluoroacetic acid (75 mL) and stirred for 3 hours at room temperature. After concentrated in vacuo, the residue was dissolved in ethyl acetate (80 mL) and mixed with 4M HCl in 1,4-dioxane dioxane (3 mL). After being stirred for 10 min, the volatile solvents were removed in vacuo. Diethyl ether (250 mL) was added to the residue and the mixture was stirred for 30 min. The formed white solid was collected by filtration to obtain 1.38 g of 4 (70% yield). ESI-MS: calculated [M+H]$^+$ for 4 $C_{25}H_{30}N_2O_4S$ 455.59; found 455.42.

Synthesis of LW01025 and LW01029

The chemical structures of LW01025 and LW01029 are shown below:

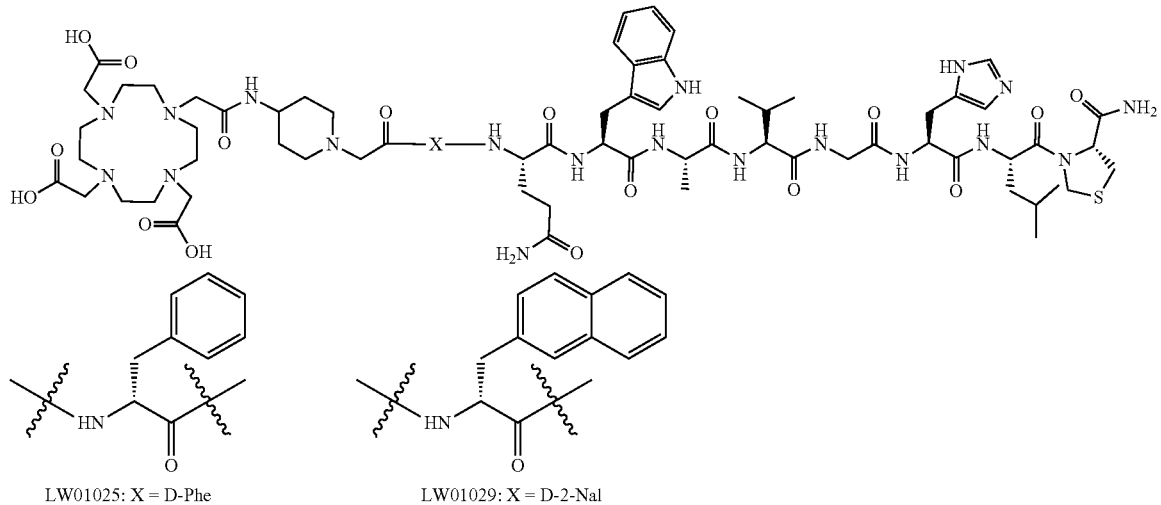

LW01025: X = D-Phe    LW01029: X = D-2-Nal

LW01025 (DOTA-Pip-D-Phe-Gln-Trp-Ala-Val-Gly-His-Leu-Thz-NH$_2$) and LW01029 (DOTA-Pip-D-2-Nal-Gln-Trp-Ala-Val-Gly-His-Leu-Thz-NH$_2$) were synthesized using standard Fmoc solid phase synthesis strategy starting from Fmoc-Rink Amide MBHA resin. Fmoc-Thz-OH (Fmoc-L-thiazolidine-4-carboxylic acid), Fmoc-Leu-OH, Fmoc-His(Trt)-OH, Fmoc-Gly-OH, Fmoc-Val-OH, Fmoc-Ala-OH, Fmoc-Trp(Boc)-OH, Fmoc-Gln(Trt)-OH, Fmoc-D-Phe-OH for LW01025/Fmoc-D-2-Nal-OH for LW01029, Fmoc-4-amino-(1-carboxymethyl) piperidine, and DOTA ($^t$Bu)$_3$ were sequentially coupled to the Fmoc-Rink amide-MBHA resin. After being cleaved with TFA/TIS/water/DODT/thioanisole/phenol 81.5:1:5:2.5:5:5 and precipitated with diethyl ether, the LW01025 crude product was purified by HPLC (C18 semi-prep column; flow rate: 4.5 mL/min; 23% ACN and 0.1%TFA in water; retention time=11.3 min) to obtain a white powder (30% yield). ESI-MS: calculated [M+2H]$^{2+}$ for LW01025 C$_{74}$H$_{108}$N$_{20}$O$_{18}$S 799.4; found 799.6. For LW01029, the crude was purified by HPLC (C18 semi-prep column; flow rate: 4.5 mL/min; 25% ACN and 0.1%TFA in water; retention time=13.0 min) and lyophilized to obtain a white powder (38% yield). ESI-MS: calculated [M+2H]$^{2+}$ for LW01029 C$_{78}$H$_{110}$N$_{20}$O$_{18}$S 824.41; found 824.92.

Synthesis of LW01107, LW01108, LW01110, and LW01142

The chemical structures of LW01107, LW01108, LW01110, and LW01142 are shown below:

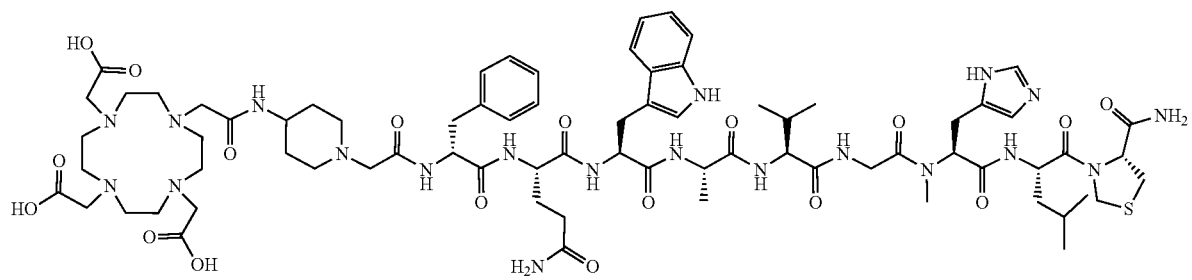

LW01107

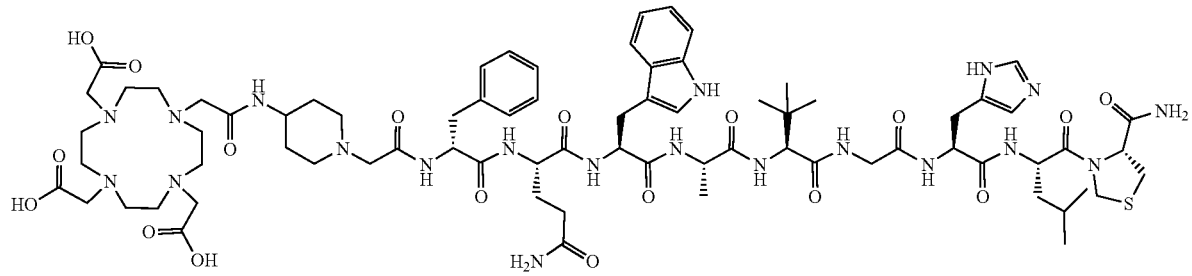

LW01108

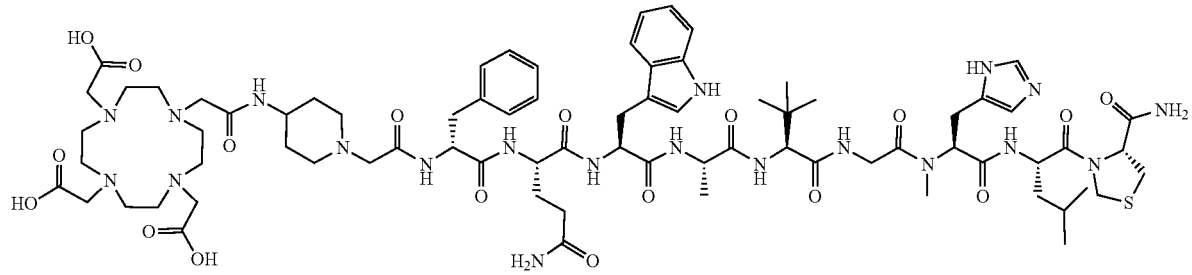

LW01110

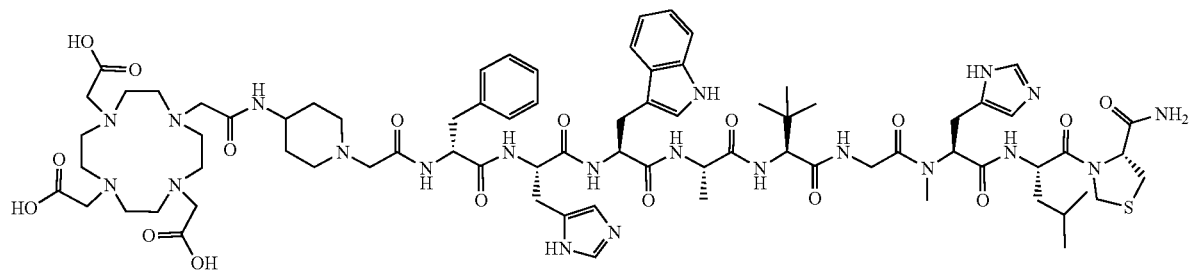

LW01142

LW01107 (DOTA-Pip-D-Phe-Gln-Trp-Ala-Val-Gly-NMe-His-Leu-Thz-NH$_2$), LW01108 (DOTA-Pip-D-Phe-Gln-Trp-Ala-Tle-Gly-His-Leu-Thz-NH$_2$), LW01110 (DOTA-Pip-D-Phe-Gln-Trp-Ala-Tle-Gly-NMe-His-Leu-Thz-NH$_2$), and LW01142 (DOTA-Pip-D-Phe-His-Trp-Ala-Tle-Gly-NMe-His-Leu-Thz-NH$_2$) were synthesized using standard Fmoc solid phase synthesis. Fmoc-protected amino acids, Fmoc-4-amino-(1-carboxymethyl) piperidine and DOTA($^t$Bu)$_3$ were sequentially coupled to the Fmoc-Rink amide-MBHA resin. After being cleaved with TFA/TIS/water/DODT/thioanisole/phenol 81.5:1:5:2.5:5:5 and precipitated by diethyl ether, the crude products were purified with HPLC (C18 semi-prep column; flow rate: 4.5 mL/min) and lyophilized to give white powders.

For LW01107, the HPLC condition was 23% ACN and 0.1%TFA in water (retention time=14.2 min); yield: 19%. ESI-MS: calculated [M+2H]$^{2+}$ for LW01107 C$_{75}$H$_{110}$N$_{20}$O$_{18}$S 806.41; found 806.80. For LW01108, the HPLC condition was 24% ACN and 0.1% TFA in water (retention time=10.9 min); yield: 26%. ESI-MS: calculated [M+2H]$^{2+}$ for LW01108 C$_{75}$H$_{110}$N$_{20}$O$_{18}$S 806.41; found 807.00. For LW01110, the HPLC condition was 24% ACN and 0.1% TFA in water (retention time=14.9 min); yield: 11%. ESI-MS: calculated [M+2H]$^{2+}$ for LW01110 C$_{76}$H$_{112}$N$_{20}$O$_{18}$S 813.41; found 813.66. For LW01142, the HPLC condition was 25% ACN and 0.1% TFA in water (retention time=12.4 min); yield: 17%. ESI-MS: calculated [M+2H]$^{2+}$ for LW01142 C$_{77}$H$_{111}$N$_{21}$O$_{17}$S 817.92; found 817.88.

Synthesis of LW01102 and LW01158

The chemical structures of LW01102 and LW01158 are shown below:

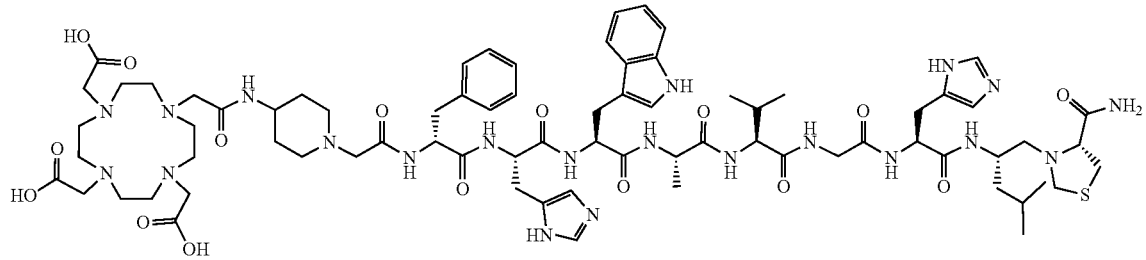

LW01102

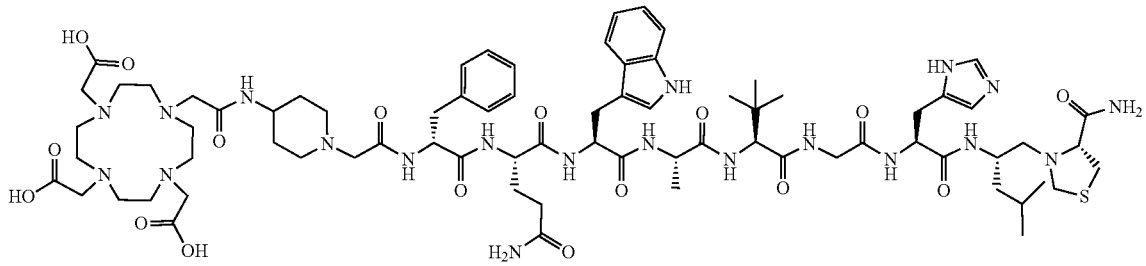

LW01158

LW01102 (DOTA-Pip-D-Phe-His-Trp-Ala-Val-Gly-His-LeuψThz-NH$_2$) and LW01158 (DOTA-Pip-D-Phe-Gln-Trp-Ala-Tle-Gly-His-LeuψThz-NH$_2$), wherein ψ is a reduced peptide bond, was synthesized using standard Fmoc solid phase synthesis strategy starting from Sieber resin. Fmoc-LeuψThz-OH (4), Fmoc-protected amino acids, Fmoc-4-amino-(1-carboxymethyl)-piperidine and DOTA($^t$Bu)$_3$ were sequentially coupled to the resin. After being cleaved with TFA/TIS/water/DODT/thioanisole/phenol 81.5:1:5:2.5:5:5) and precipitated with diethyl ether, the crude product was purified by HPLC (C18 semi-prep column; flow rate: 4.5 mL/min) and lyophilized to give a white powder.

For LW01102, the HPLC condition was 23.5% ACN and 0.1%TFA in water; (retention time=14.9 min) yield: 35%.

ESI-MS: calculated [M+2H]$^{2+}$ for LW01102 C$_{75}$H$_{109}$N$_{21}$O$_{16}$S 796.91; found 796.51. For LW01158, the HPLC condition was 26% ACN and 0.1%TFA in water (retention time=14.1 min); yield: 32%. ESI-MS: calculated [M+2H]$^{2+}$ for LW01158 C$_{75}$H$_{112}$N$_{20}$O$_{17}$S 779.42; found 779.46.

EXAMPLE 2

Synthesis of LW01186, LW02002, LW02021, LW02023 and LW02025

The chemical structures of LW01186, LW02002, LW02021, LW02023, and LW02025 are as follows:

LW01186

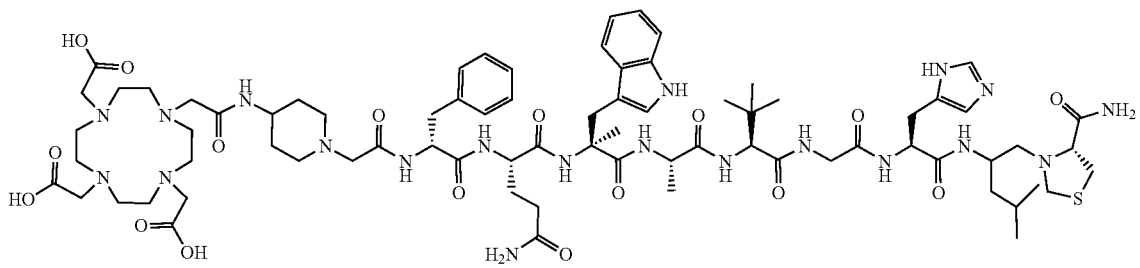

LW02002

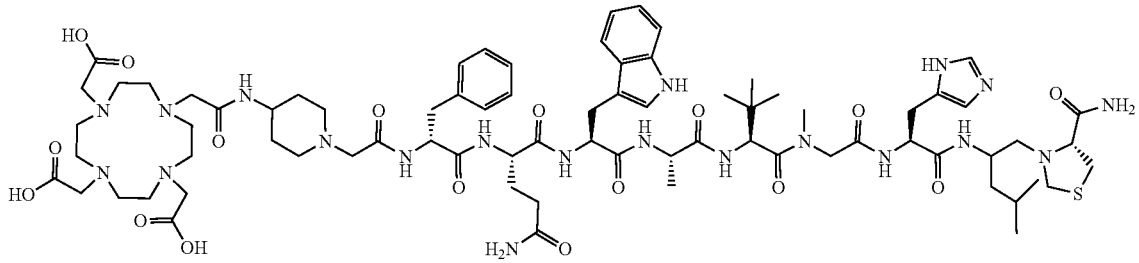

LW02021

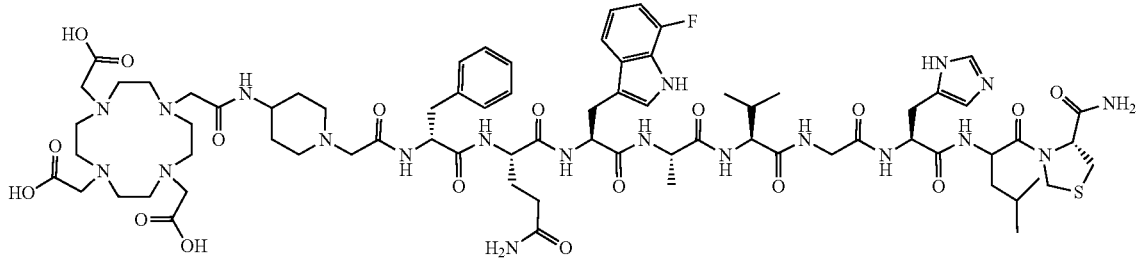

-continued

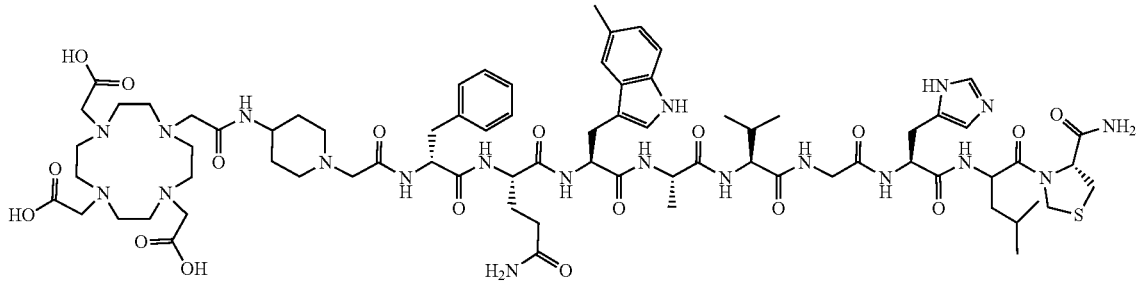
LW02023

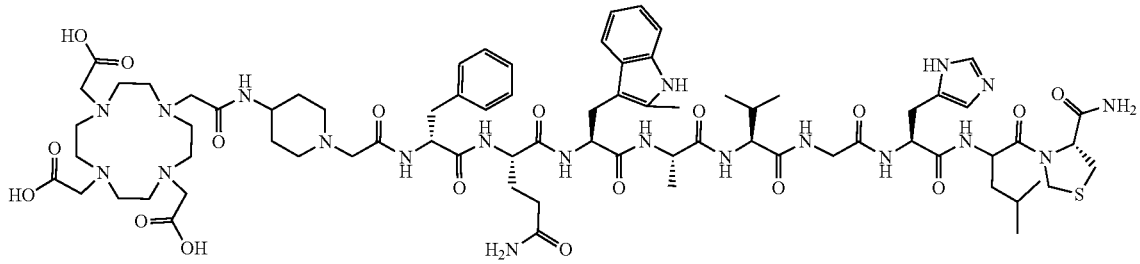
LW02025

LW01186 (DOTA-Pip-D-Phe-Gln-αMe-Trp-Ala-Tle-Gly-His-LeuψThz-NH₂) and LW02002 (DOTA-Pip-D-Phe-Gln-Trp-Ala-Tle-N-Me-Gly-His-LeuψThz-NH₂), wherein ψ is a reduced peptide bond, were synthesized using the Fmoc solid phase synthesis strategy starting from Sieber resin. As described above in Example 1, the compound Fmoc-LeuψThz-OH (4), Fmoc-protected amino acids, Fmoc-4-amino-(1-carboxymethyl)-piperidine and DOTA ($^{t}$Bu)$_3$ were sequentially coupled to the resin. After being cleaved with TFA/TIS/water/DODT/thioanisole/phenol 81.5:1:5:2.5:5:5) and precipitated with diethyl ether, the crude product was purified by HPLC (C18 semi-prep column; flow rate: 4.5 mL/min) and lyophilized to give a white powder.

LW02021 (DOTA-Pip-D-Phe-Gln-7-F-Trp-Ala-Val-Gly-His-Leu-Thz-NH₂), LW02023 (DOTA- Pip-D-Phe-Gln-5-Me-Trp-Ala-Val-Gly-His-Leu-Thz-NH₂) and LW02025 (DOTA-Pip-D-Phe-Gln-2-Me-Trp-Ala-Val-Gly-His-Leu-Thz-NH₂) were synthesized using the Fmoc solid phase synthesis strategy starting from Fmoc-Rink MBHA resin. Fmoc-protected amino acids, Fmoc-4-amino-(1-carboxymethyl)-piperidine and DOTA($^{t}$Bu)$_3$ were sequentially coupled to the resin. After being cleaved with TFA/TIS/water/DODT/thioanisole/phenol 81.5:1:5:2.5:5:5) and precipitated with diethyl ether, the crude product was purified by HPLC (C18 semi-prep column; flow rate: 4.5 mL/min) and lyophilized to give a white powder. The HPLC conditions and results are shown below in Table 5.

TABLE 5

| HPLC CONDITIONS AND RESULTS | | | | | |
|---|---|---|---|---|---|
| Compound name | HPLC conditions | Retention time (min) | Yield (%) | Calculated mass (m/z) | Found (m/z) |
| LW01186 | 29% CH₃CN and 0.1% TFA in H₂O | 12.1 | 7.7 | [M + 2H]²⁺ 806.5 | [M + 2H]²⁺ 806.8 |
| LW02002 | 27% CH₃CN and 0.1% TFA in H₂O | 15.3 | 17 | [M + 2H]²⁺ 806.5 | [M + 2H]²⁺ 806.7 |
| LW02021 | 25% CH₃CN and 0.1% TFA in H₂O | 8.9 | 33 | [M + 2H]²⁺ 808.4 | [M + 2H]²⁺ 808.4 |
| LW02023 | 25% CH₃CN and 0.1% TFA in H₂O | 12.2 | 19 | [M + 2H]²⁺ 806.4 | [M + 2H]²⁺ 806.5 |
| LW02025 | 23% CH₃CN and 0.1% TFA in H₂O | 13.7 | 16 | [M + 2H]²⁺ 806.4 | [M + 2H]²⁺ 806.6 |

Synthesis of LW01080, LW01085, LW01088, and LW01136
The chemical structures of LW01080, LW01085, LW01088 and LW01136 are shown below:
LW01080 (D-Phe-Gln-Trp-Ala-Tle-Gly-His-Leu-Thz-NH₂), LW01085 (D-Phe-Gln-Trp-Ala-Val-Gly-His-Leu-Thz-NH₂), LW01088 (D-Phe-Gln-Trp-Ala-Val-Gly-NMe-His-Leu-Thz-NH₂), and LW01136 (D-Phe-Gln-Trp(Me)-Ala-Val-Gly-His-Leu-Thz-NH₂) were synthesized using
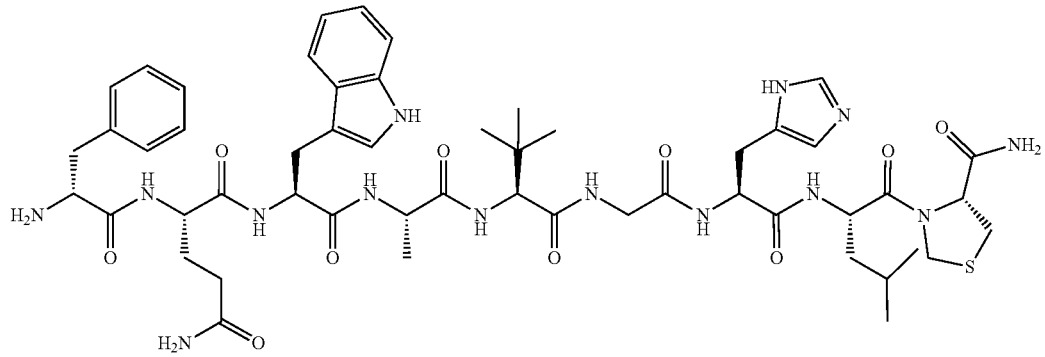
LW01080
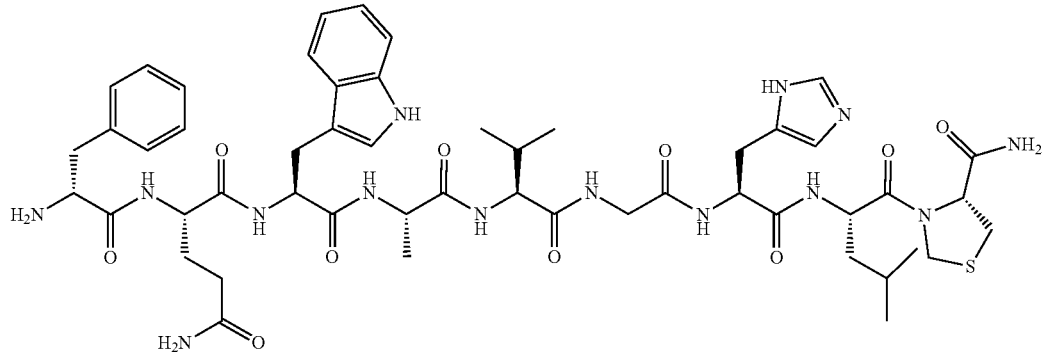
LW01085
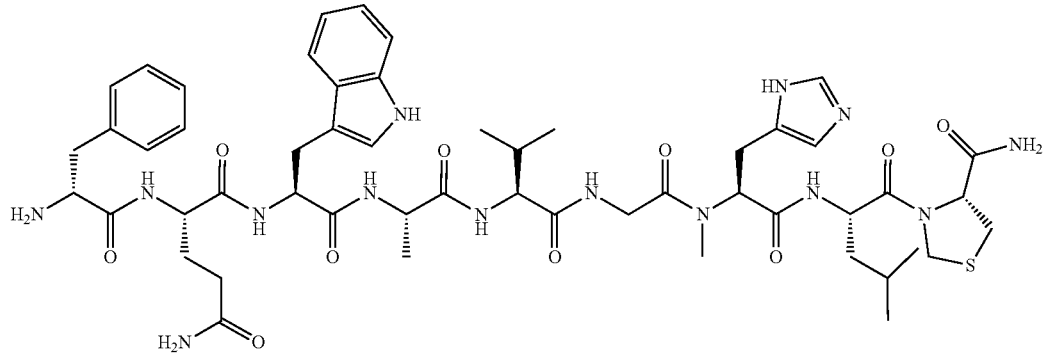
LW01088
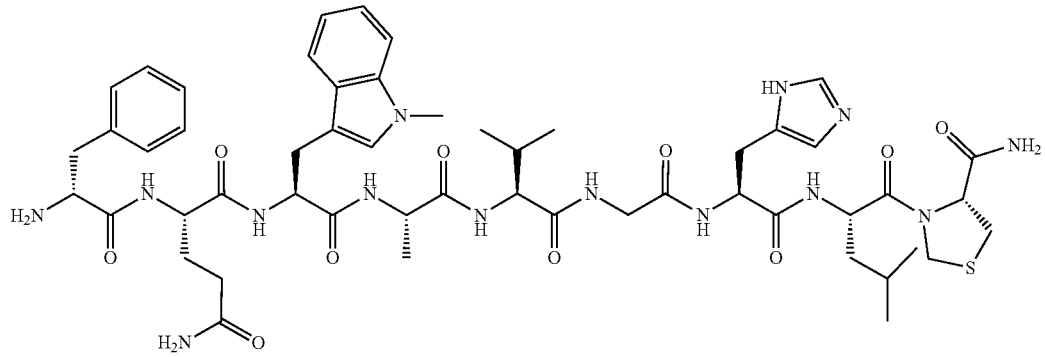
LW01136 standard Fmoc solid phase synthesis. Fmoc-protected amino acids were sequentially coupled to the Fmoc-Rink amide-MBHA resin. After being cleaved with TFA/TIS/water/DODT/thioanisole/phenol 81.5:1:5:2.5:5:5 and precipitated with diethyl ether, the crude products were purified with HPLC (C18 semi-prep column; flow rate: 4.5 mL/min) and lyophilized to give white powders.

For LW01080, the HPLC condition was 26% ACN and 0.1%TFA in water (retention time=9.02 min); yield: 26%. ESI-MS: calculated [M+H]$^+$ for LW01080 $C_{52}H_{72}N_{14}O_{10}S$ 1085.54; found 1085.99. For LW01085, the HPLC condition was 23% ACN and 0.1%TFA in water (retention time=16.0 min); yield: 41%. ESI-MS: calculated [M+H]$^+$ for LW01085 $C_{51}H_{70}N_{14}O_{10}S$ 1071.52; found 1071.77. For LW01088, the HPLC condition was 23% ACN and 0.1%TFA in water (retention time=17.4 min); yield: 29%. ESI-MS: calculated [M+H]$^+$ for LW01088 $C52H_{72}N_{14}O_{10}S$ 1085.54; found 1085.69. For LW01136, the HPLC condition was 27% ACN and 0.1%TFA in water (retention time=13.4 min); yield: 30%. ESI-MS: calculated [M+H]$^+$ for LW01136 $C_{52}H_{72}N_{14}O_{10}S$ 1085.54; found 1085.79.

EXAMPLE 3

Synthesis of LW02011, LW02016, LW02019, LW01166, LW01171, LW01173, LW01175, LW01177, LW01180, LW01182, LW01183, LW01191, LW02007, LW02009, LW02013, and LW02015

The chemical structures of LW02011, LW02016, LW02019, LW01166, LW01171, LW01173, LW01175, LW01177, LW01180, LW01182, LW01183, LW01191, LW02007, LW02009, LW02013, and LW02015 are as follows:

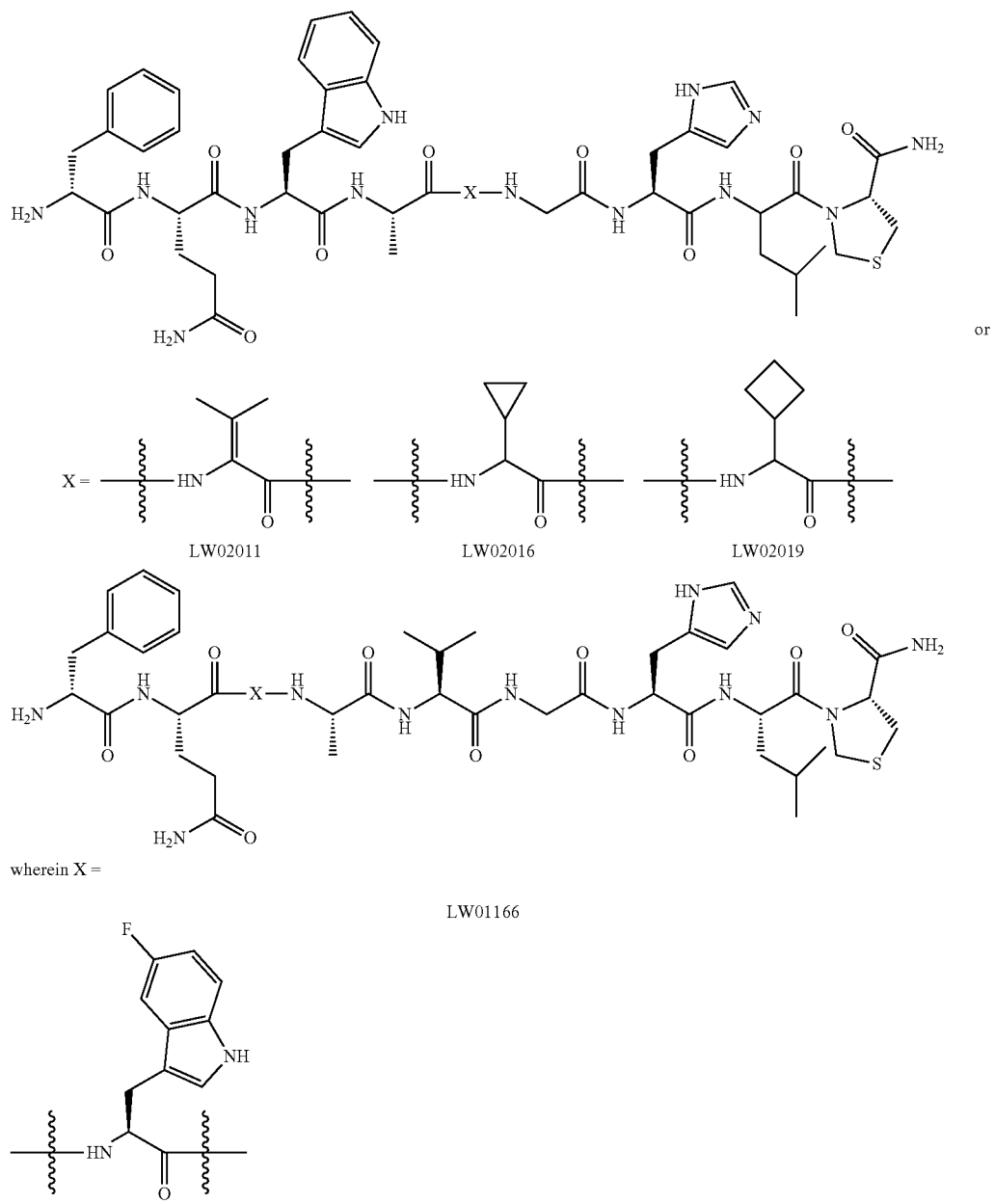

-continued
LW01171
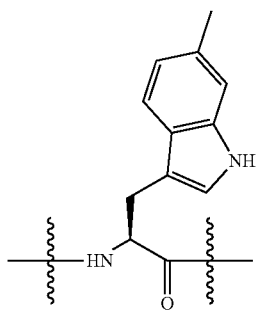
LW01173
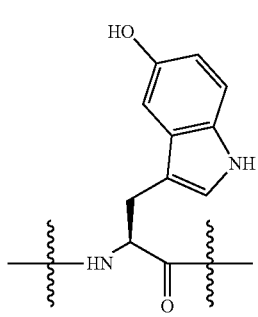
LW01175
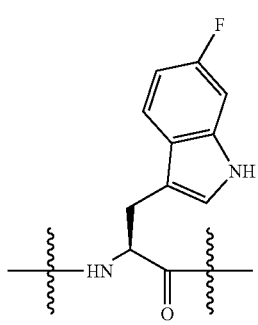
LW01177
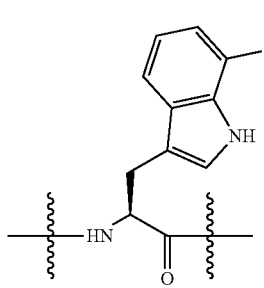
LW01180
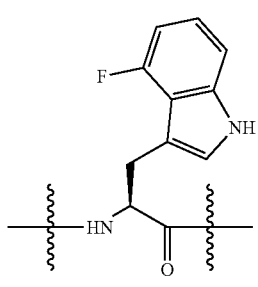

-continued
LW01182
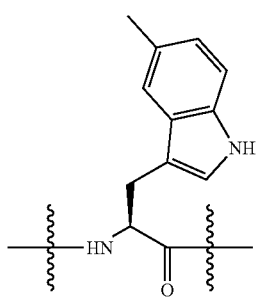
LW01183
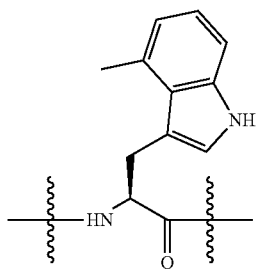
LW01191
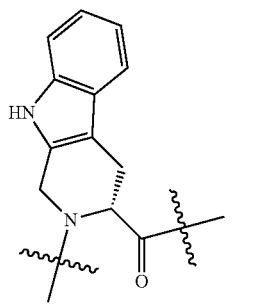
LW02007
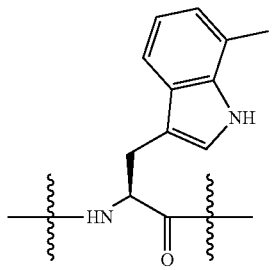
LW02009
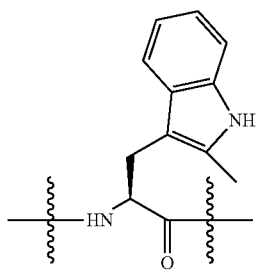

LW02013

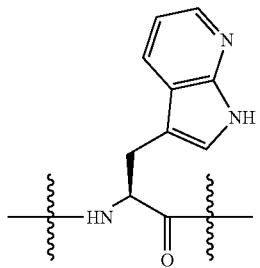

LW02015

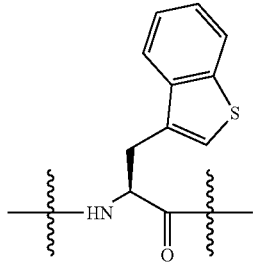

LW02011(D-Phe-Gln-Trp-Ala-2,3-dehydro-Val-Gly-His-Leu-Thz-NH$_2$),
LW02016(D-Phe-Gln-Trp-Ala-L-cyclopropylglycine-Gly-His-Leu-Thz-NH$_2$),
LW02019(D-Phe-Gln-Trp-Ala-cyclobutylglycine-Gly-His-Leu-Thz-NH$_2$),
LW01166(D-Phe-Gln-5-F-Trp-Ala-Val-Gly-His-Leu-Thz-NH$_2$),
LW01171(D-Phe-Gln-6-Me-Trp-Ala-Val-Gly-His-Leu-Thz-NH$_2$),
LW01173(D-Phe-Gln-5-0H-Trp-Ala-Val-Gly-His-Leu-Thz-NH$_2$),
LW01175(D-Phe-Gln-6-F-Trp-Ala-Val-Gly-His-Leu-Thz-NH$_2$),
LW01177(D-Phe-Gln-7-F-Trp-Ala-Val-Gly-His-Leu-Thz-NH$_2$),
LW01180(D-Phe-Gln-4-F-Trp-Ala-Val-Gly-His-Leu-Thz-NH$_2$),
LW01182(D-Phe-Gln-5-Me-Trp-Ala-Val-Gly-His-Leu-Thz-NH$_2$),
LW01183(D-Phe-Gln-4-Me-Trp-Ala-Val-Gly-His-Leu-Thz-NH$_2$),
LW01191(D-Phe-Gln-D-Tpi-Ala-Val-Gly-His-Leu-Thz-NH$_2$),
LW02007(D-Phe-Gln-7-Me-Trp-Ala-Val-Gly-His-Leu-Thz-NH$_2$),
LW02009(D-Phe-Gln-2-Me-Trp-Ala-Val-Gly-His-Leu-Thz-NH$_2$),
LW02013(D-Phe-Gln-7-Aza-Trp-Ala-Val-Gly-His-Leu-Thz-NH$_2$), and
LW02015(D-Phe-Gln-Bta-Ala-Val-Gly-His-Leu-Thz-NH$_2$) were synthesized using standard Fmoc solid phase synthesis. Fmoc-protected amino acids were sequentially coupled to the Fmoc-Rink amide-MBHA resin. After being cleaved with TFA/TIS/water/DODT/thioanisole/phenol 81.5:1:5:2.5:5:5 and precipitated with diethyl ether, the crude products were purified with HPLC (C18 semi-prep column; flow rate: 4.5 mL/min) and lyophilized to give white powders. The HPLC conditions are shown below in Table 6.

TABLE 6

| Compound name | HPLC conditions | Retention time (min) | Yield (%) | Calculated mass (m/z) | Found (m/z) |
|---|---|---|---|---|---|
| LW02011 | 25% CH$_3$CN and 0.1% TFA in H$_2$O | 9.0 | 5.0 | [M + H]$^+$ 1069.5 | [M + H]$^+$ 1069.7 |
| LW02016 | 25% CH$_3$CN and 0.1% TFA in H$_2$O | 8.4 | 11 | [M + H]$^+$ 1069.5 | [M + H]$^+$ 1069.4 |
| LW02019 | 26% CH$_3$CN and 0.1% TFA in H$_2$O | 9.8 | 15 | [M + H]$^+$ 1083.5 | [M + H]$^+$ 1083.5 |
| LW01166 | 25% CH$_3$CN and 0.1% TFA in H$_2$O | 10.5 | 46 | [M + H]$^+$ 1089.5 | [M + H]$^+$ 1089.5 |
| LW01171 | 26% CH$_3$CN and 0.1% TFA in H$_2$O | 11.5 | 29 | [M + H]$^+$ 1085.5 | [M + H]$^+$ 1085.7 |
| LW01173 | 22% CH$_3$CN and 0.1% TFA in H$_2$O | 8.6 | 21 | [M + H]$^+$ 1087.5 | [M + H]$^+$ 1087.6 |
| LW01175 | 25% CH$_3$CN and 0.1% TFA in H$_2$O | 13.0 | 40 | [M + H]$^+$ 1089.5 | [M + H]$^+$ 1089.6 |
| LW01177 | 25% CH$_3$CN and 0.1% TFA in H$_2$O | 12.2 | 24 | [M + H]$^+$ 1089.5 | [M + H]$^+$ 1089.7 |
| LW01180 | 25% CH$_3$CN and 0.1% TFA in H$_2$O | 11.4 | 36 | [M + H]$^+$ 1089.5 | [M + H]$^+$ 1089.5 |

TABLE 6-continued

HPLC CONDITIONS AND RESULTS

| Compound name | HPLC conditions | Retention time (min) | Yield (%) | Calculated mass (m/z) | Found (m/z) |
|---|---|---|---|---|---|
| LW01182 | 26% CH$_3$CN and 0.1% TFA in H$_2$O | 11.7 | 33 | [M + H]$^+$ 1085.5 | [M + H]$^+$ 1085.6 |
| LW01183 | 26% CH$_3$CN and 0.1% TFA in H$_2$O | 10.3 | 26 | [M + H]$^+$ 1085.5 | [M + H]$^+$ 1085.7 |
| LW01191 | 27% CH$_3$CN and 0.1% TFA in H$_2$O | 11.3 | 20 | [M + H]$^+$ 1083.5 | [M + H]$^+$ 1083.5 |
| LW02007 | 27% CH$_3$CN and 0.1% TFA in H$_2$O | 9.0 | 25 | [M + H]$^+$ 1085.5 | [M + H]$^+$ 1085.5 |
| LW02009 | 26% CH$_3$CN and 0.1% TFA in H$_2$O | 9.1 | 23 | [M + H]$^+$ 1085.5 | [M + H]$^+$ 1085.5 |
| LW02013 | 18% CH$_3$CN and 0.1% TFA in H$_2$O | 13.5 | 8.4 | [M + H]$^+$ 1072.5 | [M + H]$^+$ 1072.5 |
| LW02015 | 26% CH$_3$CN and 0.1% TFA in H$_2$O | 14.4 | 24 | [M + H]$^+$ 1088.5 | [M + H]$^+$ 1088.4 |

EXAMPLE 4

Syntheses of nonradioactive Ga-complexed standards of LW01025, LW01029, LW01107, LW01108, LW01110, LW01102, LW01142, LW01158, LW01186, LW02002, LW02021, LW02023, and LW02025

LW01025 (2.82 mg), LW01029 (2.12 mg), LW01107 (2.20 mg), LW01108 (2.42 mg), LW01110 (2.03 mg), LW01102 (2.17 mg), LW01142 (1.81 mg), LW01158 (2.54 mg) were dissolved respectively in 0.5 mL NaOAc buffer (0.1 N, pH 4.53) and GaCl$_3$ (5 eq., 0.2 M) was added. Approximately 2 mg of LW01186, LW02002, LW02021, LW02023, and LW02025 were dissolved each in 0.5 mL NaOAc buffer (0.1 N, pH 4.53) and GaCl$_3$ (5 eq., 0.2 M) was added. The respective reaction mixtures were incubated at 80° C. for 15 min and then purified with HPLC (C18 semi-prep column) and lyophilized to give white powders. The HPLC conditions are shown below in Table 7.

TABLE 7

HPLC CONDITIONS AND RESULTS

| Compound name | HPLC conditions | Retention time (min) | Yield (%) | Calculated mass (m/z) | Found (m/z) |
|---|---|---|---|---|---|
| Ga-LW01025 | 23% CH$_3$CN and 0.1% TFA in H$_2$O | 12.0 | 82 | [M + 2H]$^{2+}$ 833.9 | [M + 2H]$^{2+}$ 833.7 |
| Ga-LW01029 | 25% CH$_3$CN and 0.1% TFA in H$_2$O | 13.9 | 63 | [M + 2H]$^{2+}$ 858.9 | [M + 2H]$^{2+}$ 858.5 |
| Ga-LW01107 | 23% CH$_3$CN and 0.1% TFA in H$_2$O | 14.2 | 73 | [M + 2H]$^{2+}$ 840.9 | [M + 2H]$^{2+}$ 840.4 |
| Ga-LW01108 | 24% CH$_3$CN and 0.1% TFA in H$_2$O | 13.2 | 59 | [M + 2H]$^{2+}$ 840.9 | [M + 2H]$^{2+}$ 840.9 |
| Ga-LW01110 | 24% CH$_3$CN and 0.1% TFA in H$_2$O | 15.8 | 54 | [M + 2H]$^{2+}$ 847.9 | [M + 2H]$^{2+}$ 847.8 |
| Ga-LW01102 | 23.5% CH$_3$CN and 0.1% TFA in H$_2$O | 15.7 | 43 | [M + 2H]$^{2+}$ 831.4 | [M + 2H]$^{2+}$ 831.4 |
| Ga-LW01142 | 25% CH$_3$CN and 0.1% TFA in H$_2$O | 11.1 | 53 | [M + 2H]$^{2+}$ 851.4 | [M + 2H]$^{2+}$ 851.9 |
| Ga-LW01158 | 26% CH$_3$CN and 0.1% TFA in H$_2$O | 13.2 | 76 | [M + 2H]$^{2+}$ 832.9 | [M + 2H]$^{2+}$ 832.9 |
| Ga-LW01186 | 29% CH$_3$CN and 0.1% TFA in H$_2$O | 13.5 | 81 | [M + 2H]$^{2+}$ 839.4 | [M + 2H]$^{2+}$ 839.5 |
| Ga-LW02002 | 27% CH$_3$CN and 0.1% TFA in H$_2$O | 16.3 | 77 | [M + 2H]$^{2+}$ 839.4 | [M + 2H]$^{2+}$ 839.4 |
| Ga-LW02021 | 25% CH$_3$CN and 0.1% TFA in H$_2$O | 14.4 | 82 | [M + 2H]$^{2+}$ 841.4 | [M + 2H]$^{2+}$ 841.5 |
| Ga-LW02023 | 25% CH$_3$CN and 0.1% TFA in H$_2$O | 13.1 | 84 | [M + 2H]$^{2+}$ 839.4 | [M + 2H]$^{2+}$ 839.8 |
| Ga-LW02025 | 23% CH$_3$CN and 0.1% TFA in H$_2$O | 16.8 | 81 | [M + 2H]$^{2+}$ 839.4 | [M + 2H]$^{2+}$ 832.9 |

EXAMPLE 5

Syntheses of Nonradioactive Lu-Complexed Standards of LW01090, LW01110, and LW01142

Approximately 2 mg of LW01090, LW01110, or LW01142 were dissolved respectively in 0.5 mL NaOAc buffer (0.1 N, pH 4.48) and LuCl$_3$ (10 eq., 0.1 M) was added. The reaction mixture was incubated at 80° C. for 30 min and then purified with HPLC (C18 semi-prep column) and lyophilized to give white powders. The HPLC conditions are shown below in Table 8.

TABLE 8

HPLC CONDITIONS AND RESULTS

| Compound name | HPLC conditions | Retention time (min) | Yield (%) | Calculated mass (m/z) | Found (m/z) |
|---|---|---|---|---|---|
| Lu-LW01090 | 26% CH$_3$CN and 0.1% TFA in H$_2$O | 13.9 | 47 | [M + 2H]$^{2+}$ 885.4 | [M + 2H]$^{2+}$ 885.6 |
| Lu-LW01110 | 24% CH$_3$CN and 0.1% TFA in H$_2$O | 18.0 | 88 | [M + 2H]$^{2+}$ 899.4 | [M + 2H]$^{2+}$ 899.7 |
| Lu-LW01142 | 24% CH$_3$CN and 0.1% TFA in H$_2$O | 15.9 | 61 | [M + 2H]$^{2+}$ 903.9 | [M + 2H]$^{2+}$ 904.0 |

EXAMPLE 6

Synthesis of $^{68}$Ga-Labeled Peptides

Purified $^{68}$Ga in 0.5 mL water was added into a 4-mL glass vial preloaded with 0.7 mL of HEPES buffer (2 M, pH 5.0) and 10 μL precursor solution (1 mM). The radiolabeling reaction was carried out under microwave heating for 1 min before being purified by HPLC using the semi-preparative column. The eluate fraction containing the radiolabeled product was collected, diluted with water (50 mL), and passed through a C18 Sep-Pak cartridge that was pre-washed with ethanol (10 mL) and water (10 mL). After washing the C18 Sep-Pak cartridge with water (10 mL), the $^{68}$Ga-labeled product was eluted off the cartridge with ethanol (0.4 mL), and diluted with saline for imaging and biodistribution. Quality control was performed using the analytical column. The tracers were obtained with more than 95% radiochemical purity.

In Vitro Competition Binding Assay

PC-3 cells were seeded at 2×10 5 cells/well in 24-well poly-D-lysine plates 24-48 hours prior to the experiment. The growth medium was replaced by 400 μL of reaction medium (RPMI 1640 containing 2 mg/mL BSA, 4.8 mg/mL HEPES, 1 U/mL penicillin G and 1 μg/mL streptomycin). Cells were incubated for 30-60 min at 37° C. Peptides as provided in Table 9 below provided in 50 μL of decreasing concentrations (10 μM to 1 μM) and 50 μL of 0.011 nM [$^{125}$I-Tyr$^4$]bombesin were added to wells. The cells were incubated with moderate agitation for 1 h at 27° C., washed twice with ice-cold PBS, harvested by trypsinization, and measured for radioactivity on the gamma counter. Data were analyzed using nonlinear regression (one binding site model for competition assay) with GraphPad Prism 8.

TABLE 9

Binding affinities (Ki, nM) of GRPR-targeting peptides
Binding affinities Ki (n = 2-3)

| Compound | Mean | SD |
|---|---|---|
| LW01080 | 3.56 | 0.72 |
| LW01085 | 8.77 | 1.33 |
| LW01088 | 9.00 | 1.99 |
| LW01136 | 35.7 | 13.8 |
| LW02016 | 202 | 103 |
| LW02019 | 35.7 | 27.4 |
| LW01166 | 17.9 | 0.57 |
| LW01175 | 46.9 | 9.73 |
| LW01177 | 9.38 | 1.68 |
| LW01180 | 43.4 | 10.2 |
| LW01182 | 10.5 | 1.86 |
| LW01183 | 25.9 | 4.51 |
| LW02007 | 13.5 | 1.79 |
| LW02009 | 11.5 | 1.71 |
| LW02013 | 166 | 73.4 |
| LW02015 | 53.1 | 28.2 |
| Ga-LW01025 | 7.62 | 0.19 |
| Ga-LW01029 | 6.07 | 0.59 |
| Ga-LW01107 | 2.98 | 0.60 |
| Ga-LW01108 | 1.34 | 0.12 |
| Ga-LW01110 | 1.39 | 0.03 |
| Ga-LW01102 | 2.84 | 1.01 |
| Ga-LW01142 | 3.45 | 0.90 |
| Ga-LW01158 | 5.35 | 0.27 |
| Ga-LW01186 | 6.94 | 0.95 |
| Ga-LW02002 | 11.0 | 0.39 |
| Ga-LW02021 | 13.6 | 2.83 |
| Ga-LW02023 | 14.9 | 3.39 |
| Ga-LW02025 | 14.7 | 4.20 |
| Lu-LW01090 | 12.6 | 1.02 |
| Lu-LW01110 | 3.07 | 0.15 |
| Lu-LW01142 | 2.37 | 0.28 |

PET/CT Imaging and Ex Vivo Biodistribution in PC-3 Tumor-Bearing Mice

All imaging and biodistribution studies were performed using male NOD.Cg-Rag1$^{tm1MoM}$ Il2rg$^{tm1WI}$/SzJ (NRG) mice and conducted according to the guidelines established by the Canadian Council on Animal Care and approved by Animal Ethics Committee of the University of British Columbia. For tumor inoculations, mice were anesthetized by inhalation with 2% isoflurane in oxygen and implanted subcutaneously with 5×10$^6$ PC-3 cells below the left shoulder. Imaging and biodistribution studies were performed only after tumors grew to 5-8 mm in diameter.

For PET/CT imaging studies, ~3-4 MBq of the $^{68}$Ga-labeled tracer was injected through the tail vein. Mice were allowed to recover and roam freely in the cages after injecting the tracer. At 45 min post-injection (p.i.), mice were sedated again and positioned on the scanner. First, a 10 min CT scan was conducted for localization and attenuation correction for reconstruction of PET images, before a 10 min PET image was acquired. Heating pads were used during the entire procedure to keep the mice warm. For ex vivo biodistribution studies, mice were injected with ~1.5-3 MBq of the $^{68}$Ga-labeled tracer. At 1 h p.i., mice were euthanized, blood was drawn from heart, and organs/tissues of interest were collected, rinsed with PBS, blotted dry, weighed, and counted using an automated gamma counter. The uptake in each organ/tissue was normalized to the injected dose and expressed as the percentage of the injected dose per gram of tissue (% ID/g).

A representative maximum-intensity-projection PET image of $^{68}$Ga-LW01025, $^{68}$Ga-LW01029, $^{68}$Ga-LW01107, $^{68}$Ga-LW01108, $^{68}$Ga-LW01110, $^{68}$Ga-LW01142, $^{68}$Ga- LW01158, and $^{68}$Ga-LW01102 in mice bearing PC-3 tumor xenografts is shown in FIG. 1. Biodistribution data is shown in Tables 10 and 11.

TABLE 10

Biodistribution data (at 1 h post-injection, % ID/g) of $^{68}$Ga-LW01025, $^{68}$Ga-LW01108, and $^{68}$Ga-LW01110 in mice bearing PC-3 tumor xenografts.

| Tissues | $^{68}$Ga-LW01025 (n = 4) | |
| --- | --- | --- |
| | Mean | SD |
| PC3 tumor | 6.20 | 0.14 |
| Blood | 0.34 | 0.07 |
| Fat | 0.09 | 0.02 |
| Seminal | 0.06 | 0.02 |
| Testes | 0.16 | 0.06 |
| Small Intestine | 0.56 | 0.12 |
| Large Intestine | — | — |
| Spleen | 0.23 | 0.06 |
| Pancreas | 1.28 | 0.16 |
| Stomach | 0.54 | 0.33 |
| Liver | 0.29 | 0.13 |
| Adrenal | 0.54 | 0.13 |
| kidneys | 2.37 | 0.12 |
| Heart | 0.13 | 0.01 |
| Lungs | 0.34 | 0.05 |
| Bone | 0.24 | 0.12 |
| Muscle | 0.13 | 0.10 |
| Brain | 0.03 | 0.01 |

Table 11 shows Biodistribution data of $^{68}$Ga-LW01029, $^{68}$Ga-LW01107, $^{68}$Ga-LW01142, $^{68}$Ga-LW01158, and $^{68}$Ga-LW01102 and further completed distribution data of $^{68}$Ga-LW01108 and $^{68}$Ga-LW01110 in mice bearing PC-3 tumor xenografts.

TABLE 11

Biodistribution data (at 1 h post injection, % ID/g) in mice bearing PC-3 tumor xenografts.

| | n = 4 | | | | | | | |
| --- | --- | --- | --- | --- | --- | --- | --- | --- |
| | $^{68}$Ga-LW01029 | | $^{68}$Ga-LW01107 | | $^{68}$Ga-LW01108 | | $^{68}$Ga-LW01110 | |
| Tissues | Mean | SD | Mean | SD | Mean | SD | Mean | SD |
| PC3 tumor | 4.70 | 1.27 | 7.05 | 0.71 | 5.90 | 0.68 | 16.59 | 1.60 |
| Blood | 1.08 | 0.47 | 0.30 | 0.04 | 0.59 | 0.18 | 0.69 | 0.14 |
| Fat | 0.18 | 0.19 | 0.05 | 0.01 | 0.06 | 0.02 | 0.09 | 0.02 |
| Seminal | 0.13 | 0.07 | 0.04 | 0.01 | 0.11 | 0.03 | 0.10 | 0.06 |
| Testes | 0.33 | 0.13 | 0.10 | 0.02 | 0.16 | 0.03 | 0.16 | 0.07 |
| Small Intestine | 1.05 | 0.30 | 0.31 | 0.01 | 2.29 | 0.54 | 2.11 | 0.48 |
| Large Intestine | 0.96 | 0.42 | 0.18 | 0.04 | 1.31 | 0.33 | 1.27 | 0.27 |
| Spleen | 0.45 | 0.35 | 0.13 | 0.02 | 0.40 | 0.30 | 0.29 | 0.05 |
| Pancreas | 2.56 | 0.55 | 0.39 | 0.03 | 9.32 | 1.97 | 8.99 | 1.54 |
| Stomach | 0.77 | 0.42 | 0.07 | 0.01 | 0.89 | 0.18 | 0.94 | 0.31 |
| Liver | 0.63 | 0.23 | 0.32 | 0.15 | 0.35 | 0.19 | 0.41 | 0.06 |
| Adrenal | 0.82 | 0.45 | 0.32 | 0.19 | 1.51 | 0.99 | 1.64 | 0.18 |
| Kidneys | 4.73 | 2.57 | 1.88 | 0.17 | 2.47 | 0.66 | 3.26 | 0.25 |
| Heart | 0.36 | 0.17 | 0.11 | 0.02 | 0.18 | 0.04 | 0.23 | 0.03 |
| Lungs | 1.82 | 0.59 | 0.28 | 0.04 | 0.49 | 0.22 | 0.59 | 0.12 |
| Bone | 0.19 | 0.06 | 0.06 | 0.02 | 0.15 | 0.11 | 0.12 | 0.00 |
| Muscle | 0.23 | 0.13 | 0.07 | 0.02 | 0.17 | 0.11 | 0.14 | 0.03 |
| Brain | 0.04 | 0.02 | 0.01 | 0.00 | 0.02 | 0.00 | 0.03 | 0.00 |

TABLE 11-continued

Biodistribution data (at 1 h post injection, % ID/g) in mice bearing PC-3 tumor xenografts.

| | n = 4 | | | | | |
| --- | --- | --- | --- | --- | --- | --- |
| | $^{68}$Ga-LW01142 | | $^{68}$Ga-LW01158 | | $^{68}$Ga-LW01102 | |
| Tissues | Mean | SD | Mean | SD | Mean | SD |
| PC3 tumor | 11.43 | 1.22 | 11.15 | 0.65 | 7.46 | 0.44 |
| Blood | 6.88 | 0.29 | 1.14 | 0.15 | 1.13 | 0.25 |
| Fat | 0.32 | 0.08 | 0.07 | 0.01 | 0.09 | 0.03 |
| Seminal | 0.33 | 0.02 | 0.15 | 0.12 | 0.23 | 0.27 |
| Testes | 1.28 | 0.19 | 0.24 | 0.01 | 0.33 | 0.12 |
| Small Intestine | 1.70 | 0.10 | 2.46 | 0.30 | 2.85 | 0.39 |
| Large Intestine | 1.07 | 0.09 | 1.41 | 0.38 | 1.25 | 0.27 |
| Spleen | 0.88 | 0.09 | 0.60 | 0.42 | 0.52 | 0.27 |
| Pancreas | 4.40 | 0.27 | 12.01 | 1.41 | 13.14 | 1.31 |
| Stomach | 0.98 | 0.05 | 1.30 | 0.41 | 1.23 | 0.68 |
| Liver | 2.88 | 0.45 | 4.33 | 0.22 | 3.22 | 0.32 |
| Adrenal | 2.07 | 0.27 | 1.37 | 0.35 | 1.36 | 0.44 |
| Kidneys | 6.36 | 0.41 | 2.98 | 0.34 | 6.30 | 0.47 |
| Heart | 1.62 | 0.12 | 0.34 | 0.05 | 0.36 | 0.05 |
| Lungs | 4.59 | 0.81 | 1.19 | 0.32 | 1.55 | 0.61 |
| Bone | 0.47 | 0.08 | 0.13 | 0.01 | 0.13 | 0.07 |
| Muscle | 0.52 | 0.07 | 0.20 | 0.05 | 0.18 | 0.01 |
| Brain | 0.15 | 0.02 | 0.03 | 0.00 | 0.04 | 0.01 |

In Vivo Stability of $^{68}$Ga-LW01025, $^{68}$Ga-LW01029, $^{68}$Ga-LW01107, $^{68}$Ga-LW01108, $^{68}$Ga-LW01110, $^{68}$Ga-LW01102, and $^{68}$Ga-LW01142

In vivo plasma stability studies were conducted for $^{68}$Ga-labeled tracers to evaluate metabolic stability at 15 min p.i. Approximately 5.56 to 15.3 MBq of $^{68}$Ga-LW01025, $^{68}$Ga-LW01029, $^{68}$Ga-LW01107, $^{68}$Ga-LW01108, $^{68}$Ga-LW01110, $^{68}$Ga-LW01102, or $^{68}$Ga-LW01142 were injected via tail vein into three male NRG mice, respectively. At 15 min p.i., mice were sedated and euthanized and their blood and urine were collected. The plasma was extracted from whole blood with ACN, vortexed, centrifuged, and the supernatant collected. The plasma and urine were analyzed with radio-HPLC (C18 analytical column; flow rate: 2.0 mL/min). The HPLC condition was same as the HPLC condition for quality control.

Representative radio-HPLC chromatograms of $^{68}$Ga-LW01025, $^{68}$Ga-LW01029, $^{68}$Ga-LW01107, $^{68}$Ga-LW01108, $^{68}$Ga-LW01110, $^{68}$Ga-LW01102, and $^{68}$Ga-LW01142 extracted from mouse urine and plasma samples are shown in FIGS. 2-8, respectively.

EXAMPLE 7

Synthesis of LW01045, LW01059, LW01061, LW01090, and LW01117

The chemical structures of LW01045, LW01059, LW01061, LW01090, and LW01117 are as follows:

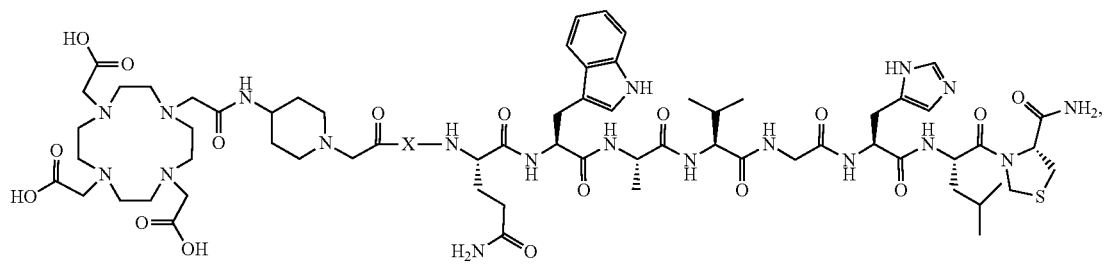

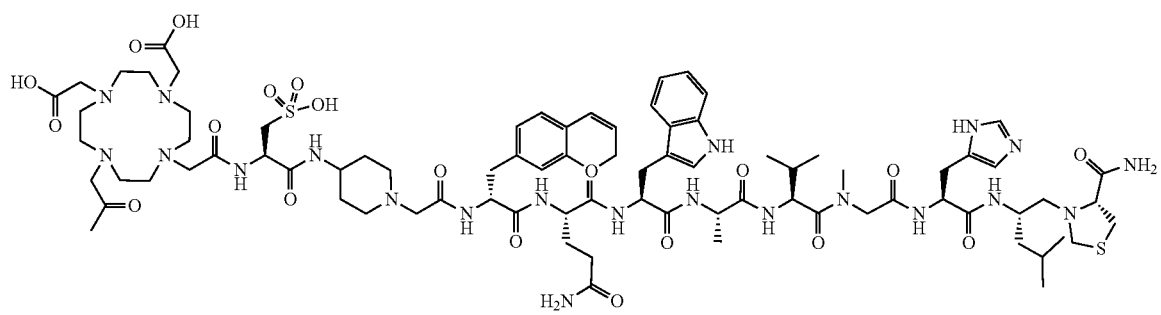

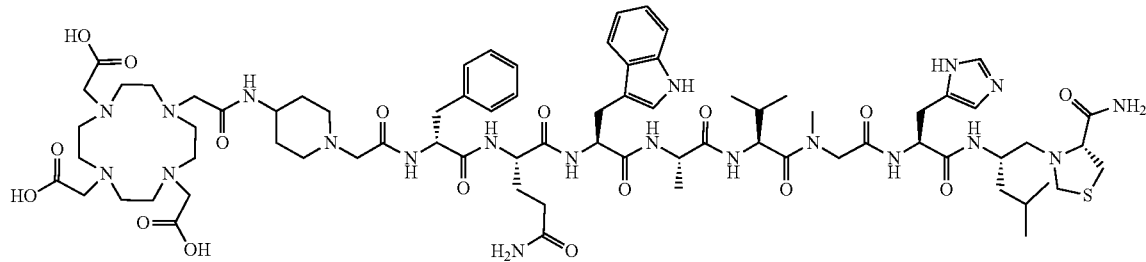

Synthesis of DOTA-Conjugated Peptides LW01045, LW01059, LW01061, LW01090, and LW01117

LW01045 (DOTA-Pip-D-Phe-Gln-Trp-Ala-Val-Gly-His-Leu-ψ-Thz-NH₂), LW01059 (DOTA-Pip-D-2-Nal-Gln-Trp-Ala-Val-Gly-His-Leu-ψ-Thz-NH₂), LW01061 (DOTA-Pip-D-Tpi-Gln-Trp-Ala-Val-Gly-His-Leu-ψ-Thz-NH₂), LW01090 (DOTA-Pip-D-Phe-Gln-Trp-Ala-Val-NMe-Gly-His-Leu-ψ-Thz-NH₂), and LW01117 (DOTA-Cysteic acid-Pip-D-2-Nal-Gln-Trp-Ala-Val-Gly-His-Leu-ψ-Thz-NH₂) wherein ψ is a reduced peptide bond, were synthesized using the Fmoc solid phase synthesis strategy starting from Sieber resin. As described in Example 1, the compound Fmoc-LeuipThz-OH (4), Fmoc-protected amino acids, Fmoc-4-amino-(1-carboxymethyl)-piperidine and DOTA (ᵗBu)₃ were sequentially coupled to the resin. After being cleaved with TFA/TIS/water/DODT/thioanisole/phenol 81.5:1:5:2.5:5:5) and precipitated with diethyl ether, the crude product was purified by HPLC (C18 semi-prep column; flow rate: 4.5 mL/min) and lyophilized. The HPLC conditions, retention times, isolated yields, and MS confirmations of DOTA-conjugated peptides are provided in Table 12.

TABLE 12

HPLC Purification conditions and MS characterizations of LW01045, LW01059, LW01061, LW01090, and LW01117

| Compound name | HPLC conditions | Retention time (min) | Yield (%) | Calculated mass (m/z) | Found (m/z) |
|---|---|---|---|---|---|
| LW01045 | 25% $CH_3CN$ and 0.1% TFA in $H_2O$ | 18.7 | 34 | $[M + 2H]^{2+}$ 792.4 | $[M + 2H]^{2+}$ 792.8 |
| LW01059 | 28% $CH_3CN$ and 0.1% TFA in $H_2O$ | 15.8 | 49 | $[M + 2H]^{2+}$ 817.4 | $[M + 2H]^{2+}$ 817.8 |
| LW01061 | 28% $CH_3CN$ and 0.1% TFA in $H_2O$ | 16.6 | 38 | $[M + 2H]^{2+}$ 817.9 | $[M + 2H]^{2+}$ 818.2 |
| LW01090 | 25% $CH_3CN$ and 0.1% TFA in $H_2O$ | 18.3 | 32 | $[M + 2H]^{2+}$ 799.4 | $[M + 2H]^{2+}$ 799.7 |
| LW01117 | 29% $CH_3CN$ and 0.1% TFA in $H_2O$ | 14.6 | 14 | $[M + 2H]^{2+}$ 892.9 | $[M + 2H]^{2+}$ 893.4 |

Synthesis of Nonradioactive Ga-Complexed Standards of LW01045, LW01059, LW01061, LW01090, and LW01117

Non-radioactive Ga-complexed standards of LW01045, LW01059, LW01061, LW01090, and LW01117 were prepared according to the procedure set forth in Example 1. Briefly, LW01045, LW01059, LW01061, LW01090, and LW01117 were mixed and incubated with 0.5 mL NaOAc buffer (0.1 N, pH 4.2-4.5) and $GaCl_3$ (5 eq., 0.2 M) at 80° C. for 15 min and then purified with HPLC (C18 semi-prep column) and lyophilized. The HPLC conditions, retention times, isolated yields and MS confirmations of these non-radioactive Ga-complexed standards are provided in Table 13.

TABLE 13

HPLC purification conditions and MS characterizations of Ga-complexed LW01045, LW01059, LW01061, LW01090, and LW01117

| Compound name | HPLC conditions | Retention time (min) | Yield (%) | Calculated mass (m/z) | Found (m/z) |
|---|---|---|---|---|---|
| Ga-LW01045 | 26% $CH_3CN$ and 0.1% TFA in $H_2O$ | 12.5 | 72 | $[M + 2H]^{2+}$ 825.9 | $[M + 2H]^{2+}$ 826.0 |
| Ga-LW01059 | 28% $CH_3CN$ and 0.1% TFA in $H_2O$ | 18.3 | 67 | $[M + 2H]^{2+}$ 850.9 | $[M + 2H]^{2+}$ 850.7 |
| Ga-LW01061 | 28% $CH_3CN$ and 0.1% TFA in $H_2O$ | 18.8 | 68 | $[M + 2H]^{2+}$ 851.4 | $[M + 2H]^{2+}$ 851.2 |
| Ga-LW01090 | 25% $CH_3CN$ and 0.1% TFA in $H_2O$ | 18.3 | 75 | $[M + 2H]^{2+}$ 832.9 | $[M + 2H]^{2+}$ 832.8 |
| Ga-LW01117 | 29% $CH_3CN$ and 0.1% TFA in $H_2O$ | 14.6 | 57 | $[M + 2H]^{2+}$ 926.4 | $[M + 2H]^{2+}$ 926.4 |

Synthesis of $^{68}$Ga-Labeled Compounds

Radiolabeled LW01045, LW01059, LW01090, and LW01117 were prepared according to the procedure set forth in Example 1. Briefly, purified $^{68}$Ga in 0.5 mL water was added into a 4-mL glass vial preloaded with 0.7 mL of HEPES buffer (2 M, pH 5.0) and 10 μL precursor solution (1 mM). The radiolabeling reaction was carried out under microwave heating for 1 min before being purified by HPLC using the semi-preparative column. The eluate fraction containing the radiolabeled product was collected, diluted with water (50 mL), and passed through a C18 Sep-Pak cartridge that was pre-washed with ethanol (10 mL) and water (10 mL). After washing the C18 Sep-Pak cartridge with water (10 mL), the $^{68}$Ga-labeled product was eluted off the cartridge with ethanol (0.4 mL), and diluted with saline for imaging and biodistribution. Quality control was performed using the analytical column. The tracers were obtained with more than 95% radiochemical purity. The HPLC conditions and retention times are provided in Table 14. The tracers were obtained in 42-59% decay-corrected radiochemical yields with >66 GB/pmol molar activity and >92% radiochemical purity.

TABLE 14

HPLC Conditions for the purification and quality control of $^{68}$Ga-labeled LW01045, LW01059, LW01090, and LW01117.

| Compound name | | HPLC conditions | Retention time (min) |
|---|---|---|---|
| [$^{68}$Ga]Ga-LW01045 | Semi-Prep | 20% $CH_3CN$ and 0.1% FA in $H_2O$; flow rate 4.5 mL/min | 12.6 |

TABLE 14-continued

HPLC Conditions for the purification and quality control of $^{68}$Ga-labeled LW01045, LW01059, LW01090, and LW01117.

| Compound name | | HPLC conditions | Retention time (min) |
|---|---|---|---|
| | QC | 23% $CH_3CN$ and 0.1% FA in $H_2O$; flow rate 2.0 mL/min | 7.2 |
| [$^{68}$Ga]Ga-LW01059 | Semi-Prep | 21% $CH_3CN$ and 0.1% FA in $H_2O$; flow rate 4.5 mL/min | 35.8 |
| | QC | 26% $CH_3CN$ and 0.1% FA in $H_2O$; flow rate 2 mL/min | 8.8 |
| [$^{68}$Ga]Ga-LW01090 | Semi-Prep | 20% $CH_3CN$ and 0.1% FA in $H_2O$; flow rate 4.5 mL/min | 10.7 |
| | QC | 23% $CH_3CN$ and 0.1% FA in $H_2O$; flow rate 2.0 mL/min | 5.1 |

TABLE 14-continued

HPLC Conditions for the purification and quality control of $^{68}$Ga-labeled LW01045, LW01059, LW01090, and LW01117.

| Compound name | | HPLC conditions | Retention time (min) |
|---|---|---|---|
| [$^{68}$Ga]Ga-LW01117 | Semi-Prep | 29% CH$_3$CN and 0.1% TFA in H$_2$O; flow rate 4.5 mL/min | 14.6 |
| | QC | 28% CH$_3$CN and 0.1% FA in H$_2$O; flow rate 2.0 mL/min | 6.7 |

In Vitro Competition Binding Assay

In vitro competition binding assays were performed according to the procedure outlined in Example 1. Specifically, the binding affinities of Ga-LW01045, Ga-LW01059, Ga-LW01090, and Ga-LW01117 were measured by a cell-based binding assay using GRPR-expressing PC-3 prostate cancer cells. Ga-LW01045, Ga-LW01059, Ga-LW01090, and Ga-LW01117 inhibited the binding of [$^{125}$I-Tyr$^4$]Bombesin in a dose dependent manner (FIGS. 9B, 10B, 11B, and 12B, respectively). The calculated Ki values of Ga-LW01045, Ga-LW01059, Ga-LW01090, and Ga-LW01117 are enumerated in Table 15.

TABLE 15

Binding affinities (Ki, nM) of GRPR-targeting peptides.
Binding affinities Ki (n = 2-3)

| Compound | Mean | SD |
|---|---|---|
| LW01045 | 7.08 | 0.65 |
| LW01059 | 4.29 | 0.46 |
| LW01061 | >400 | — |

TABLE 15-continued

Binding affinities (Ki, nM) of GRPR-targeting peptides.
Binding affinities Ki (n = 2-3)

| Compound | Mean | SD |
|---|---|---|
| LW01090 | 6.09 | 0.95 |
| LW01117 | 5.12 | 0.57 |

PET/CT Imaging and Ex Vivo Biodistribution in PC-3 Tumor-Bearing Mice

All imaging and biodistribution studies were performed using the procedure outlined in Example 1. The PC-3 tumor xenografts clearly visualized in PET images acquired at 1 h post-injection using $^{68}$Ga-LW01045, $^{68}$Ga-LW01059, $^{68}$Ga-LW01090, and $^{68}$Ga-LW01117 (FIGS. 9A, 10A, 11A, and 12A, respectively and Table 16).

TABLE 16

Biodistribution data (at 1 h post-injection, % ID/g) of $^{68}$Ga-LW01045, $^{68}$Ga-LW0159, $^{68}$Ga-LW01090, and $^{68}$Ga-LW0117 in mice bearing PC-3 tumor xenografts.

| Tissues | $^{68}$Ga-LW01045 (n = 4) | | $^{68}$Ga-LW01059 (n = 4) | | $^{68}$Ga-LW01090 (n = 4) | | $^{68}$Ga-LW01117 (n = 4) | | | |
|---|---|---|---|---|---|---|---|---|---|---|
| | Mean | SD | Mean | SD | Mean | SD | Mean | SD | Mean* | SD* |
| Blood | 0.76 | 0.21 | 2.16 | 1.86 | 0.76 | 0.08 | 1.86 | 0.12 | 2.57 | 0.68 |
| Fat | 0.09 | 0.03 | 0.19 | 0.25 | 0.11 | 0.01 | 0.25 | 0.05 | 0.58 | 0.22 |
| Testes | 0.19 | 0.05 | 0.33 | 0.60 | 0.23 | 0.02 | 0.60 | 0.16 | 1.06 | 0.13 |
| Small Intestine | 1.04 | 0.30 | 2.15 | 1.62 | 0.66 | 0.09 | 1.62 | 0.07 | 1.63 | 0.62 |
| Large Intestine | 0.37 | 0.16 | 0.66 | 0.50 | 0.41 | 0.09 | 0.50 | 0.04 | 1.16 | 0.41 |
| Spleen | 0.47 | 0.17 | 0.68 | 0.84 | 0.30 | 0.03 | 0.84 | 0.17 | 0.84 | 0.26 |
| Pancreas | 2.81 | 0.78 | 7.26 | 6.50 | 1.98 | 0.10 | 6.50 | 0.36 | 0.78 | 0.31 |
| Stomach | 0.32 | 0.08 | 1.10 | 0.57 | 0.40 | 0.15 | 0.57 | 0.07 | 0.63 | 0.20 |
| Liver | 2.61 | 0.70 | 21.5 | 12.5 | 0.64 | 0.11 | 12.5 | 0.88 | 1.87 | 0.35 |
| Adrenal Glands | 0.57 | 0.40 | 1.81 | 1.27 | 0.58 | 0.10 | 1.27 | 0.33 | 0.85 | 0.32 |
| kidneys | 2.51 | 0.59 | 4.49 | 3.84 | 3.52 | 0.41 | 3.84 | 0.43 | 22.9 | 9.41 |
| Heart | 0.27 | 0.08 | 0.66 | 0.58 | 0.24 | 0.03 | 0.58 | 0.04 | 0.87 | 0.26 |
| Lungs | 0.75 | 0.52 | 3.05 | 1.95 | 0.55 | 0.07 | 1.95 | 0.96 | 2.13 | 0.61 |
| PC-3 Tumor | 10.2 | 2.27 | 6.84 | 6.63 | 15.7 | 2.17 | 6.63 | 0.40 | 2.60 | 0.42 |
| Bone | 0.19 | 0.06 | 0.42 | 0.26 | 0.10 | 0.04 | 0.26 | 0.07 | 0.70 | 0.35 |
| Muscle | 0.15 | 0.05 | 0.28 | 0.35 | 0.20 | 0.08 | 0.35 | 0.14 | 0.91 | 0.37 |
| Brain | 0.05 | 0.03 | 0.06 | 0.05 | 0.03 | 0.01 | 0.05 | 0.00 | 0.08 | 0.02 |
| Tumor/bone | 61.3 | 25.0 | 17.0 | 27.5 | 175 | 82.4 | 27.5 | 7.98 | 4.37 | 1.99 |
| Tumor/muscle | 70.1 | 14.2 | 26.0 | 20.5 | 82.3 | 19.2 | 20.5 | 6.45 | 3.21 | 1.18 |
| Tumor/blood | 14.0 | 3.48 | 3.28 | 3.58 | 20.6 | 2.96 | 3.58 | 0.24 | 1.05 | 0.25 |
| Tumor/kidney | 4.10 | 0.46 | 1.55 | 1.73 | 4.48 | 0.69 | 1.73 | 0.13 | 0.13 | 0.05 |
| Tumor/pancreas | 3.70 | 0.55 | 0.98 | 1.02 | 7.95 | 1.40 | 1.02 | 0.05 | 3.77 | 1.50 |

*1 h blocked

In Vivo Stability of $^{68}$Ga-LW01045 and $^{68}$Ga-LW01090

Figure 9A:
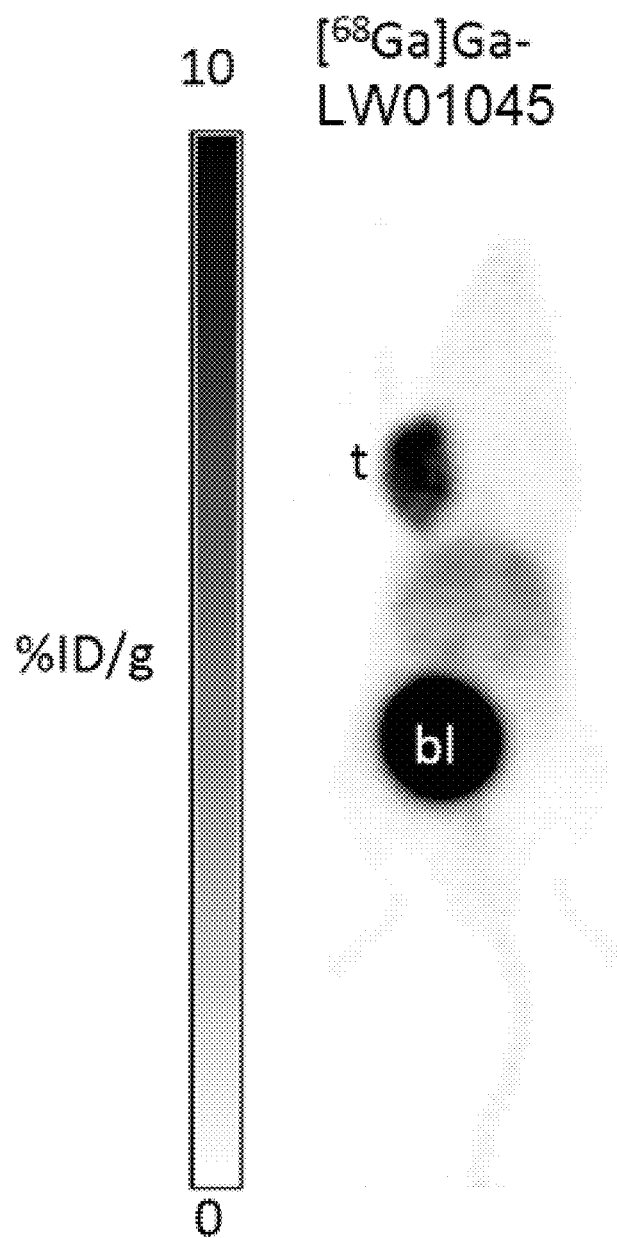
FIGS. 9A-9C show representative data of $^{68}$Ga-LW01045, including a representative maximum-intensity-projection PET image of $^{68}$Ga-LW01045 in a mouse bearing a PC-3 tumor xenograft (FIG. 9A); a representative displacement curve of [$^{125}$I-Tyr$^4$] Bombesin by Ga-LW01045 generated using GRPR-expressing PC-3 cells (FIG. 9B); and radio-HPLC chromatograms of $^{68}$Ga-LW01045 extracted from mouse urine and plasma samples (FIG. 9C).
Figure 9B:
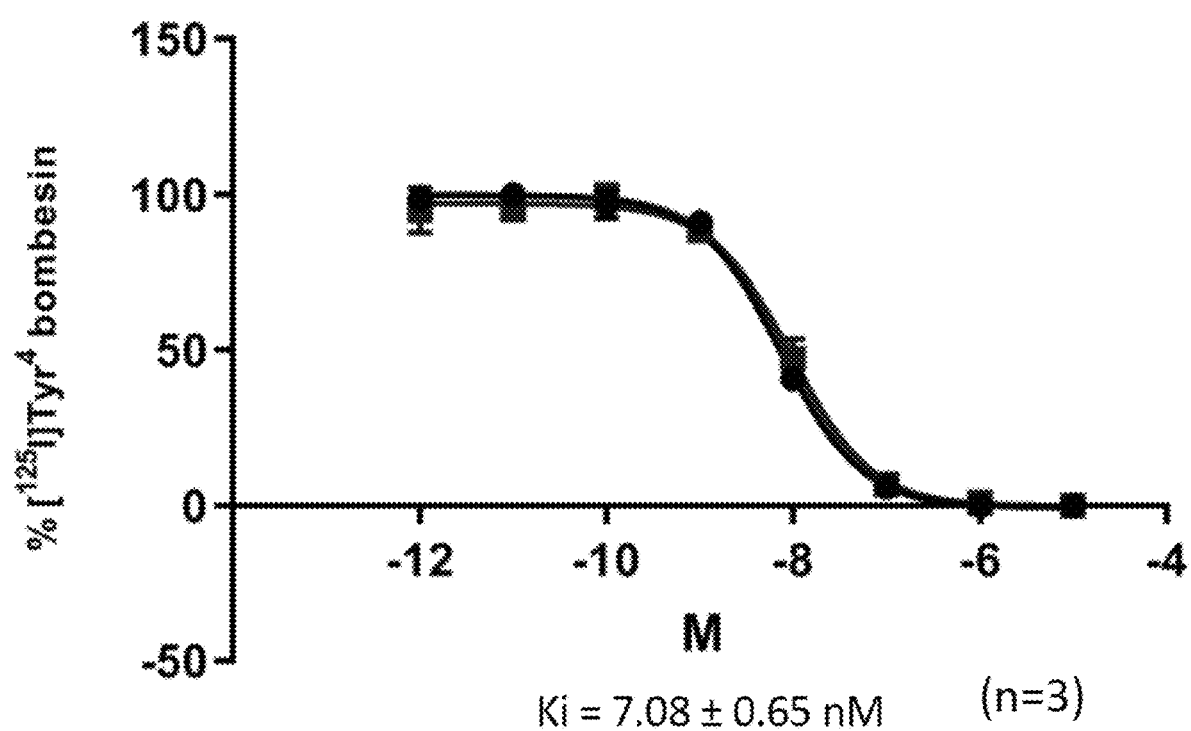
Figure 9C:
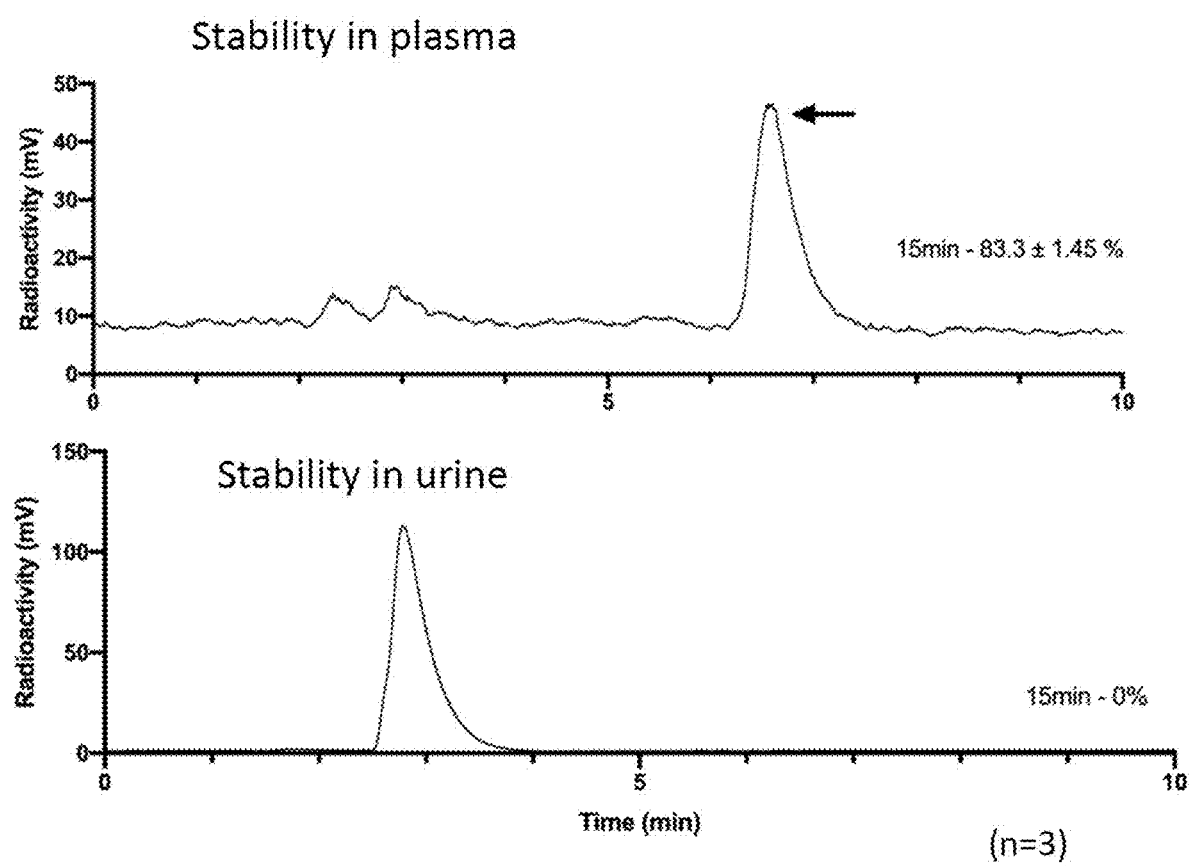
Figure 10A:
FIGS. 10A-10B show representative data of $^{68}$Ga-LW01059, including a maximum-intensity-projection PET image of $^{68}$Ga-LW01059 in a mouse bearing a PC-3 tumor xenograft (FIG. 10A); and a displacement curve of [$^{125}$I-Tyr$^4$] Bombesin by Ga-LW01059 generated using GRPR-expressing PC-3 cells (FIG. 10B).
Figure 10B:
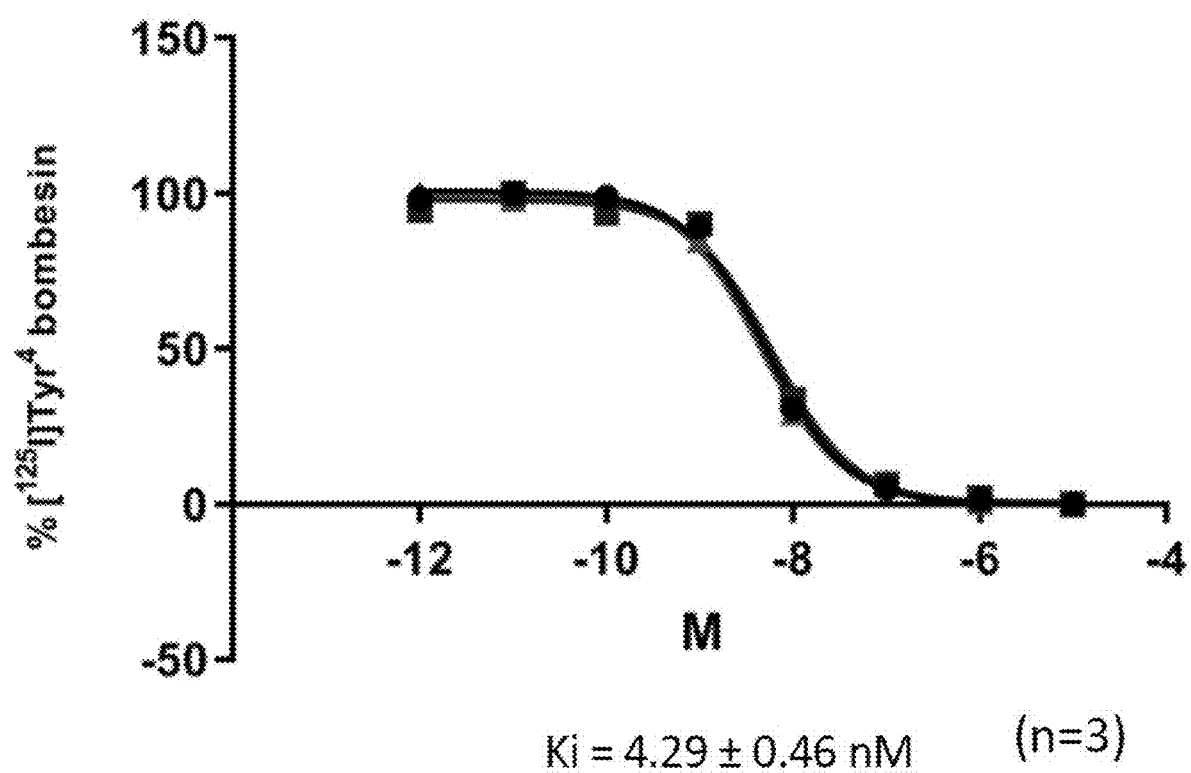
Figure 11A:
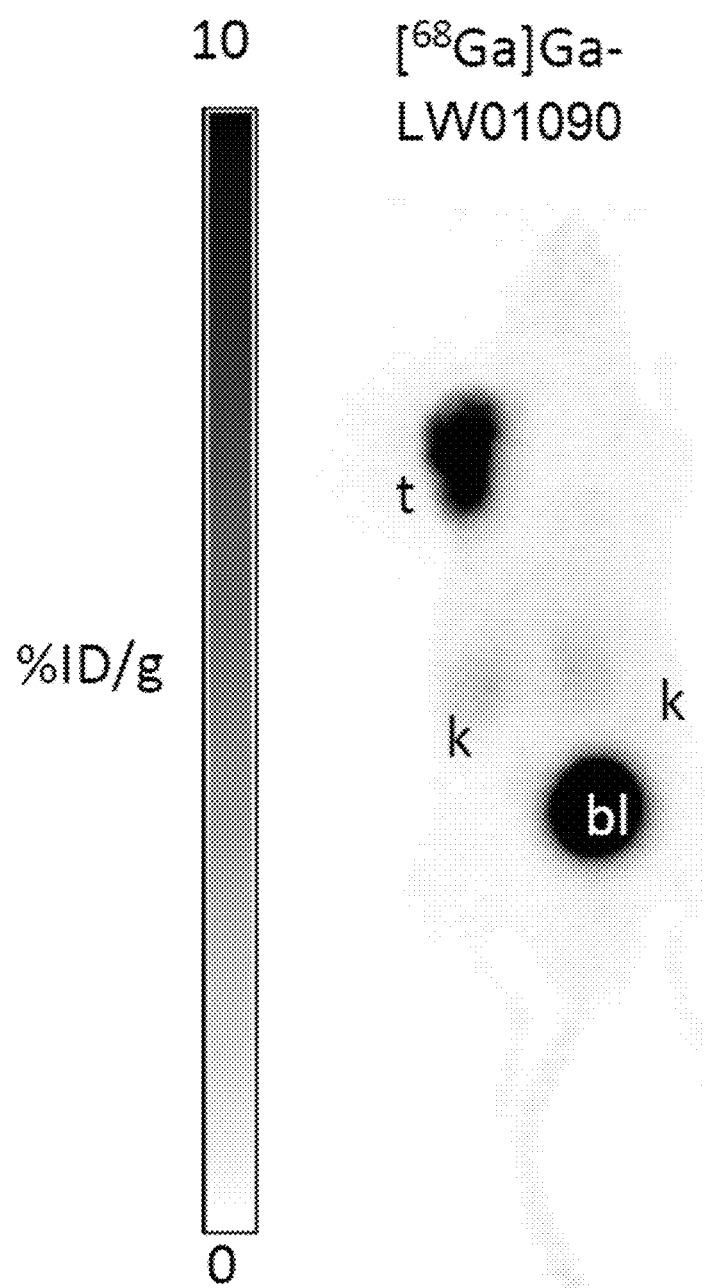
FIGS. 11A-11C show representative data of $^{68}$Ga-LW01090, including a maximum-intensity-projection PET image of $^{68}$Ga-LW01090 in a mouse bearing a PC-3 tumor xenograft (FIG. 11A); a displacement curve of [$^{125}$I-Tyr$^4$] Bombesin by Ga-LW01090 generated using GRPR-expressing PC-3 cells (FIG. 11B); and radio-HPLC chromatograms of $^{68}$Ga-LW01090 extracted from mouse urine and plasma samples (FIG. 11O).
Figure 11B:
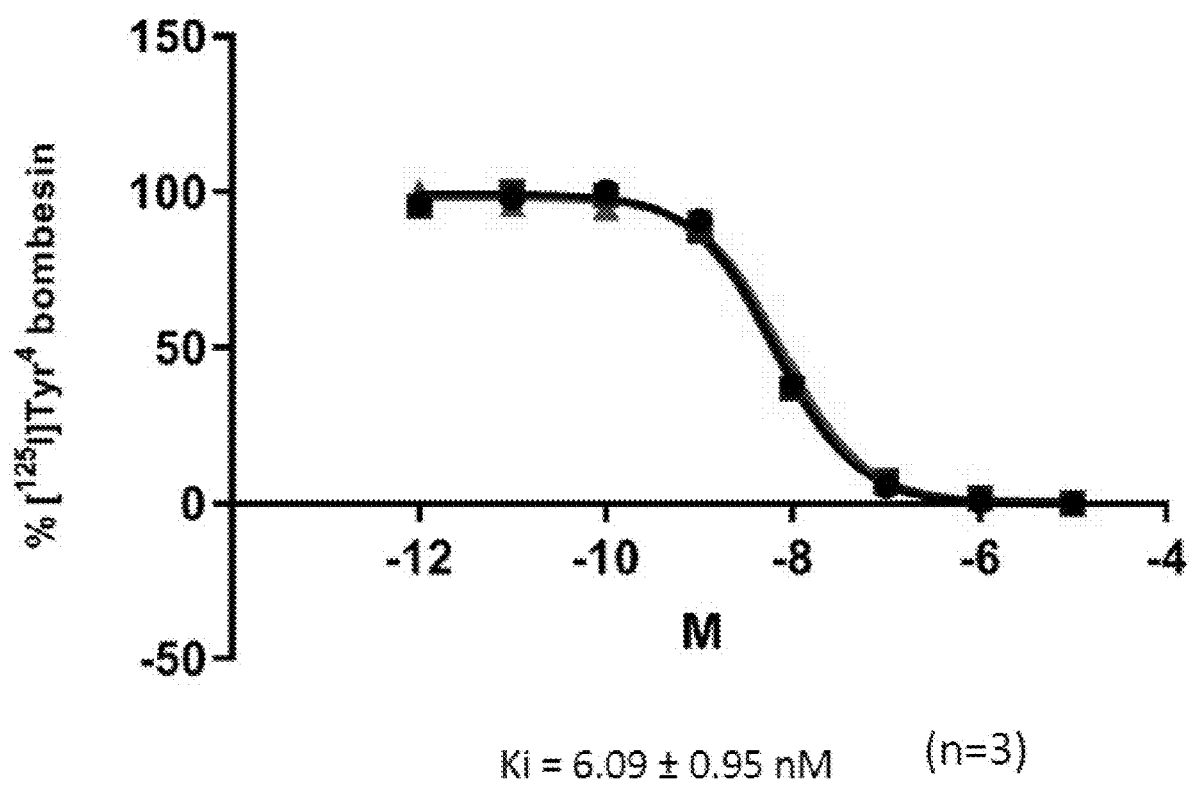
Figure 11C:
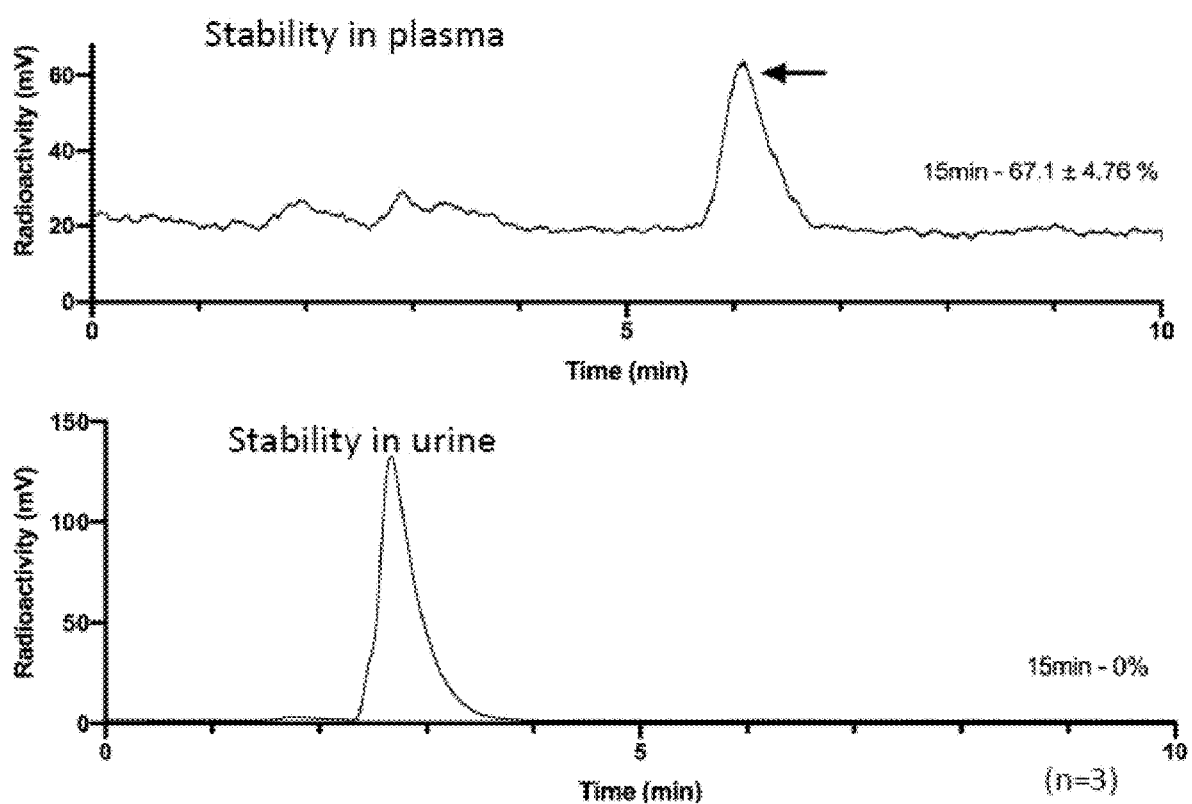
Figure 12A:
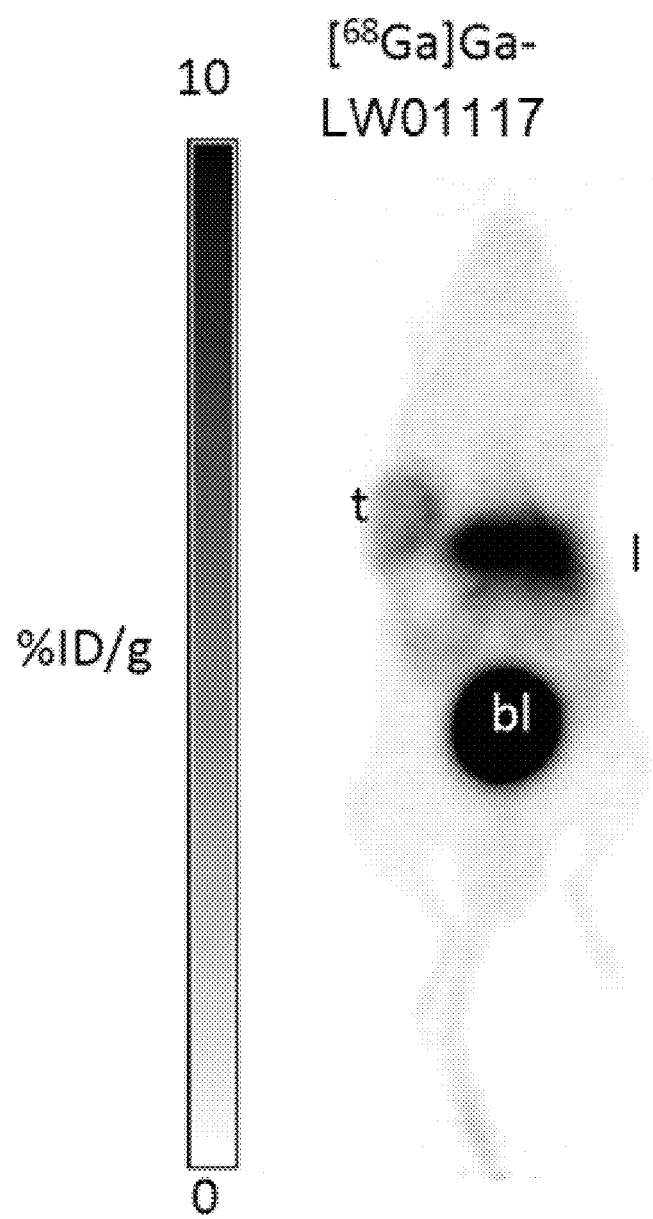
FIGS. 12A-12B show representative data of $^{68}$Ga-LW01117, including a maximum-intensity-projection PET image of $^{68}$Ga-LW01117 in a mouse bearing a PC-3 tumor xenograft (FIG. 12A); and a representative displacement curve of [$^{125}$I-Tyr$^4$] Bombesin by Ga-LW01117 generated using GRPR-expressing PC-3 cells (FIG. 12B).
Figure 12B:
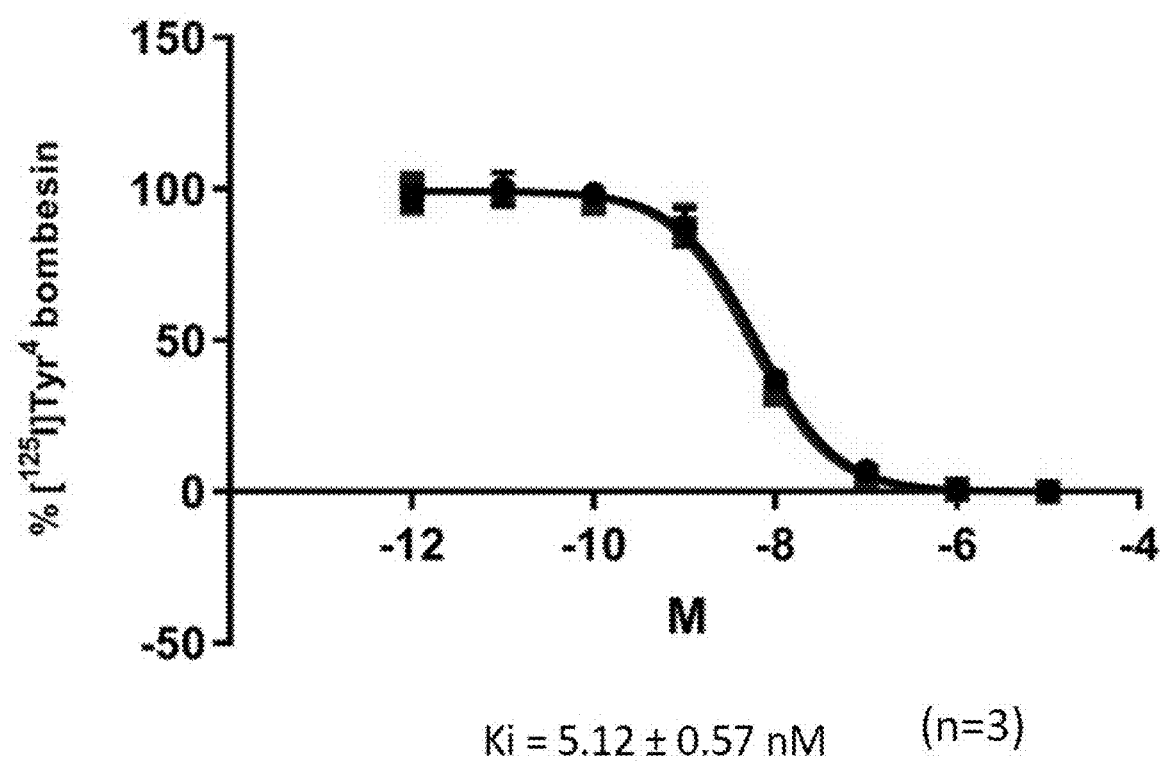

The in vivo studies were similarly performed according to the procedure set forth in Example 1. For these studies, $^{68}$Ga-LW01045 and $^{68}$Ga-LW01090 was injected via the lateral caudal vein into healthy male NRG mice (n=3). At 15 min post-injection, the mice were sedated and euthanized, and urine and blood were collected. The plasma was extracted from whole blood by the addition of CH$_3$CN (500 µL), vortexing, centrifugation, and the separation of the supernatants. The plasma and urine samples were analyzed via radio-HPLC by using the conditions for quality control of these $^{68}$Ga-labeled radioligands. FIGS. 9C and 11C show that $^{68}$Ga-LW01045 and $^{68}$Ga-LW01090 were sufficiently stable in vivo in NRG mice with 83.3±1.45% and 67.1±4.76% remaining intact in plasma post-injection. The present invention has been described with regard to one or more embodiments.

EXAMPLE 8

Synthesis of LW02045 and LW02042

The chemical structures of LW02045 and LW02042 are as follows:

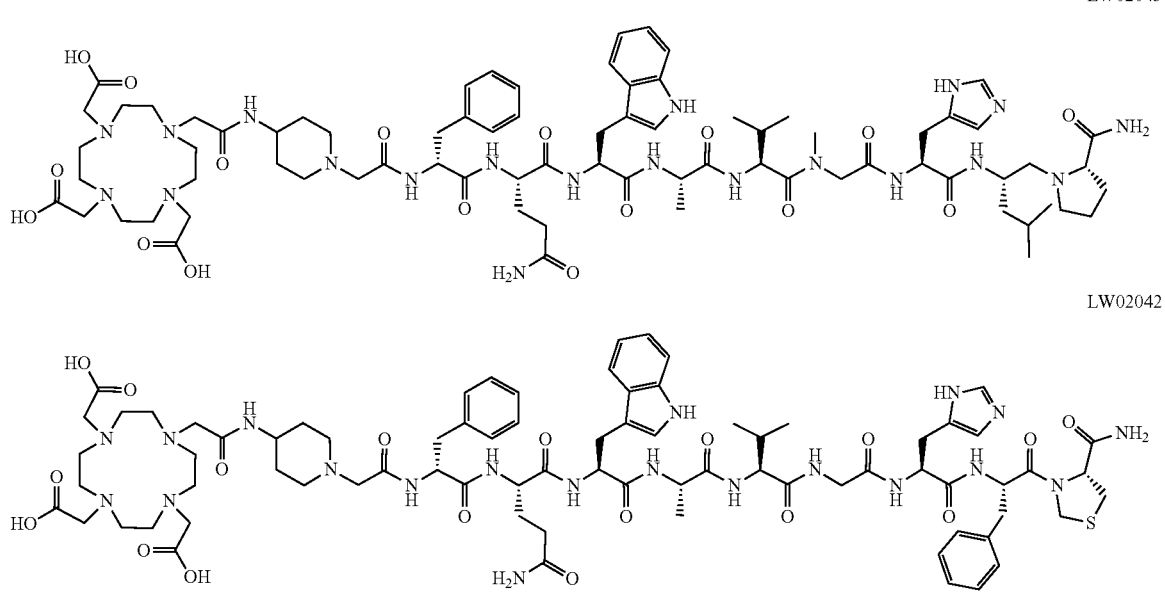

Synthesis of DOTA-Conjugated LW02045 and LW02042

LW02045 (DOTA-Pip-D-Phe-Gln-Trp-Ala-Val-N-MeGly-His-LeuψPro-NH$_2$), wherein ψ is a reduced peptide bond, was synthesized using standard Fmoc solid phase synthesis strategy starting from Sieber resin. Fmoc-LeuψPro-OH, Fmoc-protected amino acids, Fmoc-4-amino-(1-carboxymethyl)-piperidine and DOTA(tBu)$_3$ were sequentially coupled to the resin. After being cleaved with TFA/TIS/water/DODT/thioanisole/phenol 81.5:1:5:2.5:5:5) and precipitated with diethyl ether, the crude product was purified by HPLC (C18 semi-prep column; flow rate: 4.5 mL/min) and lyophilized to give a white powder. The HPLC condition was 20% ACN and 0.1% TFA in water (retention time=20.1 min); yield: 37%. ESI-MS: calculated [M+2H]2+ for LW02045 C$_{76}$H$_{114}$N$_{20}$O$_{17}$S 790.44; found 790.50.

LW02042 (DOTA-Pip-D-Phe-Gln-Trp-Ala-Val-Gly-His-Phe-Thz-NH$_2$) was synthesized using standard Fmoc solid phase synthesis. Fmoc-protected amino acids, Fmoc-4-amino-(1-carboxymethyl) piperidine and DOTA(tBu)$_3$ were sequentially coupled to the Fmoc-Rink amide-MBHA resin. After being cleaved with TFA/TIS/water/DODT/thioanisole/phenol 81.5:1:5:2.5:5:5 and precipitated by diethyl ether, the crude products were purified with HPLC (C18 semi-prep column; flow rate: 4.5 mL/min) and lyophilized to give white powders. The HPLC condition was 23% ACN and 0.1%TFA in water (retention time=11.4 min); yield: 31%. ESI-MS: calculated [M+2H]2+ for LW02042 C$_{77}$H$_{116}$N$_{20}$O$_{18}$S 816.40; found 816.44.

Syntheses of Nonradioactive Ga-Complexed Standards of LW02045 and LW02042

LW02045 (2.85 mg) and LW02042 (2.91 mg) were dissolved respectively in 0.5 mL NaOAc buffer (0.1 N, pH 4.48) and GaCl$_3$ (5 eq., 0.2 M) was added. The reaction mixture was incubated at 80 oC for 15 min and then purified with HPLC (C18 semi-prep column) and lyophilized to give white powders.

For Ga-LW02045, the HPLC condition was 20% ACN and 0.1%TFA in water at a flow rate of 4.5 mL/min (retention time=23.6 min); yield: 74%. ESI-MS: calculated [M+2H]2+ for Ga-LW02045 C$_{76}$H$_{112}$GaN$_{20}$O$_{17}$S 823.90; found 823.86. For Ga-LW02042, the HPLC condition was 23% ACN and 0.1%TFA in water at a flow rate of 4.5 mL/min (retention time=18.9 min); yield: 91%. ESI-MS: calculated [M+2H]2+ for Ga-LW02042 C$_{77}$H$_{104}$GaN$_{20}$O$_{18}$S 849.85; found 849.63.

PET/CT Imaging and Ex Vivo Biodistribution in PC-3 Tumor-Bearing Mice

All imaging and biodistribution studies were performed using male NOD.Cg-Rag1tm1Mom Il2rgtm1WjI/SzJ (NRG) mice and conducted according to the guidelines established by the Canadian Council on Animal Care and approved by Animal Ethics Committee of the University of British Columbia. For tumor inoculations, mice were anesthetized by inhalation with 2% isoflurane in oxygen and implanted subcutaneously with 5×106 PC-3 cells below the left shoulder. Imaging and biodistribution studies were performed only after tumors grew to 5-8 mm in diameter.

Figure 13:
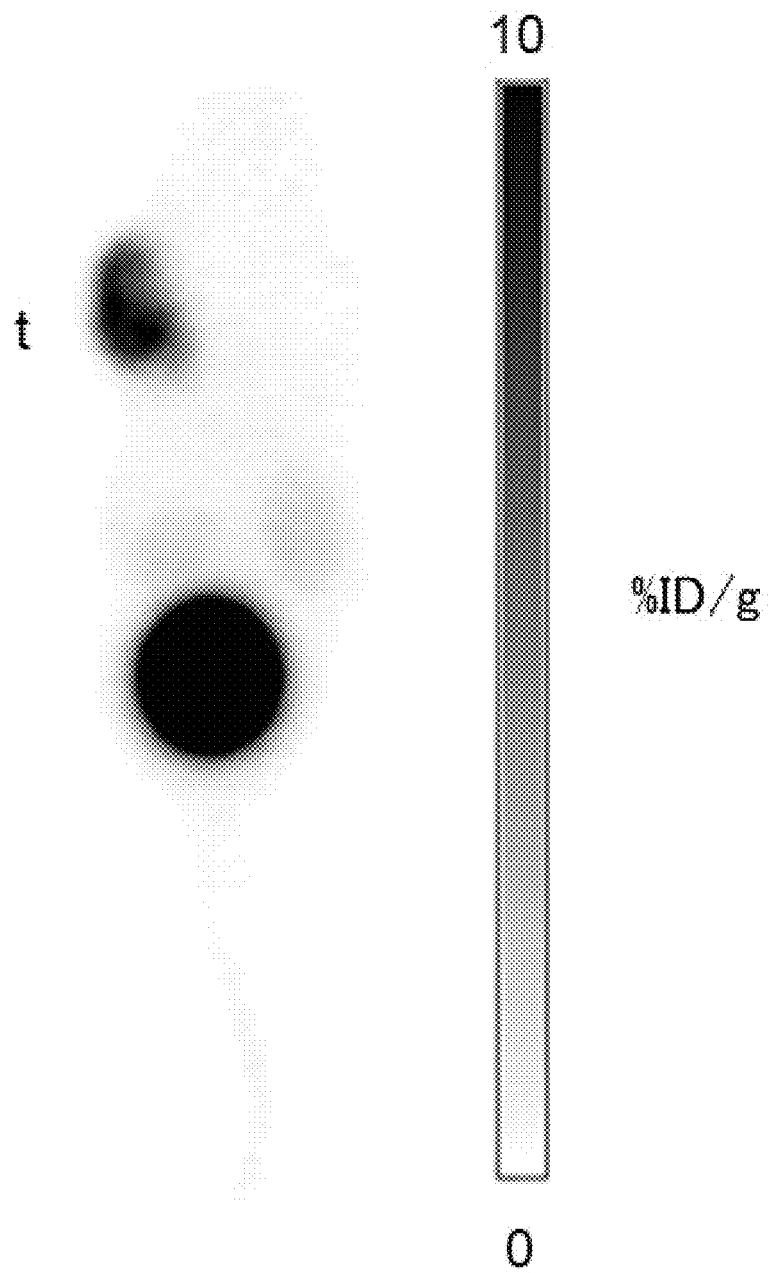
FIG. 13 shows a representative maximum-intensity-projection PET image of $^{68}$Ga-LW02045 in a mouse bearing a PC-3 tumor xenograft.

For PET/CT imaging studies, ~5 MBq of the $^{68}$Ga-labeled tracer was injected through the tail vein. Mice were allowed to recover and roam freely in the cages after injecting the tracer. At 45 min post-injection (p.i.), mice were sedated again and positioned on the scanner. First, a 10 min CT scan was conducted for localization and attenuation correction for reconstruction of PET images, before a 10 min PET image was acquired. Heating pads were used during the entire procedure to keep the mice warm. For ex vivo biodistribution studies, mice were injected with ~3 MBq of the 68Ga-labeled tracer. At 1 h p.i., mice were euthanized, blood was drawn from heart, and organs/tissues of interest were collected, rinsed with PBS, blotted dry, weighed, and counted using an automated gamma counter. The uptake in each organ/tissue was normalized to the injected dose and expressed as the percentage of the injected dose per gram of tissue (% ID/g) (FIG. 13 and Table 17).

TABLE 17

Biodistribution data (at 1 h post-injection, % ID/g) of $^{68}$Ga-LW02045 in mice bearing PC-3 tumor xenografts.
$^{68}$Ga-LW02045 (n = 4)

| Tissues | Mean | SD |
| --- | --- | --- |
| PC-3 tumor | 12.44 | 1.35 |
| Blood | 0.43 | 0.09 |
| Fat | 0.03 | 0.01 |
| Seminal | 3.80 | 7.44 |
| Testes | 0.12 | 0.02 |
| Small Intestine | 0.48 | 0.14 |
| Large Intestine | 0.34 | 0.16 |
| Spleen | 0.18 | 0.04 |
| Pancreas | 1.37 | 0.40 |
| Stomach | 0.35 | 0.17 |
| Liver | 0.37 | 0.07 |
| Adrenal | 0.44 | 0.15 |
| Kidneys | 2.54 | 0.54 |
| Heart | 0.14 | 0.02 |
| Lungs | 1.08 | 0.16 |

TABLE 17-continued

Biodistribution data (at 1 h post-injection, % ID/g) of $^{68}$Ga-LW02045 in mice bearing PC-3 tumor xenografts.
$^{68}$Ga-LW02045 (n = 4)

| Tissues | Mean | SD |
| --- | --- | --- |
| Bone | 0.07 | 0.01 |
| Muscle | 0.10 | 0.01 |
| Brain | 0.02 | 0.00 |

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes. It will be apparent to persons skilled in the art that a number of variations and modifications can be made without departing from the scope of the invention as defined in the following claims. The scope of the invention should therefore not be limited by the preferred embodiments set forth in the above Examples, but should be given the broadest interpretation consistent with the description as a whole.

What is claimed is:

1. A peptidic compound having the structure: optionally complexed with a radiometal:

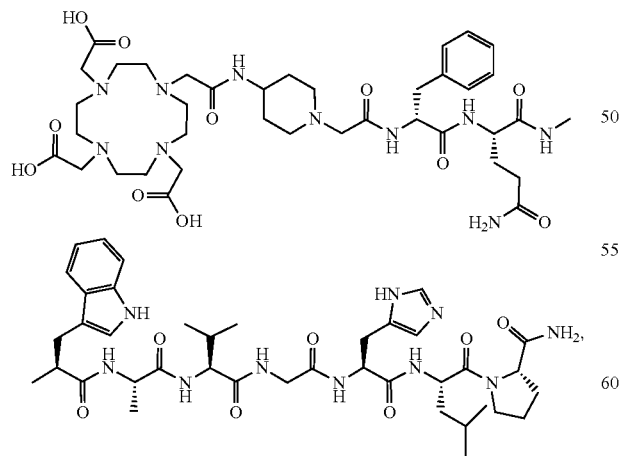

or a salt or a solvate thereof.

2. A peptidic compound having the structure: optionally complexed with a radiometal:

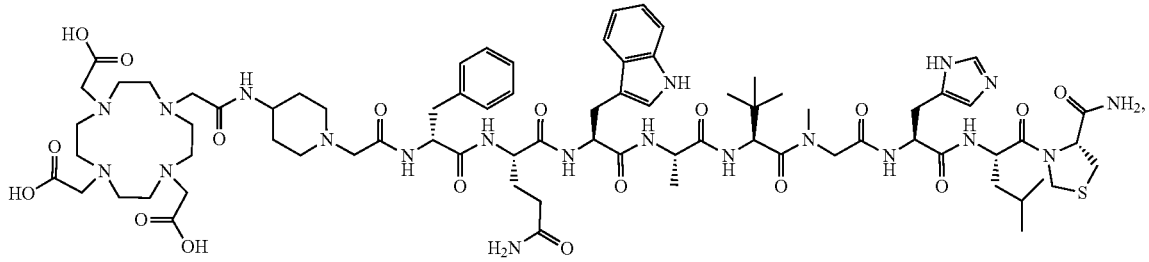 [SMILES: CC(C)C[C@H](NC(=O)[C@H](Cc1cnc[nH]1)NC(=O)CN(C)C(=O)[C@@H](NC(=O)[C@H](C)NC(=O)[C@H](Cc1c[nH]c2ccccc12)NC(=O)[C@H](CCC(N)=O)NC(=O)[C@@H](Cc1ccccc1)NC(=O)CN1CCC(NC(=O)CN2CCN(CC(=O)O)CCN(CC(=O)O)CCN(CC(=O)O)CC2)CC1)C(C)(C)C)C(=O)N1CSC[C@H]1C(N)=O]

or a salt or a solvate thereof.

3. The peptidic compound of claim 1, wherein the peptidic compound is complexed with $^{68}$Ga, $^{61}$Cu, $^{64}$Cu, $^{67}$Ga, $^{99m}$Tc, $^{110m}$In, $^{111}$In, $^{44}$Sc, $^{86}$Y, $^{89}$Zr, $^{90}$Nb, $^{152}$Tb, $^{155}$Tb, $^{203}$Pb or $^{72}$As.

4. The peptidic compound of claim 1, wherein the peptidic compound is complexed with $^{68}$Ga.

5. A pharmaceutical composition comprising a peptidic compound of claim 1, and a pharmaceutically acceptable carrier.

6. A method of imaging Gastrin-releasing peptide receptor (GRPR) in a subject, the method comprising: administering to the subject a peptidic compound of claim 1; and imaging tissue of the subject.

7. A method of imaging Gastrin-releasing peptide receptor (GRPR) in a subject, the method comprising: administering to the subject a peptidic compound of claim 3; and imaging tissue of the subject.

8. A method of imaging Gastrin-releasing peptide receptor (GRPR) in a subject, the method comprising: administering to the subject a peptidic compound of claim 4; and imaging tissue of the subject.

9. The peptidic compound of claim 2, wherein the peptidic compound is complexed with $^{68}$Ga, $^{61}$Cu, $^{64}$Cu, $^{67}$Ga, $^{99m}$Tc, $^{110m}$In, $^{111}$In, $^{44}$Sc, $^{86}$Y, $^{89}$Zr, $^{90}$Nb, $^{152}$Tb, $^{155}$Tb, $^{203}$Pb or $^{72}$As.

10. The peptidic compound of claim 2, wherein the peptidic compound is complexed with $^{68}$Ga.

11. A pharmaceutical composition comprising a peptidic compound of claim 2, and a pharmaceutically acceptable carrier.

12. A method of imaging Gastrin-releasing peptide receptor (GRPR) in a subject, the method comprising: administering to the subject a peptidic compound of claim 9; and imaging tissue of the subject.

13. A method of imaging Gastrin-releasing peptide receptor (GRPR) in a subject, the method comprising: administering to the subject a peptidic compound of claim 10; and imaging tissue of the subject.

14. The peptidic compound of claim 1, wherein the peptidic compound is complexed with $^{225}$Ac.

* * * * *

UNITED STATES PATENT AND TRADEMARK OFFICE
CERTIFICATE OF CORRECTION

PATENT NO. : 12,246,076 B2
APPLICATION NO. : 18/512708
DATED : March 11, 2025
INVENTOR(S) : Kuo-Shyan Lin et al.

Page 1 of 1

It is certified that error appears in the above-identified patent and that said Letters Patent is hereby corrected as shown below:

In the Claims

At Column 137, Line 43:
"1. A peptidic compound having the structure: optionally"
Should read:
-- 1. A peptidic compound having the structure, optionally --

At Column 137, Line 66:
"2. A peptidic compound having the structure: optionally"
Should read:
-- 2. A peptidic compound having the structure, optionally --

Signed and Sealed this
Twenty-seventh Day of May, 2025

Coke Morgan Stewart
*Acting Director of the United States Patent and Trademark Office*

SEQUENCE LISTING

```
Sequence total quantity: 70
SEQ ID NO: 1              moltype = AA   length = 9
FEATURE                   Location/Qualifiers
SITE                      1
                          note = N-terminus is modified
SITE                      1
                          note = D-Phenylalanine
SITE                      6
                          note = Gly or meGly
SITE                      8..9
                          note = joined by a reduced peptide bond
SITE                      9
                          note = thiazoline-4-carboxylic acid
SITE                      9
                          note = C-terminally amidated
source                    1..9
                          mol_type = protein
                          organism = synthetic construct
SEQUENCE: 1
FQWAVXHLX                                                                         9

SEQ ID NO: 2              moltype = AA   length = 9
FEATURE                   Location/Qualifiers
SITE                      1
                          note = D-Phenylalanine
SITE                      9
                          note = thiazoline-4-carboxylic acid
SITE                      9
                          note = C-terminally amidated
source                    1..9
                          mol_type = protein
                          organism = synthetic construct
SEQUENCE: 2
FQWAVGHLX                                                                         9

SEQ ID NO: 3              moltype = AA   length = 9
FEATURE                   Location/Qualifiers
SITE                      1
                          note = D-3-(2-naphtyl)alanine
SITE                      9
                          note = thiazoline-4-carboxylic acid
SITE                      9
                          note = C-terminally amidated
source                    1..9
                          mol_type = protein
                          organism = synthetic construct
```

```
SEQUENCE: 3
XQWAVGHLX                                                                              9

SEQ ID NO: 4            moltype = AA  length = 9
FEATURE                 Location/Qualifiers
SITE                    1
                        note = D-Phenylalanine
SITE                    9
                        note = thiazoline-4-carboxylic acid
SITE                    9
                        note = C-terminally amidated
source                  1..9
                        mol_type = protein
                        organism = synthetic construct
SEQUENCE: 4
FQWAVGHLX                                                                              9

SEQ ID NO: 5            moltype = AA  length = 9
FEATURE                 Location/Qualifiers
SITE                    1
                        note = D-Phenylalanine
SITE                    5
                        note = tranexamic acid, tert-leucine
SITE                    9
                        note = thiazoline-4-carboxylic acid
SITE                    9
                        note = C-terminally amidated
source                  1..9
                        mol_type = protein
                        organism = synthetic construct
SEQUENCE: 5
FQWAXGHLX                                                                              9

SEQ ID NO: 6            moltype = AA  length = 9
FEATURE                 Location/Qualifiers
SITE                    5
                        note = tranexamic acid, tert-leucine
MOD_RES                 7
                        note = N-Methylhistidine
SITE                    9
                        note = thiazoline-4-carboxylic acid
SITE                    9
                        note = C-terminally amidated
source                  1..9
                        mol_type = protein
                        organism = synthetic construct
SEQUENCE: 6
FQWAXGHLX                                                                              9

SEQ ID NO: 7            moltype = AA  length = 9
FEATURE                 Location/Qualifiers
SITE                    1
                        note = D-Phenylalanine
SITE                    8..9
                        note = joined by a reduced peptide bond
SITE                    9
                        note = thiazoline-4-carboxylic acid
SITE                    9
                        note = C-terminally amidated
source                  1..9
                        mol_type = protein
                        organism = synthetic construct
SEQUENCE: 7
FHWAVGHLX                                                                              9

SEQ ID NO: 8            moltype = AA  length = 9
FEATURE                 Location/Qualifiers
SITE                    1
                        note = D-Phenylalanine
SITE                    5
                        note = tranexamic acid, tert-leucine
MOD_RES                 7
                        note = N-Methylhistidine
SITE                    9
                        note = thiazoline-4-carboxylic acid
SITE                    9
                        note = C-terminally amidated
source                  1..9
                        mol_type = protein
```

```
                        organism = synthetic construct
SEQUENCE: 8
FHWAXGHLX                                                                           9

SEQ ID NO: 9            moltype = AA   length = 9
FEATURE                 Location/Qualifiers
SITE                    1
                        note = D-Phenylalanine
SITE                    5
                        note = tranexamic acid, tert-leucine
SITE                    8..9
                        note = joined by a reduced peptide bond
SITE                    9
                        note = thiazoline-4-carboxylic acid
SITE                    9
                        note = C-terminally amidated
source                  1..9
                        mol_type = protein
                        organism = synthetic construct
SEQUENCE: 9
FQWAXGHLX                                                                           9

SEQ ID NO: 10           moltype = AA   length = 10
FEATURE                 Location/Qualifiers
SITE                    1
                        note = N-terminus is modified with
                        1,4,7,10-tetraazacyclododecane- 1,4,7,10-tetraacetic acid
SITE                    1
                        note = 4-amino-1-carboxymethyl-piperidine
SITE                    2
                        note = D-Phenylalanine
SITE                    10
                        note = thiazoline-4-carboxylic acid
SITE                    10
                        note = C-terminally amidated
source                  1..10
                        mol_type = protein
                        organism = synthetic construct
SEQUENCE: 10
XFQWAVGHLX                                                                          10

SEQ ID NO: 11           moltype = AA   length = 10
FEATURE                 Location/Qualifiers
SITE                    1
                        note = N-terminus is modified with
                        1,4,7,10-tetraazacyclododecane- 1,4,7,10-tetraacetic acid
SITE                    1
                        note = 4-amino-1-carboxymethyl-piperidine
SITE                    2
                        note = D-3-(2-naphtyl)alanine
SITE                    10
                        note = thiazoline-4-carboxylic acid
SITE                    10
                        note = C-terminally amidated
source                  1..10
                        mol_type = protein
                        organism = synthetic construct
SEQUENCE: 11
XXQWAVGHLX                                                                          10

SEQ ID NO: 12           moltype = AA   length = 10
FEATURE                 Location/Qualifiers
SITE                    1
                        note = N-terminus is modified with
                        1,4,7,10-tetraazacyclododecane- 1,4,7,10-tetraacetic acid
SITE                    1
                        note = 4-amino-1-carboxymethyl-piperidine
SITE                    2
                        note = D-Phenylalanine
MOD_RES                 8
                        note = N-Methylhistidine
SITE                    10
                        note = thiazoline-4-carboxylic acid
SITE                    10
                        note = C-terminally amidated
source                  1..10
                        mol_type = protein
                        organism = synthetic construct
SEQUENCE: 12
```

```
XFQWAVGHLX                                                                      10

SEQ ID NO: 13          moltype = AA  length = 10
FEATURE                Location/Qualifiers
SITE                   1
                       note = N-terminus is modified with
                       1,4,7,10-tetraazacyclododecane- 1,4,7,10-tetraacetic acid
SITE                   1
                       note = 4-amino-1-carboxymethyl-piperidine
SITE                   2
                       note = D-Phenylalanine
SITE                   6
                       note = tranexamic acid, tert-leucine
SITE                   10
                       note = thiazoline-4-carboxylic acid
SITE                   10
                       note = C-terminally amidated
source                 1..10
                       mol_type = protein
                       organism = synthetic construct
SEQUENCE: 13
XFQWAXGHLX                                                                      10

SEQ ID NO: 14          moltype = AA  length = 10
FEATURE                Location/Qualifiers
SITE                   1
                       note = N-terminus is modified with
                       1,4,7,10-tetraazacyclododecane- 1,4,7,10-tetraacetic acid
SITE                   1
                       note = 4-amino-1-carboxymethyl-piperidine
SITE                   2
                       note = D-Phenylalanine
SITE                   6
                       note = tranexamic acid, tert-leucine
MOD_RES                8
                       note = N-Methylhistidine
SITE                   10
                       note = thiazoline-4-carboxylic acid
SITE                   10
                       note = C-terminally amidated
source                 1..10
                       mol_type = protein
                       organism = synthetic construct
SEQUENCE: 14
XFQWAXGHLX                                                                      10

SEQ ID NO: 15          moltype = AA  length = 10
FEATURE                Location/Qualifiers
SITE                   1
                       note = N-terminus is modified with
                       1,4,7,10-tetraazacyclododecane- 1,4,7,10-tetraacetic acid
SITE                   1
                       note = 4-amino-1-carboxymethyl-piperidine
SITE                   2
                       note = D-Phenylalanine
SITE                   6
                       note = tranexamic acid, tert-leucine
MOD_RES                8
                       note = N-Methylhistidine
SITE                   10
                       note = thiazoline-4-carboxylic acid
SITE                   10
                       note = C-terminally amidated
source                 1..10
                       mol_type = protein
                       organism = synthetic construct
SEQUENCE: 15
XFHWAXGHLX                                                                      10

SEQ ID NO: 16          moltype = AA  length = 10
FEATURE                Location/Qualifiers
SITE                   1
                       note = N-terminus is modified with
                       1,4,7,10-tetraazacyclododecane- 1,4,7,10-tetraacetic acid
SITE                   1
                       note = 4-amino-1-carboxymethyl-piperidine
SITE                   2
                       note = D-Phenylalanine
SITE                   9..10
```

-continued

```
                        note = joined by a reduced peptide bond
SITE                    10
                        note = thiazoline-4-carboxylic acid
SITE                    10
                        note = C-terminally amidated
source                  1..10
                        mol_type = protein
                        organism = synthetic construct
SEQUENCE: 16
XFHWAVGHLX                                                                            10

SEQ ID NO: 17           moltype = AA  length = 10
FEATURE                 Location/Qualifiers
SITE                    1
                        note = N-terminus is modified with
                         1,4,7,10-tetraazacyclododecane- 1,4,7,10-tetraacetic acid
SITE                    1
                        note = 4-amino-1-carboxymethyl-piperidine
SITE                    2
                        note = D-Phenylalanine
SITE                    6
                        note = tranexamic acid, tert-leucine
SITE                    9..10
                        note = joined by a reduced peptide bond
SITE                    10
                        note = thiazoline-4-carboxylic acid
SITE                    10
                        note = C-terminally amidated
source                  1..10
                        mol_type = protein
                        organism = synthetic construct
SEQUENCE: 17
XFQWAXGHLX                                                                            10

SEQ ID NO: 18           moltype = AA  length = 9
FEATURE                 Location/Qualifiers
SITE                    1
                        note = D-Phenylalanine
SITE                    5
                        note = tranexamic acid, tert-leucine
SITE                    9
                        note = thiazoline-4-carboxylic acid
SITE                    9
                        note = C-terminally amidated
source                  1..9
                        mol_type = protein
                        organism = synthetic construct
SEQUENCE: 18
FQWAXGHLX                                                                              9

SEQ ID NO: 19           moltype = AA  length = 9
FEATURE                 Location/Qualifiers
SITE                    1
                        note = D-Phenylalanine
SITE                    9
                        note = thiazoline-4-carboxylic acid
SITE                    9
                        note = C-terminally amidated
source                  1..9
                        mol_type = protein
                        organism = synthetic construct
SEQUENCE: 19
FQWAVGHLX                                                                              9

SEQ ID NO: 20           moltype = AA  length = 9
FEATURE                 Location/Qualifiers
SITE                    1
                        note = D-Phenylalanine
MOD_RES                 7
                        note = N-Methylhistidine
SITE                    9
                        note = thiazoline-4-carboxylic acid
SITE                    9
                        note = C-terminally amidated
source                  1..9
                        mol_type = protein
                        organism = synthetic construct
SEQUENCE: 20
FQWAVGHLX                                                                              9
```

```
SEQ ID NO: 21              moltype = AA  length = 9
FEATURE                    Location/Qualifiers
SITE                       1
                           note = D-Phenylalanine
SITE                       3
                           note = citrulline
SITE                       9
                           note = thiazoline-4-carboxylic acid
SITE                       9
                           note = C-terminally amidated
source                     1..9
                           mol_type = protein
                           organism = synthetic construct
SEQUENCE: 21
FQXAVGHLX                                                                    9

SEQ ID NO: 22              moltype = AA  length = 10
FEATURE                    Location/Qualifiers
SITE                       1
                           note = N-terminus is modified with
                           1,4,7,10-tetraazacyclododecane- 1,4,7,10-tetraacetic acid
SITE                       1
                           note = 4-amino-1-carboxymethyl-piperidine
SITE                       2
                           note = D-Phenylalanine
SITE                       4
                           note = aplha-methyltryptophan
SITE                       6
                           note = tranexamic acid, tert-leucine
SITE                       9..10
                           note = joined by a reduced peptide bond
SITE                       10
                           note = thiazoline-4-carboxylic acid
SITE                       10
                           note = C-terminally amidated
source                     1..10
                           mol_type = protein
                           organism = synthetic construct
SEQUENCE: 22
XFQXAXGHLX                                                                  10

SEQ ID NO: 23              moltype = AA  length = 11
FEATURE                    Location/Qualifiers
SITE                       1
                           note = N-terminus is modified with
                           1,4,7,10-tetraazacyclododecane- 1,4,7,10-tetraacetic acid
SITE                       1
                           note = 4-amino-1-carboxymethyl-piperidine
SITE                       2
                           note = D-Phenylalanine
SITE                       6
                           note = tranexamic acid, tert-leucine
MOD_RES                    7
                           note = meGly
SITE                       10..11
                           note = joined by a reduced peptide bond
SITE                       11
                           note = thiazoline-4-carboxylic acid
SITE                       11
                           note = C-terminally amidated
source                     1..11
                           mol_type = protein
                           organism = synthetic construct
SEQUENCE: 23
XFQWAXNGHL X                                                                11

SEQ ID NO: 24              moltype = AA  length = 10
FEATURE                    Location/Qualifiers
SITE                       1
                           note = N-terminus is modified with
                           1,4,7,10-tetraazacyclododecane- 1,4,7,10-tetraacetic acid
SITE                       1
                           note = 4-amino-1-carboxymethyl-piperidine
SITE                       2
                           note = D-Phenylalanine
SITE                       4
                           note = 7-Fluoro-tryptophan
SITE                       10
```

|  |  |  |
|---|---|---|
| SITE | 10 | |
| | note = thiazoline-4-carboxylic acid | |
| SITE | 10 | |
| | note = C-terminally amidated | |
| source | 1..10 | |
| | mol_type = protein | |
| | organism = synthetic construct | |
| SEQUENCE: 24 | | |
| XFQXAVGHLX | | 10 |
| | | |
| SEQ ID NO: 25 | moltype = AA  length = 10 | |
| FEATURE | Location/Qualifiers | |
| SITE | 1 | |
| | note = N-terminus is modified with | |
| | 1,4,7,10-tetraazacyclododecane- 1,4,7,10-tetraacetic acid | |
| SITE | 1 | |
| | note = 4-amino-1-carboxymethyl-piperidine | |
| SITE | 2 | |
| | note = D-Phenylalanine | |
| SITE | 6 | |
| | note = tranexamic acid, tert-leucine | |
| MOD_RES | 8 | |
| | note = N-Methylhistidine | |
| SITE | 10 | |
| | note = thiazoline-4-carboxylic acid | |
| SITE | 10 | |
| | note = C-terminally amidated | |
| source | 1..10 | |
| | mol_type = protein | |
| | organism = synthetic construct | |
| SEQUENCE: 25 | | |
| XFHWAXGHLX | | 10 |
| | | |
| SEQ ID NO: 26 | moltype = AA  length = 10 | |
| FEATURE | Location/Qualifiers | |
| SITE | 1 | |
| | note = N-terminus is modified with | |
| | 1,4,7,10-tetraazacyclododecane- 1,4,7,10-tetraacetic acid | |
| SITE | 1 | |
| | note = 4-amino-1-carboxymethyl-piperidine | |
| SITE | 2 | |
| | note = D-Phenylalanine | |
| SITE | 4 | |
| | note = 5-methyltryptophan | |
| SITE | 10 | |
| | note = thiazoline-4-carboxylic acid | |
| SITE | 10 | |
| | note = C-terminally amidated | |
| source | 1..10 | |
| | mol_type = protein | |
| | organism = synthetic construct | |
| SEQUENCE: 26 | | |
| XFQXAVGHLX | | 10 |
| | | |
| SEQ ID NO: 27 | moltype = AA  length = 10 | |
| FEATURE | Location/Qualifiers | |
| SITE | 1 | |
| | note = N-terminus is modified with | |
| | 1,4,7,10-tetraazacyclododecane- 1,4,7,10-tetraacetic acid | |
| SITE | 1 | |
| | note = 4-amino-1-carboxymethyl-piperidine | |
| SITE | 2 | |
| | note = D-Phenylalanine | |
| SITE | 4 | |
| | note = 2-methyltryptophan | |
| SITE | 10 | |
| | note = thiazoline-4-carboxylic acid | |
| SITE | 10 | |
| | note = C-terminally amidated | |
| source | 1..10 | |
| | mol_type = protein | |
| | organism = synthetic construct | |
| SEQUENCE: 27 | | |
| XFQXAVGHLX | | 10 |
| | | |
| SEQ ID NO: 28 | moltype = AA  length = 11 | |
| FEATURE | Location/Qualifiers | |
| SITE | 1 | |
| | note = N-terminus is modified with | |
| | 1,4,7,10-tetraazacyclododecane- 1,4,7,10-tetraacetic acid | |

```
SITE            1
                note = 4-amino-1-carboxymethyl-piperidine
SITE            2
                note = D-Phenylalanine
MOD_RES         7
                note = meGly
SITE            10..11
                note = joined by a reduced peptide bond
SITE            11
                note = C-terminally amidated
source          1..11
                mol_type = protein
                organism = synthetic construct
SEQUENCE: 28
XFQWAVNGHL P                                                            11

SEQ ID NO: 29   moltype = AA  length = 10
FEATURE         Location/Qualifiers
SITE            1
                note = N-terminus is modified with
                 1,4,7,10-tetraazacyclododecane- 1,4,7,10-tetraacetic acid
SITE            1
                note = 4-amino-1-carboxymethyl-piperidine
SITE            2
                note = D-Phenylalanine
SITE            10
                note = thiazoline-4-carboxylic acid
SITE            10
                note = C-terminally amidated
source          1..10
                mol_type = protein
                organism = synthetic construct
SEQUENCE: 29
XFQWAVGHFX                                                              10

SEQ ID NO: 30   moltype = AA  length = 9
FEATURE         Location/Qualifiers
SITE            1
                note = D-Phenylalanine
SITE            5
                note = 2,3-dehydro-Valine
SITE            9
                note = thiazoline-4-carboxylic acid
SITE            9
                note = C-terminally amidated
source          1..9
                mol_type = protein
                organism = synthetic construct
SEQUENCE: 30
FQWAXGHLX                                                               9

SEQ ID NO: 31   moltype = AA  length = 9
FEATURE         Location/Qualifiers
SITE            1
                note = D-Phenylalanine
SITE            5
                note = L-cyclopropylglycine
SITE            9
                note = thiazoline-4-carboxylic acid
SITE            9
                note = C-terminally amidated
source          1..9
                mol_type = protein
                organism = synthetic construct
SEQUENCE: 31
FQWAXGHLX                                                               9

SEQ ID NO: 32   moltype = AA  length = 9
FEATURE         Location/Qualifiers
SITE            1
                note = D-Phenylalanine
SITE            5
                note = cyclobutaneacetic acid
SITE            9
                note = thiazoline-4-carboxylic acid
SITE            9
                note = C-terminally amidated
source          1..9
                mol_type = protein
```

```
                        organism = synthetic construct
SEQUENCE: 32
FQWAXGHLX                                                              9

SEQ ID NO: 33           moltype = AA  length = 9
FEATURE                 Location/Qualifiers
SITE                    1
                        note = D-Phenylalanine
SITE                    3
                        note = 5-Fluoro-tryptophan
SITE                    9
                        note = thiazoline-4-carboxylic acid
SITE                    9
                        note = C-terminally amidated
source                  1..9
                        mol_type = protein
                        organism = synthetic construct
SEQUENCE: 33
FQXAVGHLX                                                              9

SEQ ID NO: 34           moltype = AA  length = 9
FEATURE                 Location/Qualifiers
SITE                    1
                        note = D-Phenylalanine
SITE                    3
                        note = 6-methyltryptophan
SITE                    9
                        note = thiazoline-4-carboxylic acid
SITE                    9
                        note = C-terminally amidated
source                  1..9
                        mol_type = protein
                        organism = synthetic construct
SEQUENCE: 34
FQXAVGHLX                                                              9

SEQ ID NO: 35           moltype = AA  length = 9
FEATURE                 Location/Qualifiers
SITE                    1
                        note = D-Phenylalanine
SITE                    3
                        note = 5-hydroxytryptophan
SITE                    9
                        note = thiazoline-4-carboxylic acid
SITE                    9
                        note = C-terminally amidated
source                  1..9
                        mol_type = protein
                        organism = synthetic construct
SEQUENCE: 35
FQXAVGHLX                                                              9

SEQ ID NO: 36           moltype = AA  length = 9
FEATURE                 Location/Qualifiers
SITE                    1
                        note = D-Phenylalanine
SITE                    3
                        note = 6-Fluoro-tryptophan
SITE                    9
                        note = thiazoline-4-carboxylic acid
SITE                    9
                        note = C-terminally amidated
source                  1..9
                        mol_type = protein
                        organism = synthetic construct
SEQUENCE: 36
FQXAVGHLX                                                              9

SEQ ID NO: 37           moltype = AA  length = 9
FEATURE                 Location/Qualifiers
SITE                    1
                        note = D-Phenylalanine
SITE                    3
                        note = 7-Fluoro-tryptophan
SITE                    9
                        note = thiazoline-4-carboxylic acid
SITE                    9
                        note = C-terminally amidated
source                  1..9
```

```
                          mol_type = protein
                          organism = synthetic construct
SEQUENCE: 37
FQXAVGHLX                                                                 9

SEQ ID NO: 38             moltype = AA   length = 9
FEATURE                   Location/Qualifiers
SITE                      1
                          note = D-Phenylalanine
SITE                      3
                          note = 4-Fluoro-tryptophan
SITE                      9
                          note = thiazoline-4-carboxylic acid
SITE                      9
                          note = C-terminally amidated
source                    1..9
                          mol_type = protein
                          organism = synthetic construct
SEQUENCE: 38
FQXAVGHLX                                                                 9

SEQ ID NO: 39             moltype = AA   length = 9
FEATURE                   Location/Qualifiers
SITE                      1
                          note = D-Phenylalanine
SITE                      3
                          note = 5-methyltryptophan
SITE                      9
                          note = thiazoline-4-carboxylic acid
SITE                      9
                          note = C-terminally amidated
source                    1..9
                          mol_type = protein
                          organism = synthetic construct
SEQUENCE: 39
FQXAVGHLX                                                                 9

SEQ ID NO: 40             moltype = AA   length = 9
FEATURE                   Location/Qualifiers
SITE                      1
                          note = D-Phenylalanine
SITE                      3
                          note = 4-methyltryptophan
SITE                      9
                          note = thiazoline-4-carboxylic acid
SITE                      9
                          note = C-terminally amidated
source                    1..9
                          mol_type = protein
                          organism = synthetic construct
SEQUENCE: 40
FQXAVGHLX                                                                 9

SEQ ID NO: 41             moltype = AA   length = 9
FEATURE                   Location/Qualifiers
SITE                      1
                          note = D-Phenylalanine
SITE                      3
                          note =
                          D-2,3,4,9-tetrahydro-1H-pyrido[3,4-b]indol-3-carboxylic
                           acid
SITE                      9
                          note = thiazoline-4-carboxylic acid
SITE                      9
                          note = C-terminally amidated
source                    1..9
                          mol_type = protein
                          organism = synthetic construct
SEQUENCE: 41
FQXAVGHLX                                                                 9

SEQ ID NO: 42             moltype = AA   length = 9
FEATURE                   Location/Qualifiers
SITE                      1
                          note = D-Phenylalanine
SITE                      3
                          note = 7-methyltryptophan
SITE                      9
                          note = thiazoline-4-carboxylic acid
```

```
SITE                    9
                        note = C-terminally amidated
source                  1..9
                        mol_type = protein
                        organism = synthetic construct
SEQUENCE: 42
FQXAVGHLX                                                                         9

SEQ ID NO: 43           moltype = AA  length = 9
FEATURE                 Location/Qualifiers
SITE                    1
                        note = D-Phenylalanine
SITE                    3
                        note = 2-methyltryptophan
SITE                    9
                        note = thiazoline-4-carboxylic acid
SITE                    9
                        note = C-terminally amidated
source                  1..9
                        mol_type = protein
                        organism = synthetic construct
SEQUENCE: 43
FQXAVGHLX                                                                         9

SEQ ID NO: 44           moltype = AA  length = 9
FEATURE                 Location/Qualifiers
SITE                    1
                        note = D-Phenylalanine
SITE                    3
                        note = 7-Azatryptophan
SITE                    9
                        note = thiazoline-4-carboxylic acid
SITE                    9
                        note = C-terminally amidated
source                  1..9
                        mol_type = protein
                        organism = synthetic construct
SEQUENCE: 44
FQXAVGHLX                                                                         9

SEQ ID NO: 45           moltype = AA  length = 9
FEATURE                 Location/Qualifiers
SITE                    1
                        note = D-Phenylalanine
SITE                    3
                        note = 2-aminooctanoic acid
SITE                    9
                        note = thiazoline-4-carboxylic acid
SITE                    9
                        note = C-terminally amidated
source                  1..9
                        mol_type = protein
                        organism = synthetic construct
SEQUENCE: 45
FQXAVGHLX                                                                         9

SEQ ID NO: 46           moltype = AA  length = 10
FEATURE                 Location/Qualifiers
SITE                    1
                        note = N-terminus is modified with
                         1,4,7,10-tetraazacyclododecane- 1,4,7,10-tetraacetic acid
SITE                    1
                        note = 4-amino-1-carboxymethyl-piperidine
SITE                    2
                        note = D-Phenylalanine
SITE                    6
                        note = tranexamic acid, tert-leucine
SITE                    10
                        note = thiazoline-4-carboxylic acid
SITE                    10
                        note = C-terminally amidated
source                  1..10
                        mol_type = protein
                        organism = synthetic construct
SEQUENCE: 46
XFQWAXGHLX                                                                        10

SEQ ID NO: 47           moltype = AA  length = 10
FEATURE                 Location/Qualifiers
```

| | |
|---|---|
| SITE | 1 |
| | note = N-terminus is modified with 1,4,7,10-tetraazacyclododecane- 1,4,7,10-tetraacetic acid |
| SITE | 1 |
| | note = 4-amino-1-carboxymethyl-piperidine |
| SITE | 2 |
| | note = D-Phenylalanine |
| SITE | 10 |
| | note = thiazoline-4-carboxylic acid |
| SITE | 10 |
| | note = C-terminally amidated |
| source | 1..10 |
| | mol_type = protein |
| | organism = synthetic construct |

SEQUENCE: 47
XFQWAVGHLX                                                                      10

| | |
|---|---|
| SEQ ID NO: 48 | moltype = AA   length = 10 |
| FEATURE | Location/Qualifiers |
| SITE | 1 |
| | note = N-terminus is modified with 1,4,7,10-tetraazacyclododecane- 1,4,7,10-tetraacetic acid |
| SITE | 1 |
| | note = 4-amino-1-carboxymethyl-piperidine |
| SITE | 2 |
| | note = D-Phenylalanine |
| MOD_RES | 8 |
| | note = N-Methylhistidine |
| SITE | 10 |
| | note = thiazoline-4-carboxylic acid |
| SITE | 10 |
| | note = C-terminally amidated |
| source | 1..10 |
| | mol_type = protein |
| | organism = synthetic construct |

SEQUENCE: 48
XFQWAVGHLX                                                                      10

| | |
|---|---|
| SEQ ID NO: 49 | moltype = AA   length = 10 |
| FEATURE | Location/Qualifiers |
| SITE | 1 |
| | note = N-terminus is modified with 1,4,7,10-tetraazacyclododecane- 1,4,7,10-tetraacetic acid |
| SITE | 1 |
| | note = 4-amino-1-carboxymethyl-piperidine |
| SITE | 2 |
| | note = D-Phenylalanine |
| SITE | 4 |
| | note = citrulline |
| SITE | 10 |
| | note = thiazoline-4-carboxylic acid |
| SITE | 10 |
| | note = C-terminally amidated |
| source | 1..10 |
| | mol_type = protein |
| | organism = synthetic construct |

SEQUENCE: 49
XFQXAVGHLX                                                                      10

| | |
|---|---|
| SEQ ID NO: 50 | moltype = AA   length = 10 |
| FEATURE | Location/Qualifiers |
| SITE | 1 |
| | note = N-terminus is modified with 1,4,7,10-tetraazacyclododecane- 1,4,7,10-tetraacetic acid |
| SITE | 1 |
| | note = 4-amino-1-carboxymethyl-piperidine |
| SITE | 2 |
| | note = D-Phenylalanine |
| SITE | 6 |
| | note = 2,3-dehydro-Valine |
| SITE | 10 |
| | note = thiazoline-4-carboxylic acid |
| SITE | 10 |
| | note = C-terminally amidated |
| source | 1..10 |
| | mol_type = protein |
| | organism = synthetic construct |

SEQUENCE: 50
XFQWAXGHLX                                                                      10

```
SEQ ID NO: 51            moltype = AA   length = 10
FEATURE                  Location/Qualifiers
SITE                     1
                         note = N-terminus is modified with
                         1,4,7,10-tetraazacyclododecane- 1,4,7,10-tetraacetic acid
SITE                     1
                         note = 4-amino-1-carboxymethyl-piperidine
SITE                     2
                         note = D-Phenylalanine
SITE                     6
                         note = L-cyclopropylglycine
SITE                     10
                         note = thiazoline-4-carboxylic acid
SITE                     10
                         note = C-terminally amidated
source                   1..10
                         mol_type = protein
                         organism = synthetic construct
SEQUENCE: 51
XFQWAXGHLX                                                                    10

SEQ ID NO: 52            moltype = AA   length = 10
FEATURE                  Location/Qualifiers
SITE                     1
                         note = N-terminus is modified with
                         1,4,7,10-tetraazacyclododecane- 1,4,7,10-tetraacetic acid
SITE                     1
                         note = 4-amino-1-carboxymethyl-piperidine
SITE                     2
                         note = D-Phenylalanine
SITE                     6
                         note = cyclobutaneacetic acid
SITE                     10
                         note = thiazoline-4-carboxylic acid
SITE                     10
                         note = C-terminally amidated
source                   1..10
                         mol_type = protein
                         organism = synthetic construct
SEQUENCE: 52
XFQWAXGHLX                                                                    10

SEQ ID NO: 53            moltype = AA   length = 10
FEATURE                  Location/Qualifiers
SITE                     1
                         note = N-terminus is modified with
                         1,4,7,10-tetraazacyclododecane- 1,4,7,10-tetraacetic acid
SITE                     1
                         note = 4-amino-1-carboxymethyl-piperidine
SITE                     2
                         note = D-Phenylalanine
SITE                     4
                         note = 5-Fluoro-tryptophan
SITE                     10
                         note = thiazoline-4-carboxylic acid
SITE                     10
                         note = C-terminally amidated
source                   1..10
                         mol_type = protein
                         organism = synthetic construct
SEQUENCE: 53
XFQXAVGHLX                                                                    10

SEQ ID NO: 54            moltype = AA   length = 10
FEATURE                  Location/Qualifiers
SITE                     1
                         note = N-terminus is modified with
                         1,4,7,10-tetraazacyclododecane- 1,4,7,10-tetraacetic acid
SITE                     1
                         note = 4-amino-1-carboxymethyl-piperidine
SITE                     2
                         note = D-Phenylalanine
SITE                     4
                         note = 6-methyltryptophan
SITE                     10
                         note = thiazoline-4-carboxylic acid
SITE                     10
                         note = C-terminally amidated
```

```
source                  1..10
                        mol_type = protein
                        organism = synthetic construct
SEQUENCE: 54
XFQXAVGHLX                                                                        10

SEQ ID NO: 55           moltype = AA  length = 10
FEATURE                 Location/Qualifiers
SITE                    1
                        note = N-terminus is modified with
                         1,4,7,10-tetraazacyclododecane- 1,4,7,10-tetraacetic acid
SITE                    1
                        note = 4-amino-1-carboxymethyl-piperidine
SITE                    2
                        note = D-Phenylalanine
SITE                    4
                        note = 5-hydroxytryptophan
SITE                    10
                        note = thiazoline-4-carboxylic acid
SITE                    10
                        note = C-terminally amidated
source                  1..10
                        mol_type = protein
                        organism = synthetic construct
SEQUENCE: 55
XFQXAVGHLX                                                                        10

SEQ ID NO: 56           moltype = AA  length = 10
FEATURE                 Location/Qualifiers
SITE                    1
                        note = N-terminus is modified with
                         1,4,7,10-tetraazacyclododecane- 1,4,7,10-tetraacetic acid
SITE                    1
                        note = 4-amino-1-carboxymethyl-piperidine
SITE                    2
                        note = D-Phenylalanine
SITE                    4
                        note = 6-Fluoro-tryptophan
SITE                    10
                        note = thiazoline-4-carboxylic acid
SITE                    10
                        note = C-terminally amidated
source                  1..10
                        mol_type = protein
                        organism = synthetic construct
SEQUENCE: 56
XFQXAVGHLX                                                                        10

SEQ ID NO: 57           moltype = AA  length = 10
FEATURE                 Location/Qualifiers
SITE                    1
                        note = N-terminus is modified with
                         1,4,7,10-tetraazacyclododecane- 1,4,7,10-tetraacetic acid
SITE                    1
                        note = 4-amino-1-carboxymethyl-piperidine
SITE                    2
                        note = D-Phenylalanine
SITE                    4
                        note = 7-Fluoro-tryptophan
SITE                    10
                        note = thiazoline-4-carboxylic acid
SITE                    10
                        note = C-terminally amidated
source                  1..10
                        mol_type = protein
                        organism = synthetic construct
SEQUENCE: 57
XFQXAVGHLX                                                                        10

SEQ ID NO: 58           moltype = AA  length = 10
FEATURE                 Location/Qualifiers
SITE                    1
                        note = N-terminus is modified with
                         1,4,7,10-tetraazacyclododecane- 1,4,7,10-tetraacetic acid
SITE                    1
                        note = 4-amino-1-carboxymethyl-piperidine
SITE                    2
                        note = D-Phenylalanine
SITE                    4
```

|  |  |  |
|---|---|---|
| SITE | | note = 4-Fluoro-tryptophan |
| SITE | 10 | |
| | | note = thiazoline-4-carboxylic acid |
| SITE | 10 | |
| | | note = C-terminally amidated |
| source | 1..10 | |
| | | mol_type = protein |
| | | organism = synthetic construct |
| SEQUENCE: 58 | | |
| XFQXAVGHLX | | 10 |
| | | |
| SEQ ID NO: 59 | moltype = AA  length = 10 | |
| FEATURE | Location/Qualifiers | |
| SITE | 1 | |
| | | note = N-terminus is modified with 1,4,7,10-tetraazacyclododecane- 1,4,7,10-tetraacetic acid |
| SITE | 1 | |
| | | note = 4-amino-1-carboxymethyl-piperidine |
| SITE | 2 | |
| | | note = D-Phenylalanine |
| SITE | 4 | |
| | | note = 5-methyltryptophan |
| SITE | 10 | |
| | | note = thiazoline-4-carboxylic acid |
| SITE | 10 | |
| | | note = C-terminally amidated |
| source | 1..10 | |
| | | mol_type = protein |
| | | organism = synthetic construct |
| SEQUENCE: 59 | | |
| XFQXAVGHLX | | 10 |
| | | |
| SEQ ID NO: 60 | moltype = AA  length = 10 | |
| FEATURE | Location/Qualifiers | |
| SITE | 1 | |
| | | note = N-terminus is modified with 1,4,7,10-tetraazacyclododecane- 1,4,7,10-tetraacetic acid |
| SITE | 1 | |
| | | note = 4-amino-1-carboxymethyl-piperidine |
| SITE | 2 | |
| | | note = D-Phenylalanine |
| SITE | 4 | |
| | | note = 4-methyltryptophan |
| SITE | 10 | |
| | | note = thiazoline-4-carboxylic acid |
| SITE | 10 | |
| | | note = C-terminally amidated |
| source | 1..10 | |
| | | mol_type = protein |
| | | organism = synthetic construct |
| SEQUENCE: 60 | | |
| XFQXAVGHLX | | 10 |
| | | |
| SEQ ID NO: 61 | moltype = AA  length = 10 | |
| FEATURE | Location/Qualifiers | |
| SITE | 1 | |
| | | note = N-terminus is modified with 1,4,7,10-tetraazacyclododecane- 1,4,7,10-tetraacetic acid |
| SITE | 1 | |
| | | note = 4-amino-1-carboxymethyl-piperidine |
| SITE | 2 | |
| | | note = D-Phenylalanine |
| SITE | 4 | |
| | | note = D-2,3,4,9-tetrahydro-1H-pyrido[3,4-b]indol-3-carboxylic acid |
| SITE | 10 | |
| | | note = thiazoline-4-carboxylic acid |
| SITE | 10 | |
| | | note = C-terminally amidated |
| source | 1..10 | |
| | | mol_type = protein |
| | | organism = synthetic construct |
| SEQUENCE: 61 | | |
| XFQXAVGHLX | | 10 |
| | | |
| SEQ ID NO: 62 | moltype = AA  length = 10 | |
| FEATURE | Location/Qualifiers | |
| SITE | 1 | |

```
                          note = N-terminus is modified with
                          1,4,7,10-tetraazacyclododecane- 1,4,7,10-tetraacetic acid
SITE                      1
                          note = 4-amino-1-carboxymethyl-piperidine
SITE                      2
                          note = D-Phenylalanine
SITE                      4
                          note = 7-methyltryptophan
SITE                      10
                          note = thiazoline-4-carboxylic acid
SITE                      10
                          note = C-terminally amidated
source                    1..10
                          mol_type = protein
                          organism = synthetic construct
SEQUENCE: 62
XFQXAVGHLX                                                                        10

SEQ ID NO: 63             moltype = AA   length = 10
FEATURE                   Location/Qualifiers
SITE                      1
                          note = N-terminus is modified with
                          1,4,7,10-tetraazacyclododecane- 1,4,7,10-tetraacetic acid
SITE                      1
                          note = 4-amino-1-carboxymethyl-piperidine
SITE                      2
                          note = D-Phenylalanine
SITE                      4
                          note = 2-methyltryptophan
SITE                      10
                          note = thiazoline-4-carboxylic acid
SITE                      10
                          note = C-terminally amidated
source                    1..10
                          mol_type = protein
                          organism = synthetic construct
SEQUENCE: 63
XFQXAVGHLX                                                                        10

SEQ ID NO: 64             moltype = AA   length = 10
FEATURE                   Location/Qualifiers
SITE                      1
                          note = N-terminus is modified with
                          1,4,7,10-tetraazacyclododecane- 1,4,7,10-tetraacetic acid
SITE                      1
                          note = 4-amino-1-carboxymethyl-piperidine
SITE                      2
                          note = D-Phenylalanine
SITE                      4
                          note = 7-Azatryptophan
SITE                      10
                          note = thiazoline-4-carboxylic acid
SITE                      10
                          note = C-terminally amidated
source                    1..10
                          mol_type = protein
                          organism = synthetic construct
SEQUENCE: 64
XFQXAVGHLX                                                                        10

SEQ ID NO: 65             moltype = AA   length = 10
FEATURE                   Location/Qualifiers
SITE                      1
                          note = N-terminus is modified with
                          1,4,7,10-tetraazacyclododecane- 1,4,7,10-tetraacetic acid
SITE                      1
                          note = 4-amino-1-carboxymethyl-piperidine
SITE                      2
                          note = D-Phenylalanine
SITE                      4
                          note = 2-aminooctanoic acid
SITE                      10
                          note = thiazoline-4-carboxylic acid
SITE                      10
                          note = C-terminally amidated
source                    1..10
                          mol_type = protein
                          organism = synthetic construct
SEQUENCE: 65
```

XFQXAVGHLX                                                               10

SEQ ID NO: 66          moltype = AA  length = 10
FEATURE                Location/Qualifiers
SITE                   1
                       note = N-terminus is modified with
                       1,4,7,10-tetraazacyclododecane- 1,4,7,10-tetraacetic acid
SITE                   1
                       note = 4-amino-1-carboxymethyl-piperidine
SITE                   2
                       note = D-Phenylalanine
SITE                   9..10
                       note = joined by a reduced peptide bond
SITE                   10
                       note = thiazoline-4-carboxylic acid
SITE                   10
                       note = C-terminally amidated
source                 1..10
                       mol_type = protein
                       organism = synthetic construct
SEQUENCE: 66
XFQWAVGHLX                                                               10

SEQ ID NO: 67          moltype = AA  length = 10
FEATURE                Location/Qualifiers
SITE                   1
                       note = N-terminus is modified with
                       1,4,7,10-tetraazacyclododecane- 1,4,7,10-tetraacetic acid
SITE                   1
                       note = 4-amino-1-carboxymethyl-piperidine
SITE                   2
                       note = D-3-(2-naphtyl)alanine
SITE                   9..10
                       note = joined by a reduced peptide bond
SITE                   10
                       note = thiazoline-4-carboxylic acid
SITE                   10
                       note = C-terminally amidated
source                 1..10
                       mol_type = protein
                       organism = synthetic construct
SEQUENCE: 67
XXQWAVGHLX                                                               10

SEQ ID NO: 68          moltype = AA  length = 10
FEATURE                Location/Qualifiers
SITE                   1
                       note = N-terminus is modified with
                       1,4,7,10-tetraazacyclododecane- 1,4,7,10-tetraacetic acid
SITE                   1
                       note = 4-amino-1-carboxymethyl-piperidine
SITE                   2
                       note =
                       D-2,3,4,9-tetrahydro-1H-pyrido[3,4-b]indol-3-carboxylic
                       acid
SITE                   9..10
                       note = joined by a reduced peptide bond
SITE                   10
                       note = thiazoline-4-carboxylic acid
SITE                   10
                       note = C-terminally amidated
source                 1..10
                       mol_type = protein
                       organism = synthetic construct
SEQUENCE: 68
XXQWAVGHLX                                                               10

```
SEQ ID NO: 69            moltype = AA  length = 10
FEATURE                  Location/Qualifiers
SITE                     1
                         note = N-terminus is modified with
                         1,4,7,10-tetraazacyclododecane- 1,4,7,10-tetraacetic acid
SITE                     1
                         note = 4-amino-1-carboxymethyl-piperidine
SITE                     2
                         note = D-Phenylalanine
MOD_RES                  7
                         note = meGly
SITE                     9..10
                         note = joined by a reduced peptide bond
SITE                     10
                         note = thiazoline-4-carboxylic acid
SITE                     10
                         note = C-terminally amidated
source                   1..10
                         mol_type = protein
                         organism = synthetic construct
SEQUENCE: 69
XFQWAVGHLX                                                              10

SEQ ID NO: 70            moltype = AA  length = 11
FEATURE                  Location/Qualifiers
SITE                     1
                         note = N-terminus is modified with
                         1,4,7,10-tetraazacyclododecane- 1,4,7,10-tetraacetic acid
MOD_RES                  1
                         note = Cysteic acid
SITE                     2
                         note = 4-amino-1-carboxymethyl-piperidine
SITE                     3
                         note = D-3-(2-naphtyl)alanine
SITE                     10..11
                         note = joined by a reduced peptide bond
SITE                     11
                         note = thiazoline-4-carboxylic acid
SITE                     11
                         note = C-terminally amidated
source                   1..11
                         mol_type = protein
                         organism = synthetic construct
SEQUENCE: 70
CXXQWAVGHL X                                                            11
```